United States Patent [19]
Goulet et al.

[11] Patent Number: 5,189,042
[45] Date of Patent: Feb. 23, 1993

[54] FLUOROMACROLIDES HAVING IMMUNOSUPPRESSIVE ACTIVITY

[75] Inventors: Mark Goulet, Westfield; Thomas R. Beattie, Scotch Plains; Matthew J. Wyvratt, Mountainside, all of N.J.

[73] Assignee: Merck & Co. Inc., Rahway, N.J.

[21] Appl. No.: 748,583

[22] Filed: Aug. 22, 1991

[51] Int. Cl.$^5$ ............... A61K 31/395; A61K 31/695; C07D 498/16
[52] U.S. Cl. .................. 514/291; 514/183; 514/411; 540/456
[58] Field of Search ............... 540/456; 514/183, 291, 514/411

[56] References Cited

U.S. PATENT DOCUMENTS

| | | | |
|---|---|---|---|
| 4,650,803 | 3/1987 | Stella et al. | 514/291 |
| 4,894,366 | 1/1990 | Okuhara et al. | 514/63 |
| 4,916,138 | 4/1990 | Ueda et al. | 514/294 |
| 4,929,611 | 5/1990 | Okuhara et al. | 514/183 |
| 4,956,352 | 9/1990 | Okuhara et al. | 514/63 |
| 4,981,792 | 1/1991 | Inamine et al. | 435/119 |
| 4,987,139 | 1/1991 | Chen et al. | 514/321 |
| 5,011,844 | 4/1991 | Fehr | 514/291 |

FOREIGN PATENT DOCUMENTS

| | | | |
|---|---|---|---|
| 0315978 | 5/1989 | European Pat. Off. | 514/291 |
| 0323042 | 7/1989 | European Pat. Off. | 514/291 |
| 0349061 | 1/1990 | European Pat. Off. | 514/291 |
| 0353678 | 2/1990 | European Pat. Off. | 514/291 |
| 0356399 | 2/1990 | European Pat. Off. | 514/291 |
| 0369344 | 5/1990 | European Pat. Off. | 514/291 |
| 0388152 | 9/1990 | European Pat. Off. | 514/291 |
| 0388153 | 9/1990 | European Pat. Off. | 514/291 |
| 0413532 | 2/1991 | European Pat. Off. | 514/291 |
| 0423714 | 4/1991 | European Pat. Off. | 514/291 |
| 0427680 | 5/1991 | European Pat. Off. | 514/291 |
| 0428169 | 5/1991 | European Pat. Off. | 514/291 |
| 0428365 | 5/1991 | European Pat. Off. | 514/291 |
| 0444659 | 9/1991 | European Pat. Off. | 514/291 |
| 0444829 | 9/1991 | European Pat. Off. | 514/291 |
| 0445975 | 9/1991 | European Pat. Off. | 514/291 |
| WO89/05304 | 6/1989 | World Int. Prop. O. | 514/291 |
| WO90/14826 | 12/1990 | World Int. Prop. O. | 514/291 |
| 0402931 | 12/1990 | World Int. Prop. O. | 514/291 |
| WO91/02736 | 3/1991 | World Int. Prop. O. | 514/291 |
| WO91/04025 | 4/1991 | World Int. Prop. O. | 514/291 |
| WO91/13889 | 9/1991 | World Int. Prop. O. | 514/291 |
| WO91/13899 | 9/1991 | World Int. Prop. O. | 514/291 |

Primary Examiner—Robert T. Bond
Attorney, Agent, or Firm—Charles M. Caruso; Robert J. North; J. Eric Thies

[57] ABSTRACT

Fluoromacrolides and derivatives of the general structural Formula I:

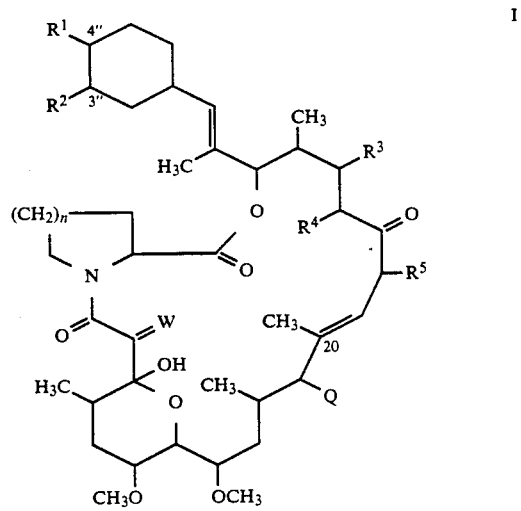

have been prepared from suitable precursors by oxidation and fluorination at C-20. These macrolide immunosuppressants are useful in a mammalian host for the treatment of autoimmune diseases, infectious diseases and/or the prevention of rejection of foreign organ transplants. In addition, these macrolide immunosuppressants are useful in the topical treatment of inflammatory and hyperproliferative skin diseases and cutaneous manifestations of immunologically-mediated illnesses. Also, these macrolides are useful in the treatment of reversible obstructive airways disease, particularly asthma. Furthermore, these macrolides are useful as hair revitalizing agents, especially in the treatment of male pattern alopecia or alopecia senilis.

21 Claims, No Drawings

FLUOROMACROLIDES HAVING IMMUNOSUPPRESSIVE ACTIVITY

SUMMARY OF THE INVENTION

The present invention is related to fluoromacrolides which are useful in a mammalian host for the treatment of autoimmune diseases (such as juvenile-onset diabetes mellitus, multiple sclerosis, rheumatoid arthritis, liver disease, posterior uveitis, allergic encephalomyelitis, and glomerulonephritis), immunodepression, infectious diseases and/or the prevention of rejection of foreign organ transplants, e.g. bone marrow, kidney, liver, heart, skin, small-bowel, and pancreatic-islet-cell transplants, and are also useful in the topical treatment of inflammatory and hyperproliferative skin diseases and cutaneous manifestations of immunologically-medicated illnesses (such as: psoriasis, atopical dermatitiis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus, Alopecia areata) male pattern alopecia, alopecia senilis, reversible obstructive airways disease, particularly asthma, and/or hepatic injury associated with ischemia.

More particularly, this invention relates to compounds of the general structural Formula I:

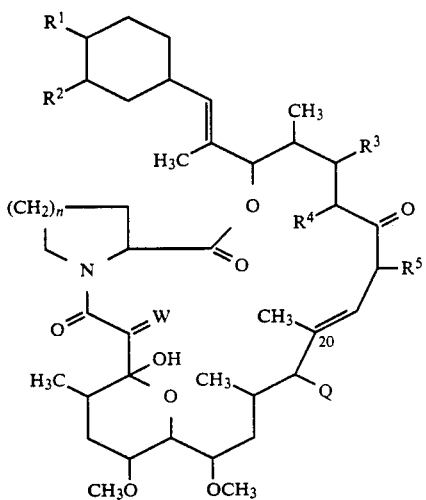

wherein $R^1$, $R^2$, $R^3$, $R^4$, $R^5$, Q, W and n are hereinafter defined.

This invention also relates to pharmaceutical compositions containing the compounds and to a method of use of the present compounds for the treatment of autoimmune diseases, immunodepression, infectious diseases, the rejection of foreign organ transplants, reversible obstructive airways disease, inflammatory and hyperproliferative skin diseases and/or cutaneous manifestations of immunologically-mediated illnesses.

BRIEF DESCRIPTION OF THE DISCLOSURES IN THE ART

Fujisawa United States, European and Japanese patents and applications (U.S. Pat. No. 4,894,366, issued Jan. 16, 1990, EPO Publication No. 0,184,162 and PBJ Disclosure 63-17784) and publications (J. Am. Chem. Soc., 1987, 109, 5031 and J. Antibiotics, 1987, 40, 1249) disclose 17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (FR-9005006), (FK-506), (L-679,934), 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (FR-900520) and related compounds which are the starting materials for the preparation of the compounds described. The synthetic preparation of the aforementioned starting material (FR-900506) has recently been reported (J. Am. Chem. Soc., 1989, 111, 1157). A Sandoz European patent application (EPO Publication No. 0,356,399) discloses steroisomers of FR-900506 and derivatives at the 17-position. Fisons European and WIPO patent applications (EPO Publication No. 0,323,042 and PCT Publication No. WO 89/05304) discloses various derivatives of FR-900506, FR-900520 and related compounds. A Sandoz European Patent application (EPO Publication No. 0,437,680) discloses chloro, bromo, iodo and azido derivatives of FR-900506, FR-900520 and relates compounds. A Merck European Patent application (EPO Publication No. 0,428,365) discloses various amino derivatives of FR-900506, FR-900520 and related compounds.

Fujisawa United States patents (U.S. Pat. No. 4,929,611, issued May 29, 1990 and U.S. Pat. No. 4,956,352, issued Sep. 11, 1990) discloses the use of FK-506-type compounds in treating resistance to transplantation. A Sandoz European patent (EPO Publication No. 0,315,978) discloses the use of FR-900506 and related compounds in the topical treatment of inflammatory and hyperproliferative skin diseases and of cutaneous manifestations of immunologically-mediated illness. A Fisons WIPO patent application (PCT Publication No. WO 91/04025) discloses the use of various derivatives of FR-900506 in the treatment of immunodepression. A Fisons WIPO patent application (PCT Publication WO 90/14826) discloses the use of FR-900506 and relates compounds in the treatment of reversible obstructive airways disease, particularly (EPO Publication No. 0,423,7140) discloses the use of FK-506 and derivatives as hair revitalizing agents. Various studies have suggested the efficacy of FK-506 in the treatment of a number of ailments, including rheumatoid arthritis (C. Arita, et al., Clinical exp. Immunol., 1990, 82, 456–461; N. Inamura, et al., Clin. Immunol. Immunopathol. 1988, 46, 82–90), recent-onset diabetes (N. Murase, et al., Diabetes, 1990, 39, 1584–86; N. Murase, et al., Lancet, 1990, 336, 373–74), posterior uveitis (H. Kawashima, Invest. Ophthalmol., Vis. Sci., 1988, 29, 1265–71), hepatic injury associated with ischemia (M. Sakr, et al., Life Sci., 1990, 47, 687–91) allergic encephalomyelitis (K, Deguchi, et al., Brain Nerve, 1990, 42, 391–97), glomeralonephritis (J. McCauley, et al., Lancet, 1990, 335, 674) and systemic lupus erythematosus (K. Takabayashi, et al., Clin. Immunol. Immunopathol., 1989, 51, 110–117).

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type 1 diabetes mellitus, inflammatory bowel disease, biliary cirrhosis, uveitis, multiple sclerosis and other disorders such as Chrons disease, ulcerative colitis, bullous pemphigoid, sarcoidosis, psoriasis, ichthyosis, and Graves opthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiinflammatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A which was licensed by the US FDA in 1983 is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting less side effects are constantly being searched for in the field.

The 23-membered tricyclo-macrolide immunosuppressant, FK-506 (FR-900506),

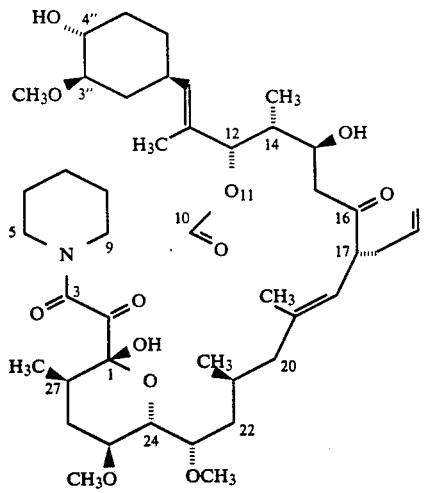

(17-allyl-1,14-dihydroxy-12-[2'-(4'''-hydroxy-3'''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone) and related compounds which were isolated and characterized by Tanaka, Kuroda, and co-workers at Fujisawa Pharmaceutical Co. in Japan (see *J. Am. Chem. Soc.,* 1987, 109, 5031, and U.S. Pat. No. 4,894,366, issued Jan. 16, 1990) have been shown to possess exceptional immunosuppressive activity. In particular, the compound FK-506 (FR-900506) has been reported to be 100 times more effective than cyclosporin in the suppression of in vitro immune systems (*J. Antibiotics* 1987, 40, 1256). In addition, these compounds are reputed to possess topical activity in the treatment of inflammatory and hyperproliferative skin diseases and cutaneous manifestations of immunologically-mediated illnesses (EPO Pub. No. 0,315,978).

The compound FK-506 and related compounds further have been suggested to be useful in the treatment of obstructive airways disease, particularly asthma (PCT Publication WO 90/14826), male pattern alopecia or alopecia senilis (EPO Publication No. 0,423,714), rheumatoid arthritis (C. Arita, et al., *Clincial exp. Immunol.,* 1990, 82, 456–461; N. Inamura, et al., *Clin. Immunol. Immunopathol.* 1988, 46, 82–90), recent-onset diabetes (N. Murase, et al., *Diabetes,* 1990, 39, 1584–86; N. Murase, et al., *Lancet,* 1990, 336, 373–74), posterior uveitis (H. Kawashima, *Invest. Ophthalmol. Vis. Sci.,* 1988, 29, 1265–71), hepatic injury associated with ischemia (M. Sakr, et al., *Life Sci.,* 1990, 47, 687–91) allergic encephalomyelitis (K, Deguchi, et al., *Brain Nerve,* 1990, 42, 391–97), glomerulonephritis (J. McCauley, et al., *Lancet,* 1990, 335, 674) and systemic lupus erythematosus (K. Takabayashi, et al., *Clin. Immunol. Immunopathol.,* 1989, 51, 110–117).

Accordingly, an object of the present invention is to provide new analogs of these tricyclomacrolides which will (1) restore the balance of the help-and-suppression mechanism of the immune system by acting at an earlier point that the anti-inflammatory agents and (2) induce specific long-term transplantation tolerance through a suppressor cell circuit without increasing the body's susceptibility to infection.

An additional object of the present invention is to provide new analogs of these tricyclomacrolide immunosuppressants which act as antagonists of macrocyclic immunosuppressive compounds, including derivatives of 12-(2'-cyclohexyl-1'-methylvinyl)-13,19,21,27-tetramethyl-11,28-dioxa-4-azatricyclo-[22.3.1.0$^{4,9}$]octacos-18-ene, and so would be useful in the treatment of immunodepression or in the modification of the immunosuppressive activity or toxicity of such macrocyclic immunosuppressive compounds.

Another object of the present invention is to provide analogs of these tricyclo-macrolides which possess topical activity in the treatment of inflammatory and hyperproliferative skin diseases and cutaneous manifestations of immunologically-mediated illnesses.

An additional object of the present invention is to provide pharmaceutical compositions for administering to a patient in need of the treatment one or more of the active immunosuppressive agents of the present invention.

Still a further object of this invention is to provide a method of controlling graft rejection, autoimmune and chronic inflammatory diseases by administering a sufficient amount of one or more of the novel immunosuppressive agents in a mammalian species in need of such treatment.

Finally, it is the object of this invention to provide processes for the preparation of the active compounds of the present invention.

DETAILED DESCRIPTION OF THE INVENTION

A. Scope of the Invention

The novel compound of this invention has structural Formula I:

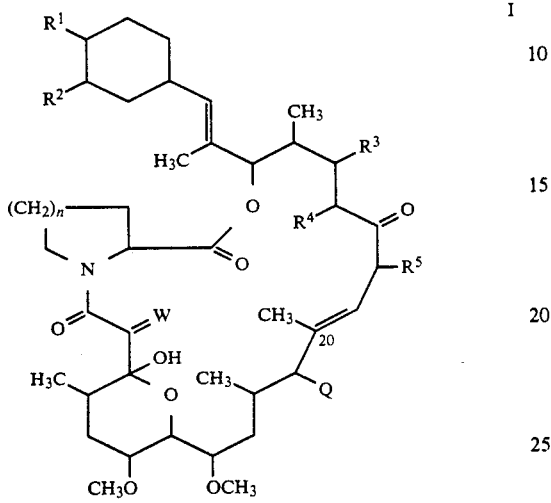

or a pharmaceutically acceptable salt thereof, wherein:

$R^1$ and $R^2$ are independently selected from:
1) $-N_3$;
2) $-HNCN$;
3) $-NR^6R^7$, wherein $R^6$ and $R^7$ independently, are,
   a) hydrogen,
   b) $C_{1-12}$ alkyl, unsubstituted or substituted with $R^8$ and $R^9$, wherein $R^8$ and $R^9$ are independently selected from the group consisting of:
      i) hydrogen,
      ii) $-OH$,
      iii) $C_{1-6}$ alkoxy,
      iv) $-O-CO-C_{1-6}$ alkyl,
      v) $-NR^{10}R^{11}$, wherein $R^{10}$ and $R^{11}$ are independently, hydrogen, or $C_{1-6}$ alkyl, unsubstituted or substituted with phenyl
      vi) $-CONR^{10}R^{11}$,
      vii) $-CO_2H$,
      viii) $-CO-O-C_{1-6}$ alkyl,
      ix) $-S-C_{1-6}$ alkyl,
      x) $-SO-C_{1-6}$ alkyl,
      xi) $-SO_2-C_{1-6}$ alkyl,
      xii) halo, such as Cl, Br, F or I,
      xiii) $-C_{3-7}$-cycloalkyl,
      xiv) phenyl, unsubstituted or substituted with X, Y and Z,
      xv) naphthyl, unsubstituted or substituted with X, Y and Z,
      xvi) $-CF_3$,
   c) $C_{3-12}$ alkenyl, unsubstituted or substituted with $R^8$ and $R^9$, wherein $R^8$ and $R^9$ are as defined above,
   d) $C_{3-7}$ cycloalkyl, unsubstituted or substituted with $R^8$ and $R^9$, wherein $R^8$ and $R^9$ are as defined above,
   e) phenyl, unsubstituted or substituted with X, Y and Z,
   f) naphthyl, unsubstituted or substituted with X, Y and Z,
   g) $-SO_2$-phenyl, wherein phenyl is unsubstituted or substituted with X, Y and Z,
   h) $-SO_2-C_{1-6}$ alkyl,
   i) or where $R^6$ and $R^7$ and the N to which they are attached may form an unsubstituted or substituted 3- to 7-membered heterocyclic ring which may include one or two additional heteroatoms independently selected from the group consisting of O, S, or $NR^{10}$, wherein $R^{10}$ is as defined above, such as morpholine, thiomorpholine, piperidine, piperizine, and where the substituent(s), attached to the carbon atom(s) in the heterocyclic ring is/are independently selected from the group consisting of:
      i) hydrogen,
      ii) $-OH$,
      iii) $C_{1-6}$ alkoxy,
      iv) $-O-CO-C_{1-6}$ alkyl,
      v) $-NR^{10}R^{11}$, wherein $R^{10}$ and $R^{11}$ are as defined above,
      vi) $-CONR^{10}R^{11}$,
      vii) $-CO_2H$,
      viii) $-CO-O-C_{1-6}$ alkyl,
      ix) $-SH$,
      x) halo, such as Cl, Br, F or I,
      xi) phenyl, unsubstituted or substituted with X, Y and Z,
      xii) naphthyl, unsubstituted or substituted with X, Y and Z,
      xiii) $-CF_3$;
4) $-N(R^6)CO-O-R^{12}$, wherein $R^6$ is as defined above and $R^{12}$ is $C_{1-12}$ alkyl, unsubstituted or substituted with $R^8$ and $R^9$, wherein $R^8$ and $R^9$ are as defined above;
5) $-N(R^6)CO-R^{13}$, wherein $R^6$ is as defined above and $R^{13}$ is
   a) hydrogen,
   b) $C_{1-12}$ alkyl, unsubstituted or substituted with $R^8$ and $R^9$, wherein $R^8$ and $R^9$ are as defined above,
   c) $C_{3-12}$ cycloalkyl, unsubstituted or substituted with $R^8$ and $R^9$, wherein $R^8$ and $R^9$ are as defined above,
   d) phenyl, unsubstituted or substituted with X, Y and Z,
   e) naphthyl, unsubstituted or substituted with X, Y and Z, or
   f) where $R^6$ and $R^{13}$ and the $-NCO-$ to which they are attached may form an unsubstituted or substituted 5- to 7-membered heterocyclic ring which may include one or two additional heteroatoms independently selected from the group consisting of O, S, or $NR^{10}$, wherein $R^{10}$ is as defined above, such as pyrrolidone, or piperidinone;
6) $-N(R^{14})COCH(R^{22})NR^6R^7$ wherein $R^6$ and $R^7$ are as defined above, $R^{14}$ is selected from the definitions of $R^6$, and $R^{22}$ is
   a) hydrogen,
   b) $C_{1-4}$ alkyl, unsubstituted or substituted with $R^{23}$, wherein $R^{23}$ is selected from the group consisting of:
      i) $-OH$,
      ii) $C_{1-6}$ alkoxy,
      iii) $-O-CO-C_{1-6}$ alkyl,
      iv) $-SH$,
      v) $-S-C_{1-6}$ alkyl, vi) —NR$^{10}$R$^{11}$, wherein R$^{10}$ and R$^{11}$ are as defined above,
vii) —CO$_2$H,
viii) —CONH$_2$,
ix) imidazolyl,
x) indolyl,
xi) phenyl, and
xii) p-hydroxyphenyl, or
c) phenyl;
7) —N(R$^{14}$)CO(CH$_2$)$_m$NR$^6$R$^7$, wherein m is 0 or 2-6, R$^6$ and R$^7$ are as defined above, and R$^{14}$ is selected from the definitions of R$^6$, or where R$^{14}$ and R$^6$ and the —NCO(CH$_2$)$_m$N— to which they are attached may form an unsubstituted or substituted 5- to 7-membered heterocyclic ring, such as 2-imidazolidone;
8) —N=C(R$^{14}$)—NR$^6$R$^7$, wherein R$^6$ and R$^7$ are as defined above, and R$^{14}$ is selected from the definitions of R$^6$, and wherein if either R$^6$ or R$^7$ are hydrogen, the tautomeric structure —NHC(R$^{14}$)=NR$^{6\ or\ 7}$ is also possible;
9) —N(R$^{15}$)$_3{}^+$ A$^-$, wherein R$^{15}$ is C$_{1-6}$ alkyl, unsubstituted or substituted with phenyl or naphthyl, and wherein A$^-$ is a counterion; and

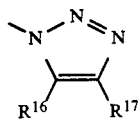

wherein R$^{16}$ and R$^{17}$ are independently,
a) hydrogen,
b) phenyl, unsubstituted or substituted with X, Y and Z,
c) naphthyl, unsubstituted or substituted with X, Y and Z,
d) —CN,
e) —CF$_3$,
f) —CO—C$_{1-6}$alkyl, or
g) —CO—O—C$_{1-6}$alkyl;
11) C$_{1-10}$ alkoxy;
12) substituted C$_{1-10}$ alkoxy in which one or more substituent(s) is(are) selected from:
a) hydroxy,
b) C$_{1-6}$ alkoxy,
c) phenyl C$_{1-3}$ alkoxy,
d) substituted phenyl C$_{1-3}$ alkoxy, in which the substituents on phenyl are X, Y and Z,
e) —OCOC$_{1-6}$ alkyl,
f) —NR$^{10}$R$^{11}$, wherein R$^{10}$ and R$^{11}$ are independently hydrogen, or C$_{1-6}$ alkyl unsubstituted or substituted with phenyl, which may be substituted with X, Y and Z,
g) —NR$^6$CO—C$_{1-6}$ alkyl, wherein R$^6$ is as defined above,
h) —COOR$^6$, wherein R$^6$ is as defined above,
i) —CHO,
j) phenyl,
k) substituted phenyl in which the substituents are X, Y and Z,
l) phenyloxy,
m) substituted phenyloxy in which the substituents are X, Y and Z,
n) 1- or 2- naphthyl,
o) substituted 1- or 2-naphthyl in which the substituents are X, Y and Z,
p) biphenyl, and
q) substituted biphenyl in which the substituents are X, Y and Z;
13) C$_{3-10}$ alkenyloxy;
14) substituted C$_{3-10}$ alkenyloxy in which one or more substituent(s) is(are) selected from:
a) hydroxy,
b) C$_{1-6}$ alkoxy,
c) —OCO—C$_{1-6}$ alkyl,
d) C$_{2-8}$ alkenyl,
e) phenyl,
f) substituted phenyl in which the substituents are X, Y and Z,
g) 1- or 2- naphthyl,
h) substituted 1- or 2-naphthyl in which the substituents are X, Y and Z,
i) biphenyl, and
j) substituted biphenyl in which the substituents are X, Y and Z;
15) C$_{3-10}$ alkynyloxy;
16) substituted C$_{3-10}$ alkynyloxy in which one or more substituent(s) is(are) selected from:
a) hydroxy,
b) C$_{1-6}$ alkoxy,
c) —OCO—C$_{1-6}$ alkyl,
d) phenyl,
e) substituted phenyl in which the substituents are X, Y and Z,
f) 1- or 2-naphthyl,
g) substituted 1- or 2- naphthyl in which the substituents are X, Y and Z,
h) biphenyl, and
i) substituted biphenyl in which the substituents are X, Y and Z;
17) phenyloxy;
18) substituted phenyloxy in which the substituents are X, Y and Z;
19) 1- or 2- naphthyloxy;
20) substituted 1- or 2- naphthyloxy in which the substituents are X, Y and Z;
21) biphenyloxy;
22) substituted biphenyloxy in which the substituents are X, Y and Z; and
23) hydroxy; or
24) where R$^1$ and R$^2$ may both be connected to form a 3- to 7-membered heterocyclic ring of the form:

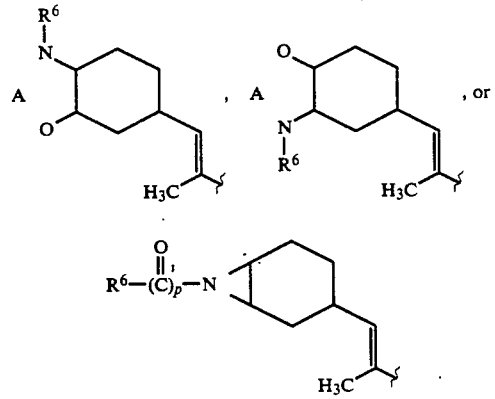

wherein p is zero or one, R$^6$ is as defined above, and A is
a) —CO—,
b) —CS—, c) —CO—C$_1$-alkyl,
d) —CS—C$_1$-alkyl, or
e) —C$_{1-2}$-alkyl, wherein the alkyl may be unsubstituted or substituted with one or more of the following:
  i) —OH,
  ii) C$_{1-6}$ alkyl,
  iii) C$_{1-6}$ alkoxy,
  iv) —O—CO—C$_{1-6}$ alkyl,
  v) —NR$^9$R$^{10}$, wherein R$^9$ and R$^{10}$ are as defined above,
  vi) —CONR$^9$R$^{10}$,
  vii) —CO$_2$H,
  viii) —CO—O—C$_{1-6}$ alkyl,
  ix) —S—C$_{1-6}$ alkyl,
  x) —SO—C$_{1-6}$ alkyl,
  xi) —SO$_2$—C$_{1-6}$ alkyl,
  xii) halo, such as Cl, Br, F or I
  xiii) phenyl, unsubstituted or substituted with X, Y and Z, or
  xiv) naphthyl unsubstituted or substituted with X, Y and Z;

R$^3$ is hydrogen, hydroxy, or C$_{1-6}$ alkoxy;
R$^4$ is hydrogen, or R$^3$ and R$^4$ taken together form a double bond;
R$^5$ is methyl, ethyl, propyl or allyl;
Q is F or OH, with the proviso that if Q is OH, R$^2$ is other than OH or OCH$_3$;
W is O or (H, OH);
X, Y and Z independently are selected from:
a) hydrogen,
b) C$_{1-7}$ alkyl,
c) C$_{2-6}$ alkenyl,
d) halo, such as Cl, Br, F or I,
e) —(CH$_2$)$_t$—NR$^{10}$R$^{11}$, wherein R$^{10}$ and R$^{11}$ are as defined above and t is 0 to 2,
f) —CN,
g) —CHO,
h) —CF$_3$,
i) —SR$^{18}$, wherein R$^{18}$ is hydrogen, C$_{1-6}$alkyl, or phenyl,
j) —SOR$^{18}$, wherein R$^{18}$ is as defined above,
k) —SO$_2$R$^{18}$, wherein R$^{18}$ is as defined above,
l) —CONR$^{10}$R$^{11}$, wherein R$^{10}$ and R$^{11}$ are as defined above,
m) R$^{19}$O(CH$_2$)$_t$— wherein R$^{19}$ is hydrogen, C$_{1-3}$, alkyl, hydroxy-C$_{2-3}$alkyl, phenyl or naphthyl and t is as defined above;
n) —CH(OR$^{20}$)(OR$^{21}$), wherein R$^{20}$ and R$^{21}$ are C$_{1-3}$ alkyl or taken together form an ethyl or propyl bridge,
o)

wherein R$^{19}$ and t are as defined above; and
p)

wherein R$^{19}$ and t are as defined above;
or any two of X, Y and Z may be joined to form a saturated ring having 5, 6 or 7 ring atoms, said ring atoms comprising 0, 1 or 2 oxygen atoms, the remaining ring atoms being carbon, such as dioxolanyl or dioxanyl; and n is 1 or 2.

The compounds of the present invention have asymmetric centers and this invention includes all of the optical isomers and mixtures thereof.

In addition compounds with carbon-carbon double bonds may occur in Z- and E- forms with all isomeric forms of the compounds being included in the present invention.

When any variable (e.g., alkyl, aryl, R$^6$, R$^7$, R$^8$, R$^9$, etc.) occurs more than one time in any variable or in Formula I, its definition on each ocurrence is independent of its definition at every other occurrence.

As used herein, the term "alkyl" includes those saturated hydrocarbon groups of a specified number of carbon atoms of either a straight, branched, or cyclic configuration. Representative examples of "alkyl" include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge.

"Alkanoyl" is intended to include those alkylcarbonyl groups of specified number of carbon atoms, which are exemplified by formyl, acetyl, propanoyl and butanoyl; "alkanoyloxy" is intended to include those alkylcarbonyl groups of specified number of carbon atoms attached through an oxygen bridge, which are exemplified by formyloxy, acetoxy, propionoyloxy, and butyryloxy. "Alkenyl" is intended to include hydrocarbon chains of either a straight- or branched- configuration and at least one unsaturation, which may occur at any point along the chain, such as ethenyl, propenyl, butenyl, pentenyl, dimethylpentyl, and the like, and includes E and Z forms, where applicable; and "arylalkyl" represents aryl groups as herein defined which are attached through a straight or branched chain alkyl group of from one to six carbon atoms, such as, for example, benzyl, phenethyl, 3,3-diphenylpropyl, and the like. "Halogen", as used herein, means fluoro, chloro, bromo and iodo, and "counterion" is used to represent a small negatively-charged species, such as chloride, bromide, iodide, hydroxide, nitrate, acetate, citrate, benzoate, perchlorate, benzene sulfonate, tartrate, hemitartrate, maleate, and the like.

The following additional abbreviations have also been used herein:

| Abbreviated Designation | Reagent |
| --- | --- |
| TFA | trifluoroacetic acid |
| Et3N | triethylamine |
| TBSOTf | t-butyldimethylsilyl trifluoromethanesulfonate |
| DAST | diethylaminosulfur trifluoride |
| SeO$_2$ | selenium dioxide |
| HF | hydrogen fluoride |
| | Solvent |
| HOAc (AcOH) | acetic acid |
| CH$_2$Cl$_2$ | methylene chloride |
| DMF | dimethylformamide |
| DMSO | dimethyl sulfoxide |
| EtOAc | ethyl acetate |
| EtOH | ethanol |
| Et$_2$O | diethylether |
| MeOH | methanol |
| THF | tetrahydrofuran |

| Abbreviated Designation | Reagent |
|---|---|
| CH₃CN | acetonitrile |
| | Protecting Group |
| TBS | t-butyldimethylsilyl |

Suitable protecting groups for hydroxyl include those groups well known in the art which are: 1-(lower alkyl-thio)(lower)alkyl, wherein "lower alkyl" indicates a straight, cyclic or branched chain of one to six carbon atoms, such as lower alkylthiomethyl (e.g. methylthiomethyl, ethylthiomethyl, propylthiomethyl, isopropylthiomethyl, butylthiomethyl, isobutylthiomethyl, hexylthiomethyl, etc.), and the like, in which the preferred one may be $C_1$-$C_4$ alkylthiomethyl and the most preferred one may be methylthiomethyl; trisubstituted silyl such as tri(lower)alkylsilyl (e.g. trimethylsilyl, triethylsilyl, tributysilyl, tri-i-propylsilyl, t-butyldimethylsilyl, tri-t-butylsilyl, etc.), lower alkyldiarylsilyl (e.g. methyl-diphenylsilyl, ethyl-diphenylsilyl, propyl-diphenylsilyl, t-butyldiphenylsilyl, etc.), and the like, in which the preferred one may be tri($C_1$-$C_4$)alkylsilyl and $C_1$-$C_4$ alkyldiphenylsilyl, and the most preferred one may be tert-butyl-dimethylsilyl, tri-i-propylsilyl and tert-butyl-diphenylsilyl; acyl such as aliphatic acyl, aromatic acyl and aliphatic acyl substituted with aromatic group, which are derived from carboxylic acids; and the like.

In the present invention it is preferred that in compounds of Formula I:

$R^1$ and $R^2$ are independently selected from:
1) —$NR_3$;
2) —$NR^6R^7$, wherein $R^6$ and $R^7$ independently, are,
   a) hydrogen,
   b) $C_{1-12}$alkyl, unsubstituted or substituted with $R^8$ and $R^9$, wherein $R^8$ and $R^9$ are independently selected from the group consisting of:
      i) hydrogen,
      ii) —OH,
      iii) —O—CO—$C_{1-6}$alkyl,
      iv) —$NR^{10}R^{11}$, wherein $R^{10}$ and $R^{11}$ are independently, hydrogen, or $C_{1-6}$alkyl, unsubstituted or substituted with phenyl
      v) —$CONR^{10}R^{11}$,
      vi) —$CO_2H$,
      vii) —CO—O—$C_{1-6}$alkyl, and
      viii) phenyl, unsubstituted or substituted with X, Y and Z,
   c) $C_{3-12}$alkenyl, unsubstituted or substituted with $R^8$ and $R^9$, wherein $R^8$ and $R^9$ are as defined above,
   d) or where $R^6$ and $R^7$ and the N to which they are attached may form an unsubstituted or substituted 3- to 7-membered heterocyclic ring which may include one or two additional heteroatoms independently selected from the group consisting of O, S, or $NR^{10}$, wherein $R^{10}$ is as defined above, such as morpholine, thiomorpholine, piperidine, piperizine, and where the substituent(s), attached to the carbon atom(s) in the heterocyclic ring is/are independently selected from the group consisting of:
      i) hydrogen,
      ii) —OH,
      iii) —O—CO—$C_{1-6}$alkyl,
      iv) —$CONR^{10}R^{11}$,
      v) —$CO_2H$,
      vi) —CO—O—$C_{1-6}$alkyl, and
      vii) phenyl, unsubstituted or substituted with X, Y and Z;
3) —$N(R^6)CO$—O—$R^{12}$, wherein $R^6$ is as defined above and $R^{12}$ is $C_{1-12}$alkyl, unsubstituted or substituted with $R^8$ and $R^9$, wherein $R^8$ and $R^9$ are as defined above;
4) —$N(R^6)CO$—$R^{13}$, wherein $R^6$ is as defined above and $R^{13}$ is
   a) hydrogen,
   b) $C_{1-12}$alkyl, unsubstituted or substituted with $R^8$ and $R^9$, wherein $R^8$ and $R^9$ are as defined above,
   c) $C_{3-12}$cycloalkyl, unsubstituted or substituted with $R^8$ and $R^9$, wherein $R^8$ and $R^9$ are as defined above, or
   d) phenyl, unsubstituted or substituted with X, Y and Z;
5) —$N(R^{14})COCH(R^{22})NR^6R^7$ wherein $R^6$ and $R^7$ are as defined above, $R^{14}$ is selected from the definitions of $R^6$, and $R^{22}$ is
   a) hydrogen,
   b) $C_{1-4}$alkyl, unsubstituted or substituted with $R^{23}$, wherein $R^{23}$ is selected from the group consisting of:
      i) —OH,
      ii) $C_{1-6}$alkoxy,
      iii) —O—CO—$C_{1-6}$alkyl,
      iv) —SH,
      v) —S—$C_{1-6}$alkyl,
      vi) —$NR^{10}R^{11}$, wherein $R^{10}$ and $R^{11}$ are as defined above,
      vii) —$CO_2H$,
      viii) —$CONH_2$,
      ix) imidazolyl,
      x) indolyl,
      xi) phenyl, and
      xii) p-hydroxyphenyl, or
   c) phenyl;
6) —$N(R^{14})CO(CH_2)_mNR^6R^7$, wherein m is 0 or 2-6, $R^6$ and $R^7$ are as defined above, and $R^{14}$ is selected from the definitions of $R^6$, or where $R^{14}$ and $R^6$ and the —$NCO(CH_2)_mN$— to which they are attached may form an unsubstituted or substituted 5- to 7-membered heterocyclic ring, such as 2-imidazolidone;
7) —N=C($R^{14}$)—$NR^6R^7$, wherein $R^6$ and $R^7$ are as defined above, and $R^{14}$ is selected from the definitions of $R^6$, and wherein if either $R^6$ or $R^7$ are hydrogen, the tautomeric structure —NHC($R^{14}$)=$NR^{6or7}$ is also possible;
8) —$N(R^{15})_3^+$ $A^-$, wherein $R^{15}$ is $C_{1-6}$ alkyl, unsubstituted or substituted with phenyl or naphthyl, and wherein $A^-$ is a counterion; and
9)

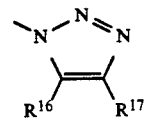

wherein $R^{16}$ and $R^{17}$ are independently.
   a) hydrogen,
   b) phenyl, unsubstituted or substituted with X, Y and Z, c) naphthyl, unsubstituted or substituted with X, Y and Z,
d) —CN,
e) —CF$_3$,
f) —CO—C$_{1-6}$alkyl, or
g) —CO—O—C$_{1-6}$alkyl;
10) C$_{1-10}$alkoxy;
11) substituted C$_{1-10}$alkoxy in which one or more substituent(s) is(are) selected from:
a) hydroxy,
b) C$_{1-6}$alkoxy,
c) phenyl C$_{1-3}$alkoxy,
d) substituted phenyl C$_{1-3}$alkoxy, in which the substituents on phenyl are X, Y and Z.
e) —OCOC$_{1-6}$ alkyl,
f) —NR$^{10}$R$^{11}$, wherein R$^{10}$ and R$^{11}$ are as defined above,
g) —NR$^6$CO—C$_{1-6}$ alkyl, wherein R$^6$ is as defined above,
h) —COOR$^6$, wherein R$^6$ is as defined above,
i) —CHO,
j) phenyl,
k) substituted phenyl in which the substituents are X, Y and Z,
l) phenyloxy, and
m) substituted phenyloxy in which the substituents are X, Y and Z;
12) C$_{3-10}$ alkenyloxy;
12) substituted C$_{3-10}$ alkenyloxy in which one or more substituent(s) is (are) selected from:
a) hydroxy,
b) C$_{1-6}$ alkoxy,
c) —OCO—C$_{1-6}$ alkyl,
d) C$_{2-8}$ alkenyl,
e) phenyl, and f) substituted phenyl in which the substituents are X, Y and Z;
14) C$_{3-10}$ alkenyloxy;
15) substituted C$_{3-10}$ alkynyloxy in which one or more substituent(s) is (are) selected from:
a) hydroxy,
b) C$_{1-6}$ alkoxy,
c) —OCO—C$_{1-6}$ alkyl,
d) phenyl, and
e) substituted phenyl in which the substituents are X, Y and Z;
16) phenyloxy;
17) substituted phenyloxy in which the substituents are X, Y and Z;
18) 1- or 2-naphthyloxy;
19) substituted 1- or 2-naphthyloxy in which the substituents are X, Y and Z; and
20) hydroxy; or
21) where R$^1$ and R$^2$ may both be connected to form a 3- to 7-membered heterocyclic ring of the form:

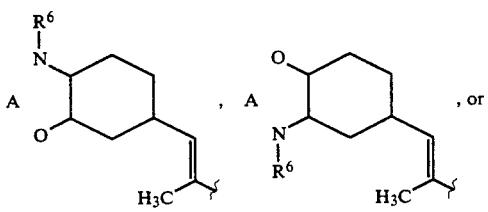

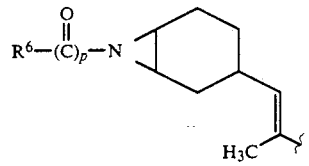

wherein p is one, R$^6$ is as defined above, and A is
a) —CO—,
b) —CO—C$_1$-alkyl, or
c) C$_{1-2}$-alkyl;
R$^3$ is hydrogen or hydroxy;
R$^4$ is hydrogen;
R$^5$ is ethyl, propyl or allyl;
Q is F or OH, with the proviso that if Q is OH, R$^2$ is other than OH or OCH$_3$;
W is O or (H, OH);
X, Y and Z independently are selected from:
a) hydrogen,
b) C$_{1-7}$ alkyl,
c) C$_{2-6}$ alkenyl,
d) halo, such as Cl, Br, F or I,
e) —CHO,
—CONR$^{10}$R$^{11}$, wherein R$^{10}$ and R$^{11}$ are as defined above,
g) R$^{19}$O(CH$_2$)$_t$— wherein R$^{19}$ is hydrogen, C$_{1-3}$ alkyl, hydroxy-C$_{2-3}$alkyl, phenyl or naphthyl and t is 0 to 2;
h) —CH(OR$^{20}$)(OR$^{21}$), wherein R$^{20}$ and R$^{21}$ are C$_{1-3}$ alkyl or taken together form an ethyl or propyl bridge,
i)

wherein R$^{19}$ and t are as defined above; and
j)

wherein R$^{19}$ and t are as defined above;
or any two of X, Y and Z may be joined to form a saturated ring having 5, 6 or 7 ring atoms, said ring atoms comprising 0, 1 or 2 oxygen atoms, the remaining ring atoms being carbon, such as dioxolanyl or dioxanyl; and
n is 1 or 2,
and pharmaceutically acceptable salts thereof.

Preferred compounds of the present invention are the compounds identified as follows:
17-Ethyl-20-fluoro-1-hydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;
17-Ethyl-20-fluoro-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;
17-Ethyl-20-fluoro-1-hydroxy-12-[2'-(3",4"-dihydroxycyclohexyl)-1'-methylvinyl]-23,25-dimethoxy- 13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(3",4"-dihydroxy-cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4"-azido-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4"-amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-azido-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-acetylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-N-(2-propenyl)-amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-N-methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4"-N-methylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-1'''-adamantanecarboxamido-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-cyclopropanecarboxamido-3"-methoxycyclohexyl)-1'-methylvinyl]-23,25-di-methoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-formamido-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-{2'-[4"-(4''',5'''-dicarboethoxy-1''',2''',3'''-triazole)-3'-methoxycyclohexyl]-1'-methylvinyl}-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4"-acetylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-amino-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(3"-amino-4"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-20-fluoro-1,14-dihydroxy-12-[2'-(4"-azido-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-20-fluoro-1,14-dihydroxy-12-[2'-(4"-amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-20-fluoro-1,14-dihydroxy-12-[2'-(4"-acetylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-20-fluoro-1-hydroxy-12-[2'-(4"-amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-20-fluoro-1-hydroxy-12-[4'-(4"-acetylamino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-20-fluoro-1,14-dihydroxy-12-[2'-(4"-amino-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-20-fluoro-1,14-dihydroxy-12-[2'-(4"-hydroxy-3"-aminocyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-beta-amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-alpha-amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4"-beta-amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4"-alpha-amino-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-amino-3"-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4"-amino-3"-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-amino-3"-n-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-amino-3"-n-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4'-amino-3"-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4"-amino-3"-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4"-methylcarbamate-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4"-benzylcarbamate-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-acetamidine-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4"-benzamidine-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4"-formamidine-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(L-phenylalanyl)-amido3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4"-(L-phenylalanyl)amido3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(D-phenylalanyl)amido-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4"-(D-phenylalanyl)amido-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(aminoacetylamino)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4"-(aminoacetylamino)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(2-hydroxypropylamino)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4"-(2-hydroxypropylamino)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(1-aza-4-oxabicyclo-[4.4.0]dec-6-yl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(1-aza-4-oxabicyclo[4.4.0]-dec-6-yl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-trimethylamino-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraoneiodine;

17-Allyl-20-fluoro-1,14-dihydroxy-12-[2'-(4"-amino-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-20-fluoro-1-hydroxy-12-[2'-(4"-amino-3"-isopropoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Propyl-20-fluoro-1-hydroxy-12-[2'-(4"-amino-3"-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-acetylamino-3"-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(N'-t-butoxycarbonyl-D-phenylalanine)amido-3"-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(N'-t-butoxycarbonyl-L-phenylalanine(amido-3"-n- propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-acetoxyacetylamino-3''-ethoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1,14-dihydroxy-12-[2'-(4''-(N'-t-butoxycarbonyl-L-phenylalanine(amido-3''ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-(4''-cyclopropanecarboxamido-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2-(4''-formamido-3''-n-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-{2'-[4''',5'''-dicarboethyloxy-1''',2''',3'''-triazole)-3''-n-propyloxycyclohexyl]-1'-methyl-vinyl}-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4''-amino-3''-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-benzylamino-3''-isopropyloxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1,14-dihydroxy-12-[2'-(4''-trimethylamino-3''-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,2,14-trihydroxy-12-[2'-(4''-acetylamino3''-n-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-{2'-[4''-(N'-4''-phenylaminocarbonyl)amino)-3''-isopropyloxycyclohexyl]-1'-methylvinyl}-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-{2'-[4''-(ethoxycarbonyl)-amino-3''-n-propyloxycyclohexyl)-1'-methylvinyl}-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4''-acetylamino-3''-n-propyloxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1,14-dihydroxy-12-[2'-(4''-dimethylamino-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1-hydroxy-12-[2'-(4''-dimethylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-benzylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4''-benzylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4''-dimethylamino-3''-isopropyloxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1-hydroxy-12-[2'-(4''-dimethylamino-3''-n-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4''-benzylamino-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4''-benzylamino-3''-n-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4''-(2-phenyl-2-hydroxyethyl)amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4''-morpholino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-morpholino-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1-hydroxy-12-[2'-(4''-amino-3''-n-butyloxycyclohexyl)-1'-methylvinyl]-23,25-dimethoxy-13,19,21,27-tetramethyl-11,18-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-amino-3''-butyloxycyclohexyl)-1'-methylvinyl]-23,25-dimethoxy-13,19,21,27-tetramethyl-11,28-dioxa-4-azatricyclo[22:3.1.0$^{4,9}$]octacos-18-ene-2,3,10,16-tetraone;

17-Ethyl-20-fluoro-1-hydroxy-12-[2'-(4'''-amino-3''-(3-methylbutyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4'''-amino-3''-(3-methylbutyloxycyclohexyl)-1'-methylvinyl]-23,25-dimethoxy-13,19,21,27-tetramethyl- 11,28-dioxa-4-azatricyclo-[22.3.1.0⁴,⁹]octacos-18-ene-2,3,10,16-tetraone;

17-Ethyl-20-fluoro-1-hydroxy-12-[2'-(4'''-amino-3''-(2-methylbutyloxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4'''-amino-3''-(2-methylbutyloxy)cyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1-hydroxy-12-[2'-(4''-(N-(2-methyl-3-(4-hydroxyphenyl)propenyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-Ethyl-20-fluoro-1,14-dihydroxy-12-[2'-(4''-(N-(2-methyl-3-(4-hydroxyphenyl)propenyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-1-2-[2'-(4''-(N-(3-(4-hydroxyphenyl)-propenyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-Ethyl-20-fluoro-1,14-dihydroxy-12-[2'-(4''-(N-(3-(4-hydroxyphenyl)propenyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-(N-(3-phenylpropenyl)amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-(N-3-phenylpropenyl)-amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(L-Trp)amido-3'-'-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-phenyloxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(3''-phenyloxy-4''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-phenyloxy-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-(4'''-fluorophenyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-(4'''-chlorophenyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-(4'''-methylphenyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(3''-(4'''-methylphenyloxy)-4''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-(4'''-methylphenyloxy)-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-(4'''-phenoxyphenyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-(4'''-phenoxyphenyloxy)-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-(3'''-phenoxyphenyloxy)-4''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-(naphth-1-yloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(3''-(naphth-1-yloxy)-4''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-(naphth-1-yloxy)-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-(naphth-2-yloxy)-3''-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1,14-dihydroxy-12-[2'-(4''-(naphth-2-yloxy)-3''-hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1,14-dihydroxy-12-[2'-(3''-(naphth-2-yloxy)-4''-hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1-hydroxy-12-[2'-(4"-(naphth-2-yloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1,14-dihydroxy-12-[2'-(4"-(6'''-methoxynaphth-2-yloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1,14-dihydroxy--12-[2'-(3"-(6'''-methoxynaphth-2-yloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy--12-[2'-(4"-(6'''-methoxynaphth-2-yloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(3"-(4'''-methoxyphenyloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(4'''-methoxyphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(3"-(3'''-methoxyphenyloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(3'''-methoxyphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(3"-(3'''-hydroxyphenyloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(4'''-hydroxyphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy--12-[2'-(4"-(6'''-hydroxynaphth-2-yloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy--12-[2'-(3"-(6'''-hydroxynaphth-2-yloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12--[2'-(4"-(3''',4'''-dichlorophenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(phenanthr-9-yl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(3''',4'''-methylenedioxyphenyloxy)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(2''',3'''-dihydrobenzofuran-5-yl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-20-fluoro-1,14-dihydroxy-12-[2'-(4"-naphth-2-yl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(-4"-(1''',4'''-benzodioxane-6-yl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,2,14-trihydroxy-12-[2'-(4"-(naphth-2-yl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-3,10,16-tetraone;

17-Ethyl-20-fluoro-1,14-dihydroxy-12-[2'-(4"-allyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(2-butynyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-cinnamyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(3"-methoxy-4"-phenylpropyloxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1,14-dihydroxy-12-[2'-(4"-allyloxy-3"-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1,14-dihydroxy-12-[2'-(3"-allyloxy-4"-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1,14-dihydroxy-12-[2'-(3"-hydroxy-4"-isopropyloxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1,14-dihydroxy-12-[2'-(4"-hydroxy-3"-isopropyloxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1,14-dihydroxy-12-[2'-(4"-secbutenyloxy-3"-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetranone;

17-Ethyl-20-fluoro-1,14-dihydroxy-12-[2'-(3"-secbutenyloxy-4"-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1,14-dihydroxy-12-[2'-(4"-(trans-2-butenyloxy-3"-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1,14-dihydroxy-12-[2'-(3"-(trans-2-butenyloxy-4"-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1,14-dihydroxy-12-[2'-(3"-hydroxy-4"-(3-methyl-2-butenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,4-dihydroxy-12-[2'-(4"-hydroxy-3"-(3-methyl-2-butenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(3"-hydroxy-4"-(2-methylpropenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-hydroxy-3"-(2-methylpropenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"'-cinnamyloxy-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(3"-cinnamyloxy-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4"-sec-butenyloxy-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(3"-sec-butenyloxy-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4"'-cinnamyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(3"-methoxy-4"-phenylpropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(4"'-methoxyphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(3"'-methoxyphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(6"'-hydroxynaphth-2-yloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(4"'-hydroxyphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(4"'-methylthiophenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(2"'-methylphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(3"'-methylphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(3"',4"'-dimethylphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4"-allyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4"-(2-butynyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4"'-cinnamyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(3"-methoxy-4"-phenylpropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4"-allyloxy-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(3''-allyloxy-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(3''-hydroxy-4''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4''-hydroxy-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4''-(trans-2-butenyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(3''-(trans-2-butenyloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(3''-hydroxy-4''-(3''-methyl-2-butenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4''-hydroxy-3''-(3''-methyl-2-butenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(3''-hydroxy-4''-(2-methylpropenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4''-hydroxy-3''-(2-methylpropenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(3''-cinnamyloxy-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4'''-sec-phenethyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-(2-methylcinnamyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-(4-methyl-2,4-hexadienyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-(p-methoxycinnamyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4'''-(3''',4''-methylenedioxycinnamyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-(4,4-dimethyl-2-trans-pentenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-(3-cyclohexyl-2-trans-propenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-p-fluorocinnamyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-p-chlorocinnamyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-p-bromocinnamyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(3''-methoxy-4''-p-fluorophenylpropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(3'',4''-diallyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(3'', 4''-dipropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-(2-benzyl amino)-ethoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4'''-(2-benzyl amino)-ethoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-(2-benzyloxyethoxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-(4-benzyloxymethoxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-(4-(napth-2-yloxy)-3''-allyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-(ethoxycarbomethoxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-(p-hydroxycinnamyl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4"-(p-hydroxycinnamyl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4'-(3'''-5'''-difluorocinnamyl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4"-(3''',5'''-difluorocinnamyl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-allyl-20-fluoro-1,14-dihydroxy-12-[2'-(4"-amino-3"-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-allyl-20-fluoro-1-hydroxy-12-[2'-(4"-amino-3"-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-20-fluoro-1,14-dihydroxy-12-[2'-(4"-amino-3"-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-20-fluoro-1-hydroxy-12-[2'-(4"'-amino-3"-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-20-fluoro-1-hydroxy-12-[2'-(4"-phenoxy-3"-aminocyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-20-fluoro-1-hydroxy-12-[2'-(4"-dimethylamino-3"-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-20-fluoro-1-hydroxy-12-[2'-(4"-amino-3"-(4"'-methoxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-20-fluoro-1-hydroxy-12-[2'-(4"-amino-3"-(4"'-hydroxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-20-fluoro-1-hydroxy-12-[2'-(4"-acetylamino-3"-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-20-fluoro-1-hydroxy-12-[2'-(4"'-amino-3'-(4'''-fluorophenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-20-fluoro-1,14-dihydroxy-12-[2'-(4"-amino-3'-(4"'-carboxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-20-fluoro-1-hydroxy-12-[2'-(4"'-amino-3"-(4"'-trifluoromethylphenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-20-fluoro-1-hydroxy-12-[2'-(4"-amino-3"-(3''',4'''-dimethoxyphenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-allyl-20-fluoro-1,14-dihydroxy-12-[2'-(4"-amino-3'-(4'''-methoxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-20-fluoro-1-hydroxy-12-[2'-(4"-amino-3"-(4'''-methylphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-20-fluoro-1,14-dihydroxy-12-[2'-(4"-amino-3"-(4'''-methylphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-20-fluoro-1-hydroxy-12-[2'-(4"-amino-3"-(3"'-methoxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-20-fluoro-1-hydroxy-12-[2'-(4"-amino-3"-(3"'-hydroxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-20-fluoro-1-hydroxy-12-[2'-(4"-N-(2-propenyl)amino-3"-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-ethyl-20-fluoro-1-hydroxy-12-[2'-(4"-(acetylamino-3"(4'''-methoxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-amino-3"-allyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4"-amino-3"-allyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-allyloxy-3''-aminocyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-amino-3''-cinnamyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-amino-3''-cinnamyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-20-fluoro-1,14-dihydroxy-12-[2'-(4''-amino-3''-cinnamyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-amino-3''-(3'''-phenylpropyloxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-amino-3'''-(3'''-phenylpropyloxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-amino-3''-(2'''-benzyloxyethoxy)-cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20fluoro-1-hydroxy-12-[2'-(4''-amino-3''-(2'''-benzyloxyethoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-amino-3''-(4'''-hydroxycinnamyloxy)cyclohexyl)-1'-methylvinyl]-23,25-dimethoxy-13,19,21,27-tetramethyl-11,28-sioxa-4-azatricyclo[22.3.1.0⁴,⁹]octacos-18-ene-2,3,10,16-tetraone;

17-Ethyl-20-fluoro-1-hydroxy-12-[2'-(4''-amino-3''-(4'''-hydroxycinnamyloxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-20-fluoro-1,14-dihydroxy-12-[2'-(4''-amino-3''-(4'''-hydroxycinnamyloxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17Allyl-20-fluoro-1-hydroxy-12-[2'-(4''-amino-3''-(4'''-hydroxycinnamyloxy)cyclohexyl)-1'-methylvinyl]-23,25-dimethoxy-13,19,21,27-tetramethyl-37 11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-acetylamino-3''-allyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1-hydroxy-12-[2'-(4''-acetylamino-3''-allyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1-hydroxy-12-[2'-(4''-propenyl)amino-3''-allyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1,14-dihydroxy-12-[2'-(4''-(L-phenylalanine)-amido-3''-allyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1,14-dihydroxy-12-[2'-(4''-(D-phenylalanine)-amido-3''-allyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1-hydroxy-12-[2'-(4''-cyclopropanecarboxamido-3''-allyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1-hydroxy-12-[2'-(4''-formamido-3''-allyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20fluoro-1,14-dihydroxy-12-[2'-(4''-(4''',5'''-dicarboethoxy-1''',2''',3'''-triazole)-3''-allyloxycyclohexyl)-1'-methylvinyl]-23,25-dimethoxy-13,19,21,27-tetramethyl-11,28-dioxa-4azatricyclo[22.3.1.0⁴,⁹]octacos-18-ene-2,3,10,16-tetraone;

17-Ethyl-20-fluoro-1-hydroxy-12-[2'-(4''-benzylamino-3''-allyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1-hydroxy-12-[2'-(4''-dimethylamino-3''-allyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1,14-dihydroxy-12-[2'-(4''-trimethylamino-3''-allyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone iodide;

17-Ethyl-20-fluoro-1,2,14-trihydroxy-12-[2'-(4''-acetylamino-3''-allyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-trione;

17-Ethyl-20-fluoro-1,14-dihydroxy-12-[2'-(4''-N-phenylaminocarbonyl)amino-3''-allyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1,14-dihydroxy-12-[2'-(4''-(ethoxycarbonyl)-3''-allyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1,14-dihydroxy-12-[2'-(4''-amino-3''-sec-butenyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1-hydroxy-12-[2'-(4''-amino-3'''-sec-butenyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1,14-dihydroxy-12-[2'-(4''-amino-3''-(3-methyl-2-butenyloxy)cyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1-hydroxy-12-[2'-(4''-amino-3''-3'''-methyl-2-butenyloxy)cyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1,14-dihydroxy-12-[2'-(4''-amino-3'-(2-methyl-propenyloxy)cyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1-hydroxy-12-[2'-(4''-amino-3'''-(2-methylpropenyloxy)cyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1-hydroxy-12-[2'-(4''-amino-3''-(4'''-methyloxycinnamyloxy)cyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1-hydroxy-12-[2'-(4''-amino-3''-(4'''-fluorocinnamyloxy)cyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone; and 17-Ethyl-20-fluoro-1-hydroxy-12-[2'-(4''-amino-3''-(2-butynyloxy)-cyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

and pharmaceutically acceptable salts thereof.

B. Preparation of Compounds Within the Scope of the Present Invention

The starting materials for the preparation of the compounds of this invention are represented by Formula II:

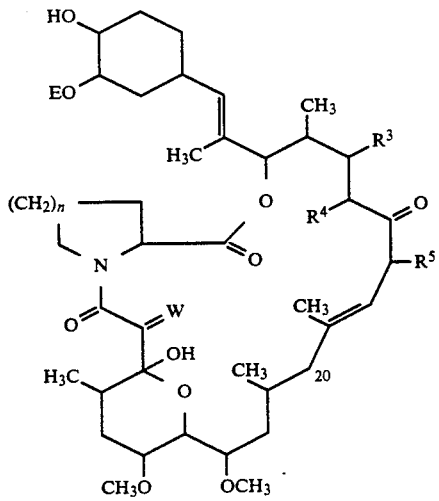

wherein:
E is hydrogen or methyl;
W is O or (H, OH);
$R^3$ is hydrogen, hydroxy, or $C_{1-6}$ alkoxy;
$R^4$ is hydrogen, or $R^3$ and $R^4$ taken together form a double bond;
$R^5$ is methyl, ethyl, propyl or allyl; and
n is 1 or 2.

The production and characterization of compounds of Formula II is well known in the literature (see U.S. Pat. No. 4,894,366 issued Jan. 16, 1990; U.S. Pat. No. 4,929,611, issued May 29, 1990; U.S. Pat. No. 3,244,592, issued Apr. 15, 1966; EPO Publication No. 0,323,042; EPO Publication No. 0,356,399; PBJ Disclosure 63-17884; *J. Am. Chem. Soc.*, 1987, 109, 5031; and *J. Antibiotics*, 1987, 40, 1249). Both biological fermentation and synthetic processes may be found. A synthetic route to compounds of Formula II can involve modifications of a route described in *J. Am. Chem. Soc.*, 1989, 111, 1157.

Biological fermentation follower by synthetic modification is presently favored in the art as the method to produce compounds of Formula II. Organisms belonging to the genius Streptomyces such as *Streptomyces tsukubaensis*, No. 9933 placed in an aqueous nutrient medium will produce desired compounds in isolable amounts. The nutrient medium contains sources of assimilable carbon and nitrogen, preferably under aerobic conditions. Produced in fermentation are four compounds of Formula II, (A) where E is methyl, W is O, $R^3$ is hydroxyl, $R^4$ is hydrogen, $R^5$ is allyl and n is 2; (B) where E is methyl, W is O, $R^3$ is hydroxyl, $R^4$ is hydrogen, $R^5$ is ethyl and n is 2; (C) where E is methyl, W is O, $R^3$ is hydroxyl, $R^4$ is hydrogen, $R^5$ is methyl and n is 2; and (D) where E is methyl, W is O, $R^3$ is hydroxyl, $R^4$ is hydrogen, $R^5$ is allyl and n is 1.

A lyophilized sample of the isolated *Streptomyces tsukubaensis*, No. 9993 was deposited with the Fermentation Research Institute, Agency of Industrial Science and Technology (No. 1-3, Higashi 1-chome, Yatabemachi Tsukuba-gun, Ibaraki Prefecture, Japan) under the deposit number of FERM P-7886 (deposit date: Oct. 5th, 1984), and then converted to Budapest Treaty route of the same depository on Oct. 19, 1985 under the new deposit number of FERM BP-927.

Using the four compounds produced in fermentation above, the remaining compounds of Formula II may be easily produced. The allyl of $R^5$ may be conveniently reduced to propyl by well known methods, for example as described in U.S. Pat. No. 4,894,366. The hydroxy of $R^3$ may be protected by well known methods, for example as disclosed in EPO Publication No. 0,323,042. Likewise, the hydroxyl at C-4'' may also be protected. In addition, the hydroxy of $R^3$ may be reduced to a hydrogen or eliminated to form a double bond with $R^4$ (by methods disclosed in U.S. Pat. No. 4,894,366 or EPO Publication No. 0,323,042). The carbonyl of W may be reduced to the alcohol by methods disclosed in EPO Publication No. 0,323,042 or by methods disclosed in U.S. Ser. No. 486,700, filed Mar. 1, 1990. It is preferred that the carbonyl of W be reduced to the alcohol after the introduction of a fluoro group at C-20.

The methyl of E as produced may be replaced with hydrogen or demethylated and subsequently protected as desired, if necessary. This demethylation of compounds wherein E is methyl may be carried out in a fermentation reaction using the compounds of Formula II as a feedstock. For instance, compound A named under Formula II above may be demethylated at E above by using the microorganism Actinomycetales ATCC No. 53771 (described in U.S. Pat. No. 4,981,792, issued Jan. 1, 1991). Similarly, compound B named under Formula II above may be demethylated at E above using the microorganism Actinoplanacete sp. ATCC No. 53771 (described in EPO Publication No. 0,349,061). In addition the compound of Formula II wherein E is H, W is O, $R^3$ is hydroxy, $R^4$ is hydrogen, $R^5$ is ethyl and n is 2 may be produced directly by fermentation using the mutant microorganism Streptomyces hygroscopicus sup. ascomyceticus, No. 53855 (being a blocked mutant of Streptomyces hygroscopicus sup. ascomyceticus, No. 14891) (as described in EPO Publication No. 0,388,152. Similarly, the compound of Formula II wherein E is hydrogen, W is O, $R^3$ is hydroxy, $R^4$ is hydrogen, $R^5$ is methyl and n is 2 may be produced directly by fermentation using the mutant microorganism Streptomyces hygroscopicus sup. ascomyceticus, No. 53855 (being a blocked mutant of Streptomyces hygroscopicus sup. ascomyceticus, No. 14891) (as described in EPO Publication No. 0,388,153). Also, the compound of Formula II wherein E is hydrogen, $R^3$ is hydroxy, $R^4$ is hydrogen, $R^5$ is allyl, W is O and n is 2 and the compound of Formula II wherein EO is keto, $R^3$ is hydroxy, $R^4$ is hydrogen, $R^5$ is allyl, W is O and n is 2 may be produced directly by fermentation using the microorganism Streptomyces tskukubaensis, No. 9993 (described in EPO Publication No. 0,353,678). The hydroxy of C-3" may be protected by methods similar to those known for the protection of the hydroxyl groups of $R^3$ and/or C-4", for example as disclosed in U.S. Pat. No. 4,894,366. The hydroxy of C-3" and /or C-4" may be modified to form nitrogen substituted macrolides essentially by methods described in EPO Publication No. 0,428,365, or by methods as described herein.

Suitable protecting groups for hydroxyl include those groups well known in the art which are:

1-(lower alkylthio)(lower)alkyl, wherein "lower alkyl" indicates a straight, cyclic or branched chain of one to six carbon atoms, such as lower alkylthiomethyl (e.g. methylthiomethyl, ethylthiomethyl, propylthiomethyl, isopropylthiomethyl, butylthiomethyl, isobutylthiomethyl, hexylthiomethyl, etc.), and the like, in which the preferred one may be $C_1$-$C_4$ alkylthiomethyl and the most preferred one may be methylthiomethyl; trisubstituted silyl such as tri(lower)alkylsilyl (e.g. trimethylsilyl, triethylsilyl, tributylsilyl, tri-i-propylsilyl, t-butyldimethylsilyl, tri-t-butylsilyl, etc.), lower alkyl-diarylsilyl (e.g. methyl-diphenylsilyl, ethyl-diphenylsilyl, propyl-diphenylsilyl, t-butyldiphenylsilyl, etc.), and the like, in which the preferred one may be tri($C_1$-$C_4$)alkylsilyl and $C_1$-$C_4$ alkyldiphenylsilyl, and the most preferred one may be tert-butyl-dimethylsilyl, tri-isopropylsilyl and tert-butyl-diphenylsilyl; acyl such as aliphatic acyl, aromatic acyl and aliphatic acyl substituted with aromatic group, which are derived from carboxylic acids; and the like.

Compounds A, B, C and D of Formula II, organisms to produce the same, conditions of fermentation, separation techniques, and chemical modification of the products are fully described in EPO Publication No. 4,894,366, issued Jan. 16, 1990.

The novel processes for preparing the novel compounds of the present invention are illustrated as follows, wherein $R^1$, $R^2$, $R^3$, $R^5$, Q, W and n are as defined above unless otherwise indicated.

REACTION SCHEME A

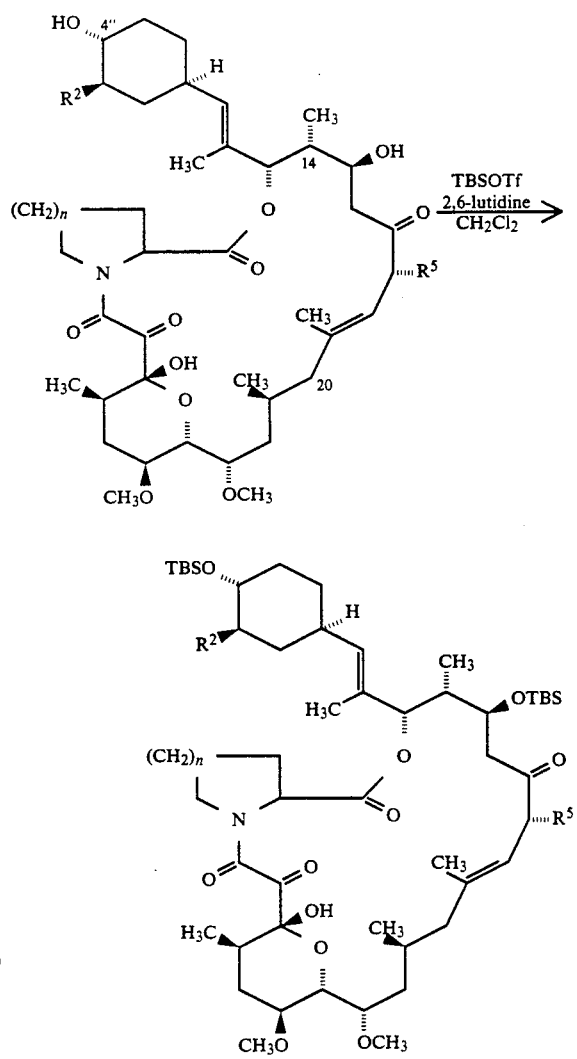

REACTION SCHEME B

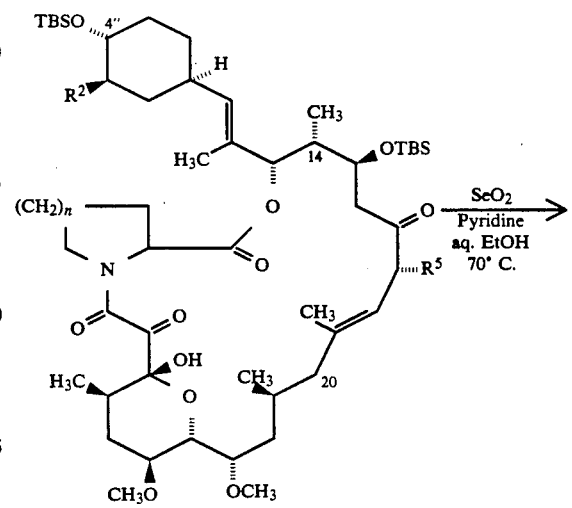

-continued
REACTION SCHEME B
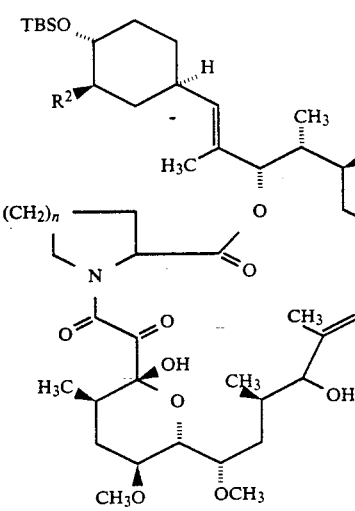
REACTION SCHEME C
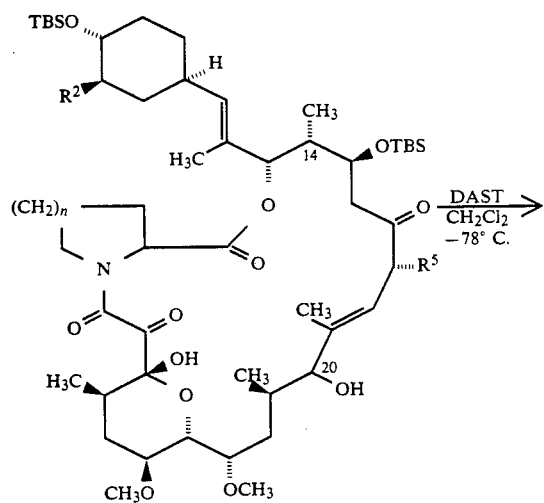
DAST
CH$_2$Cl$_2$
−78° C.
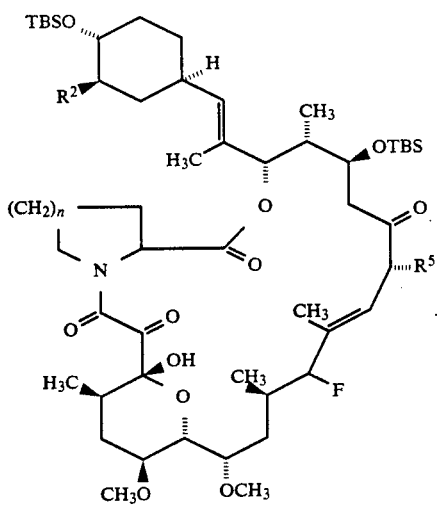
REACTION SCHEME D
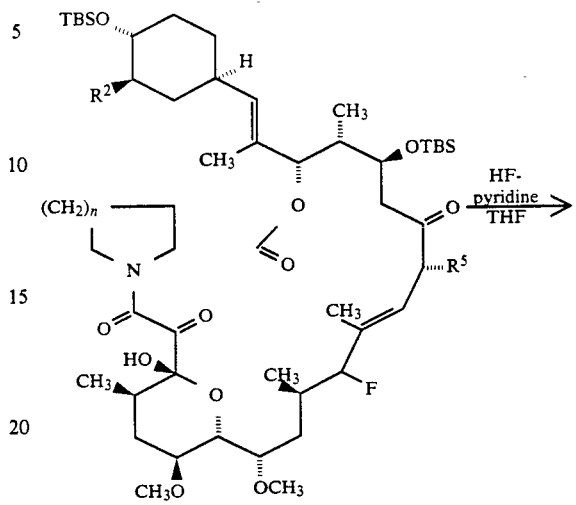
HF-pyridine
THF
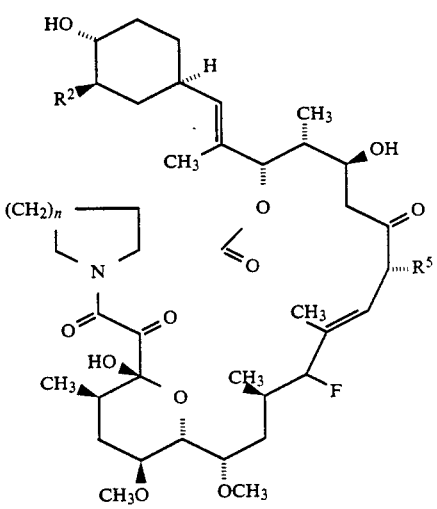
REACTION SCHEME E
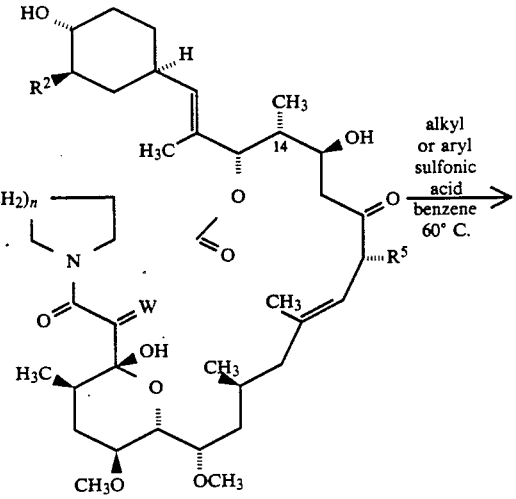
alkyl or aryl sulfonic acid
benzene
60° C.

REACTION SCHEME E
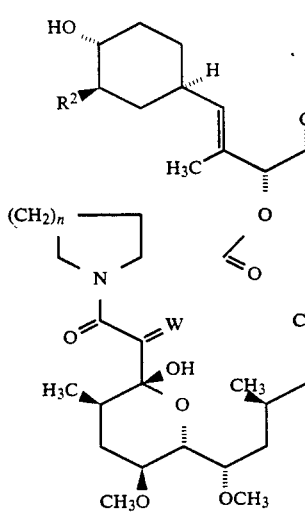
REACTION SCHEME F
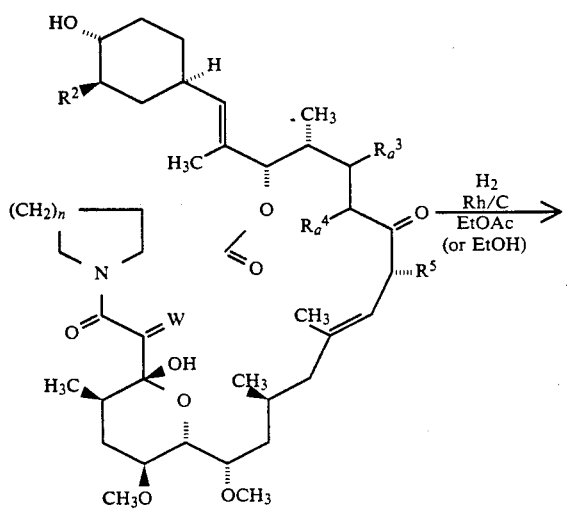
REACTION SCHEME G
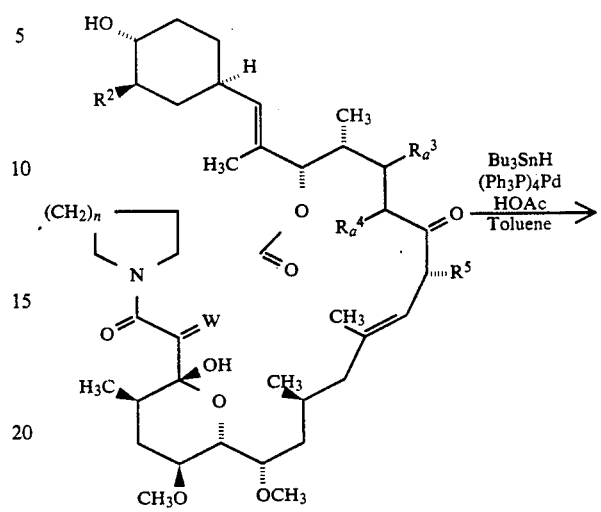
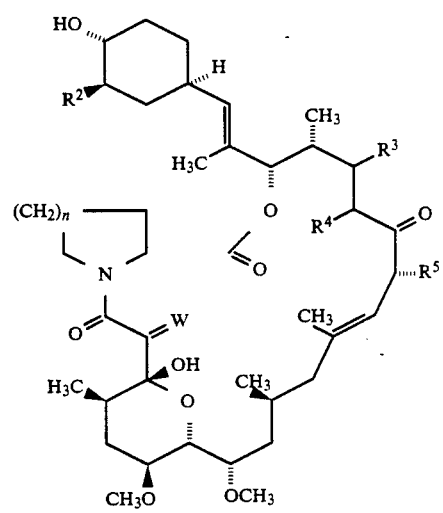
REACTION SCHEME H
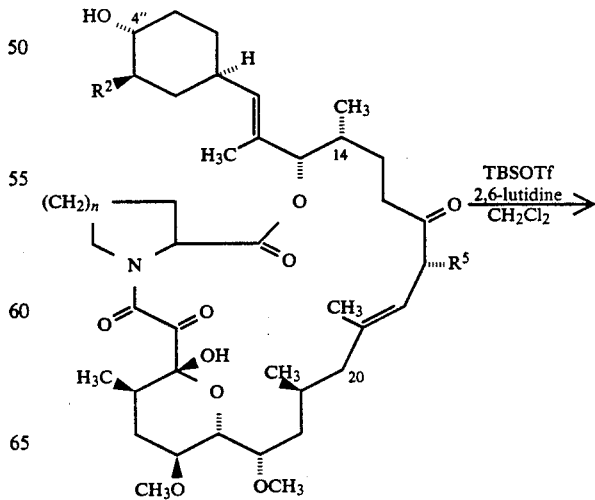
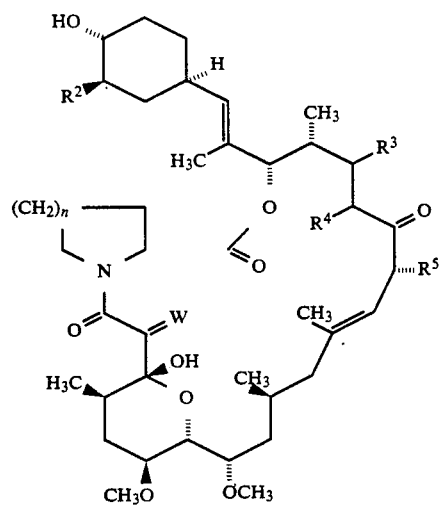

-continued
REACTION SCHEME H
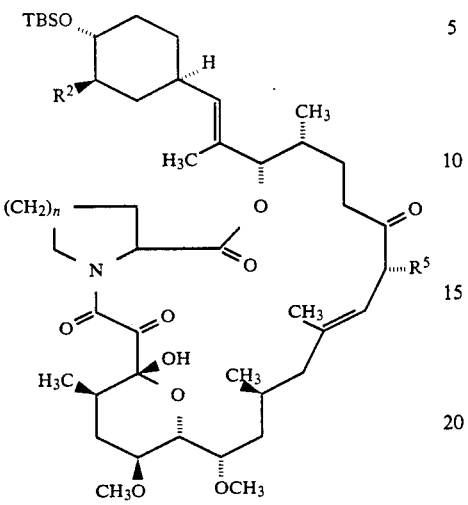
REACTION SCHEME J
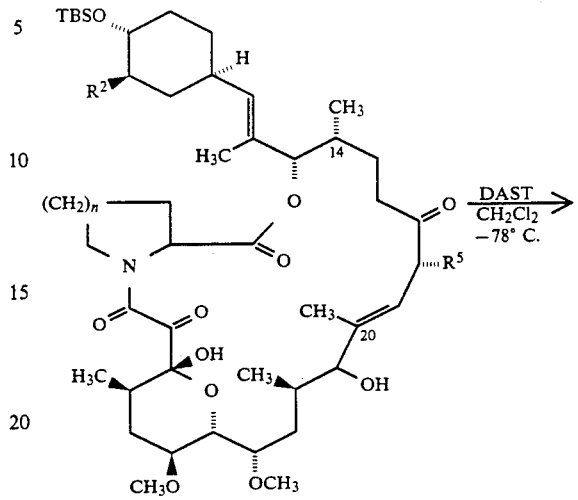
REACTION SCHEME I
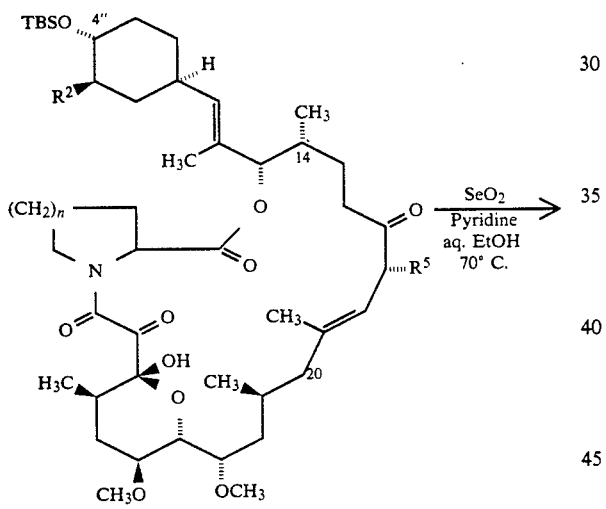
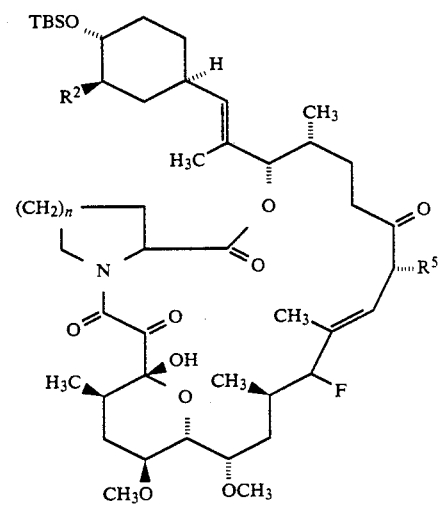
REACTION SCHEME K
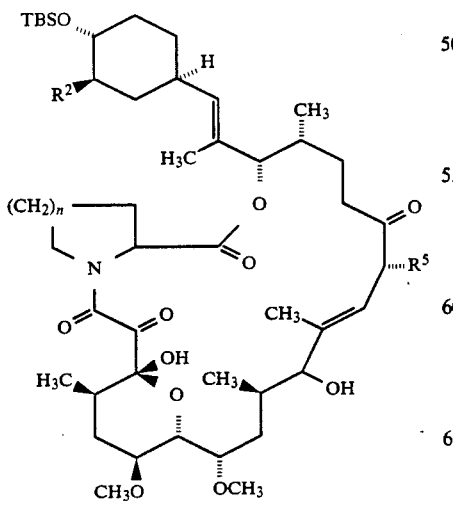
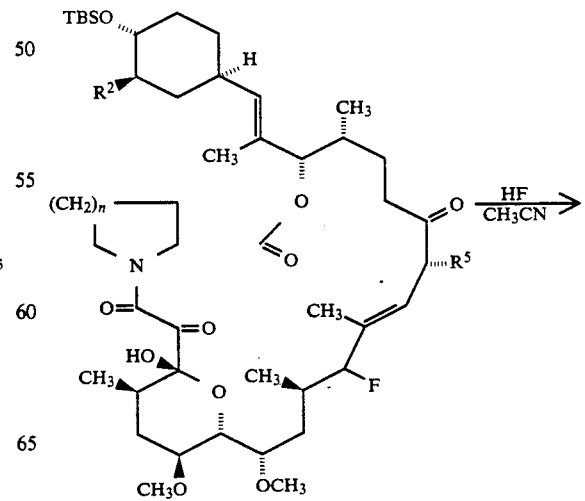

REACTION SCHEME K
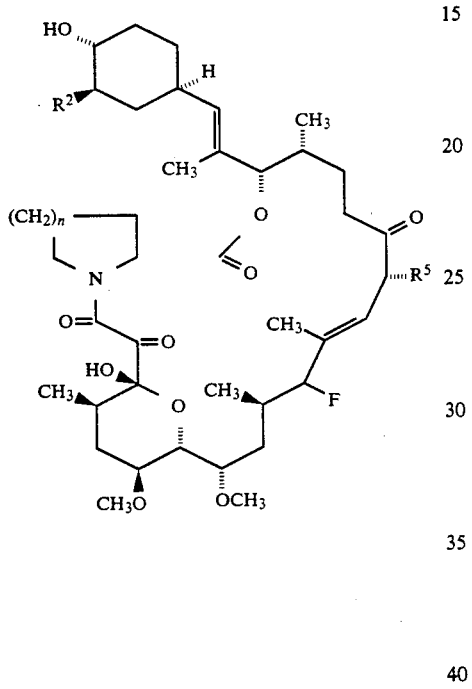
REACTION SCHEME L
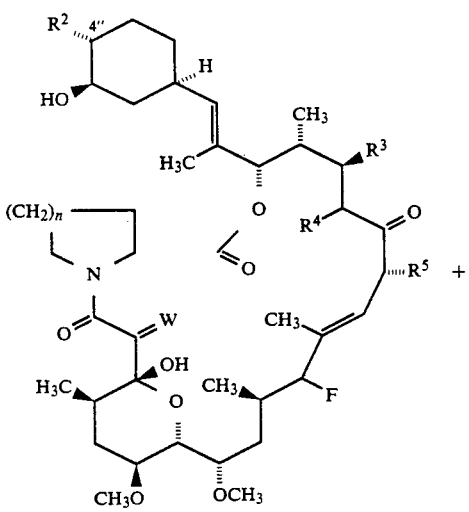
+
REACTION SCHEME L
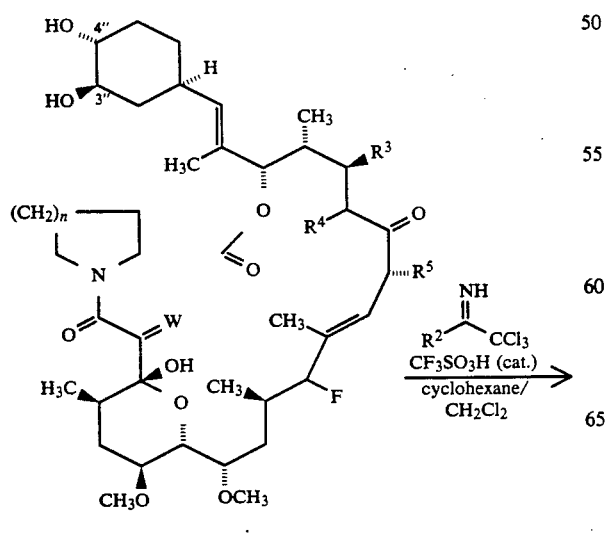
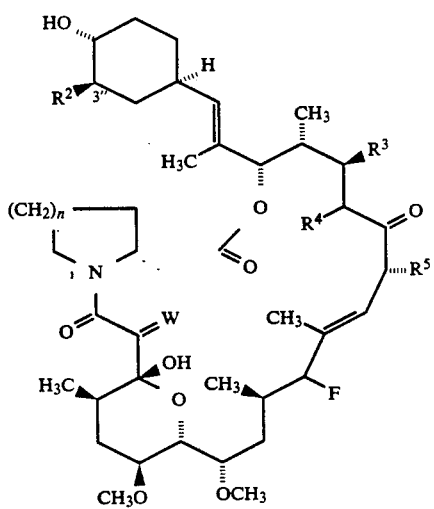

REACTION SCHEME M
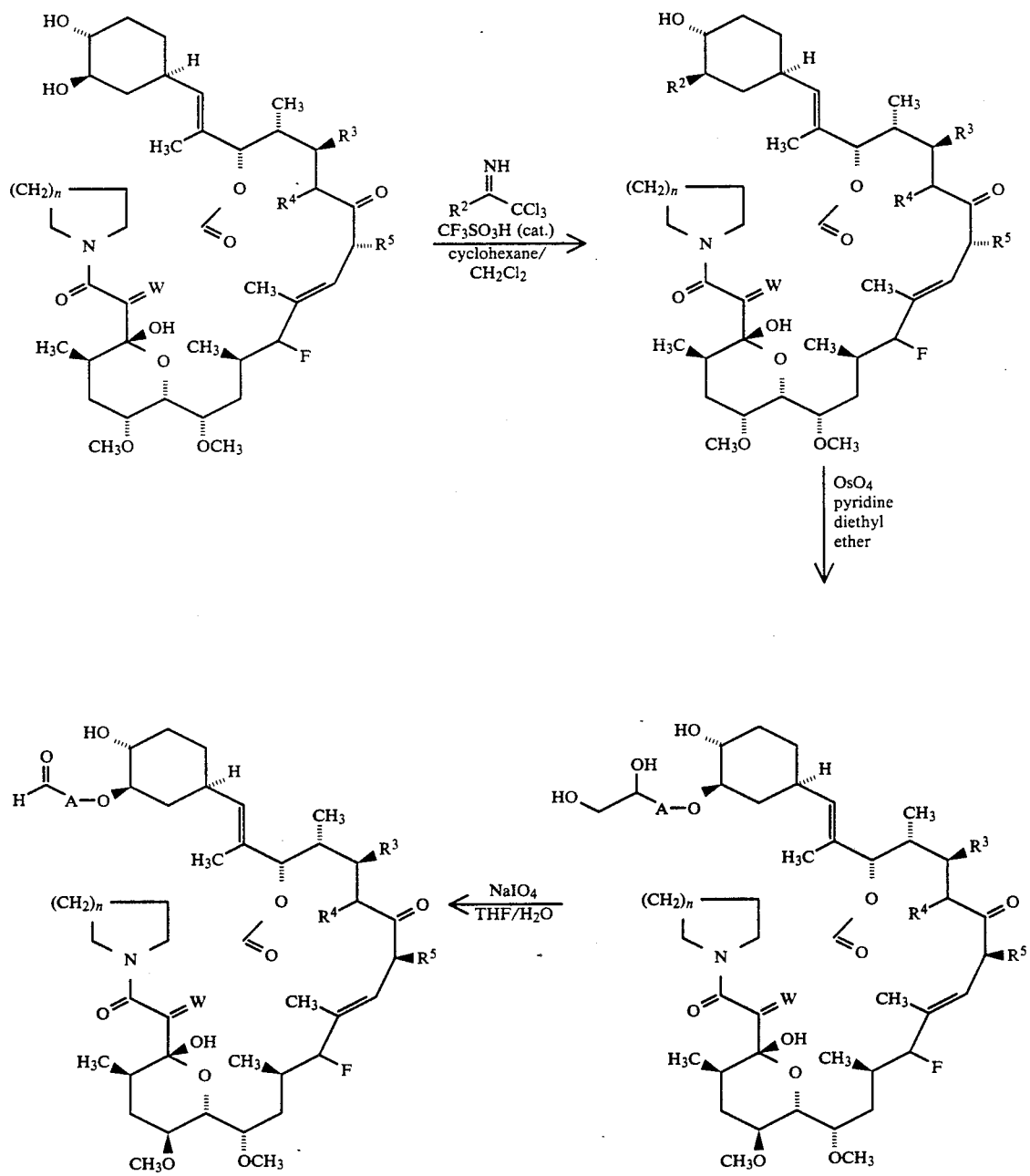

REACTION SCHEME N
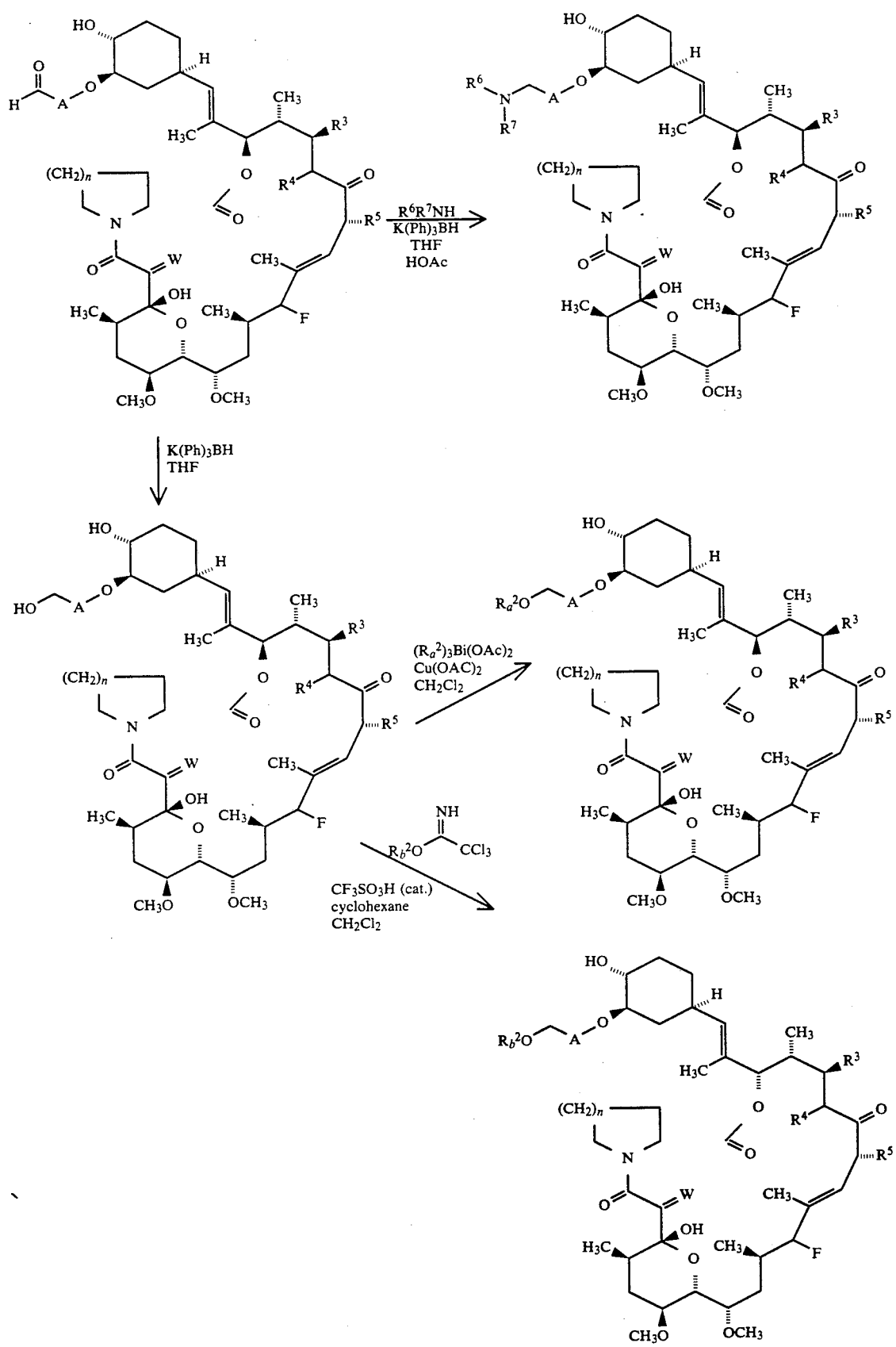

REACTION SCHEME O
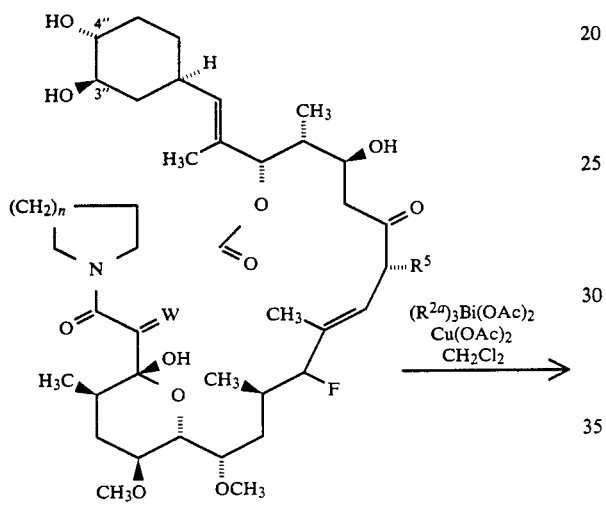
-continued
REACTION SCHEME O
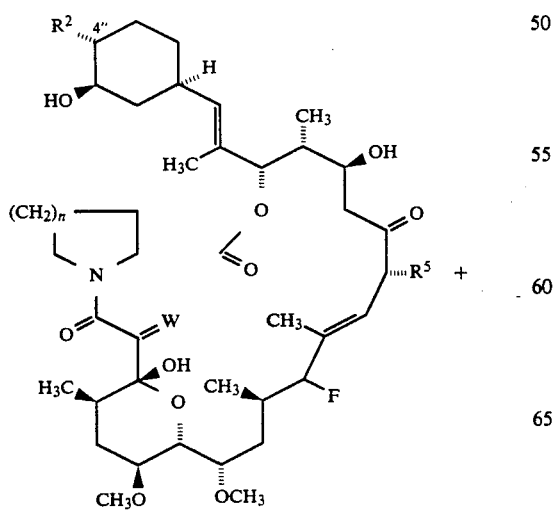      +      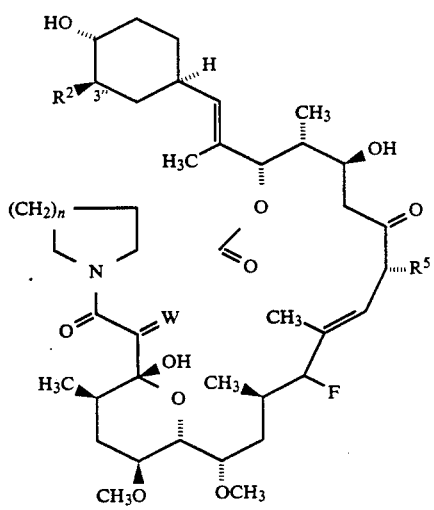

REACTION SCHEME P
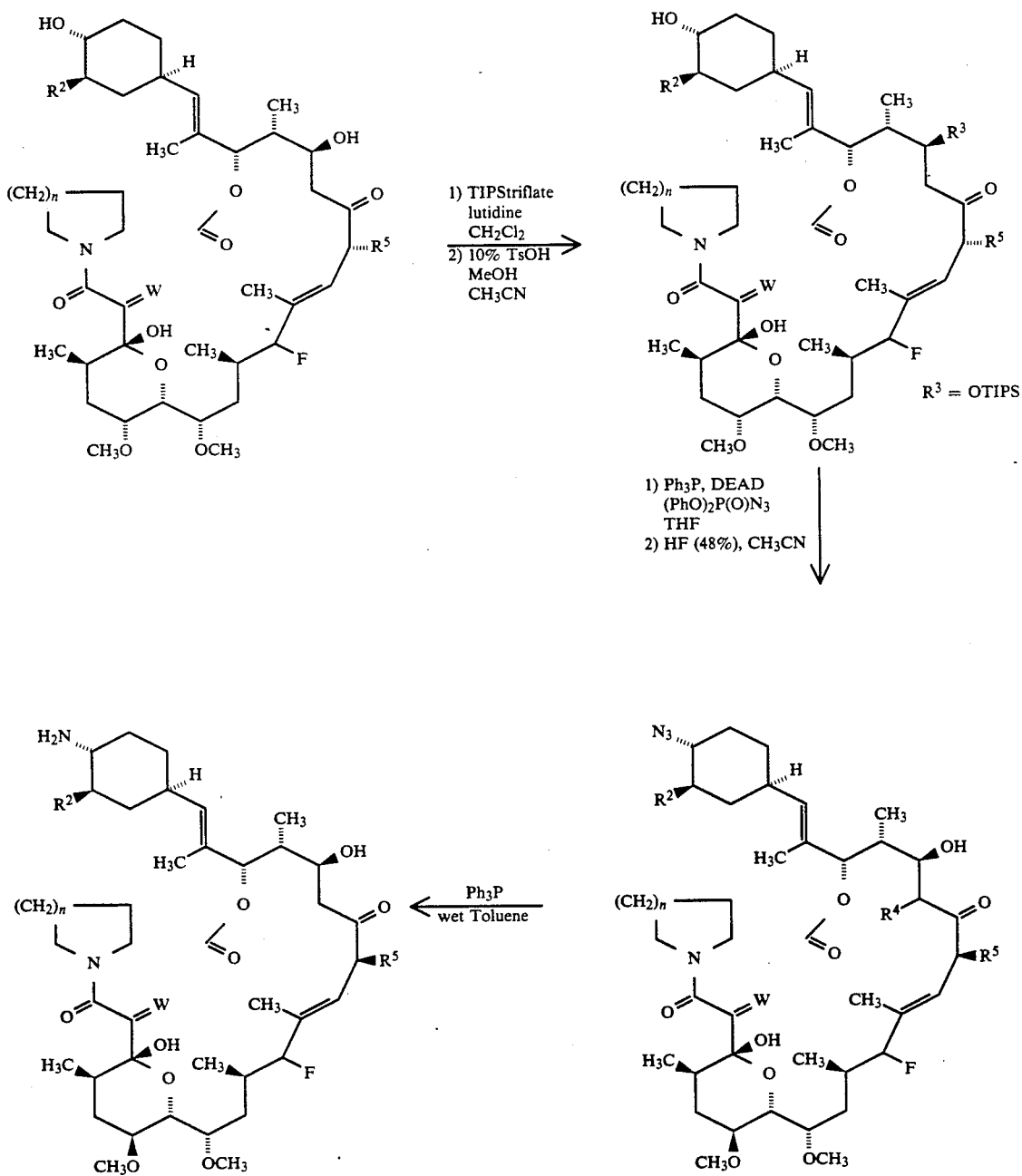

REACTION SCHEME Q
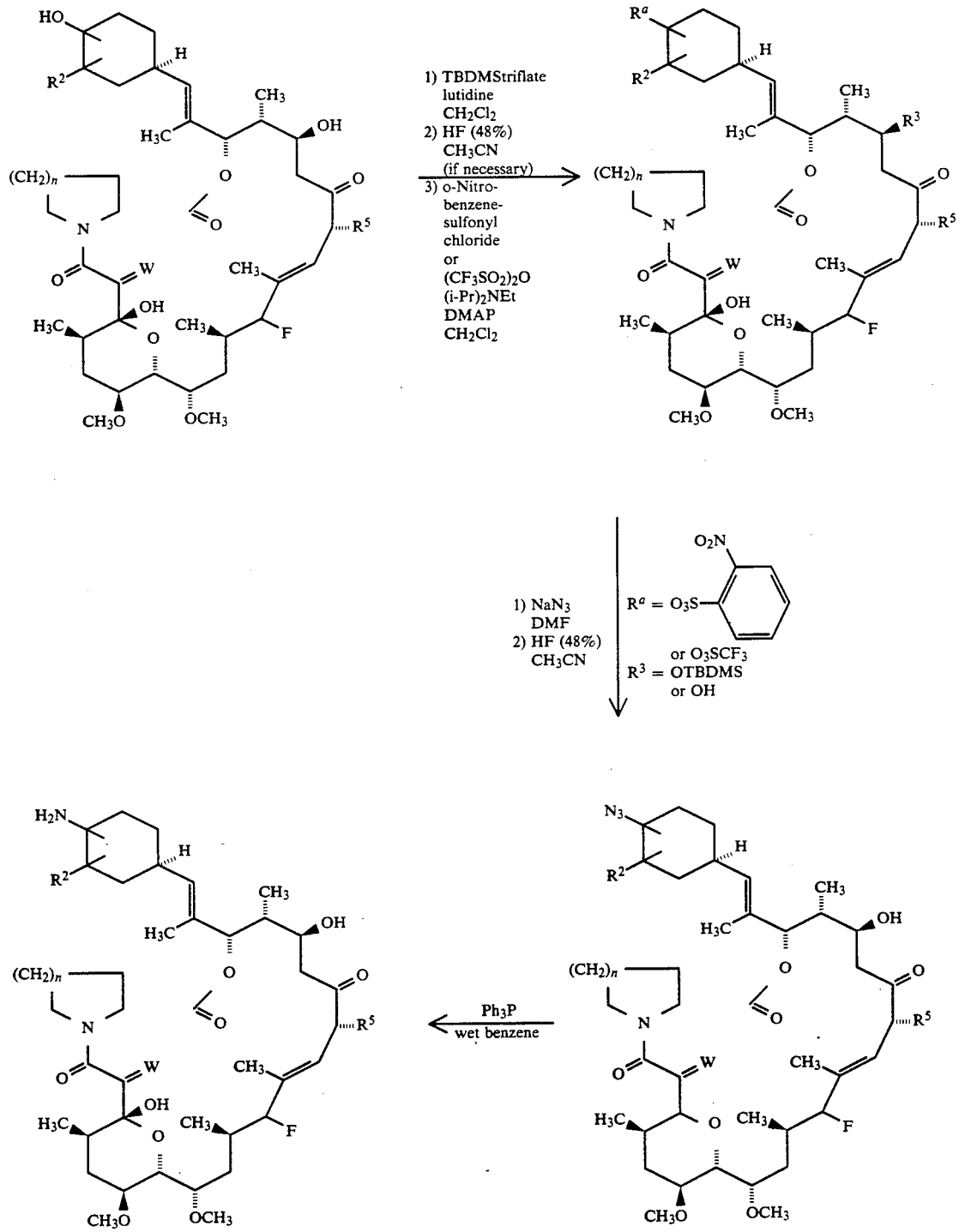

REACTION SCHEME R
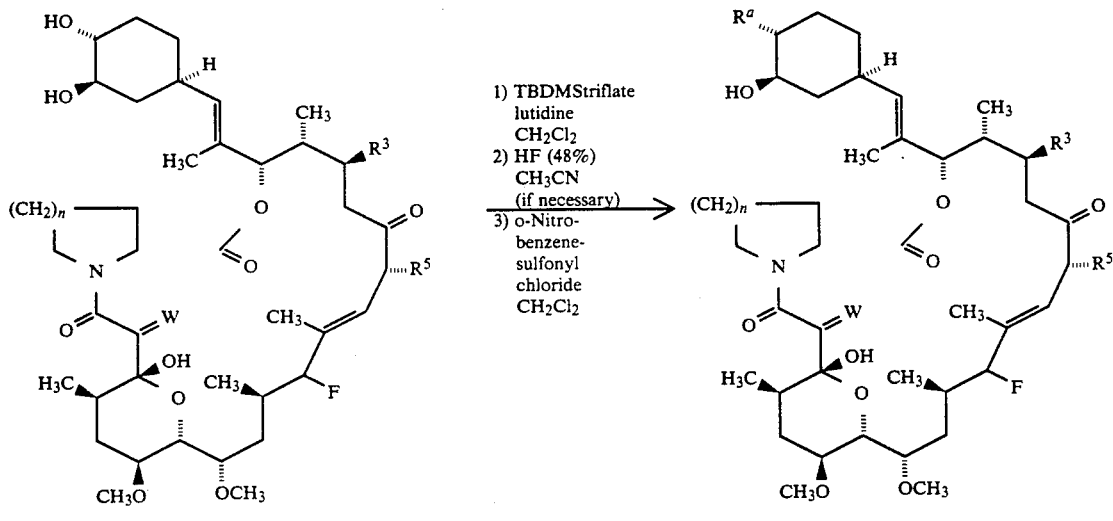
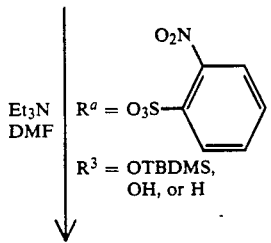
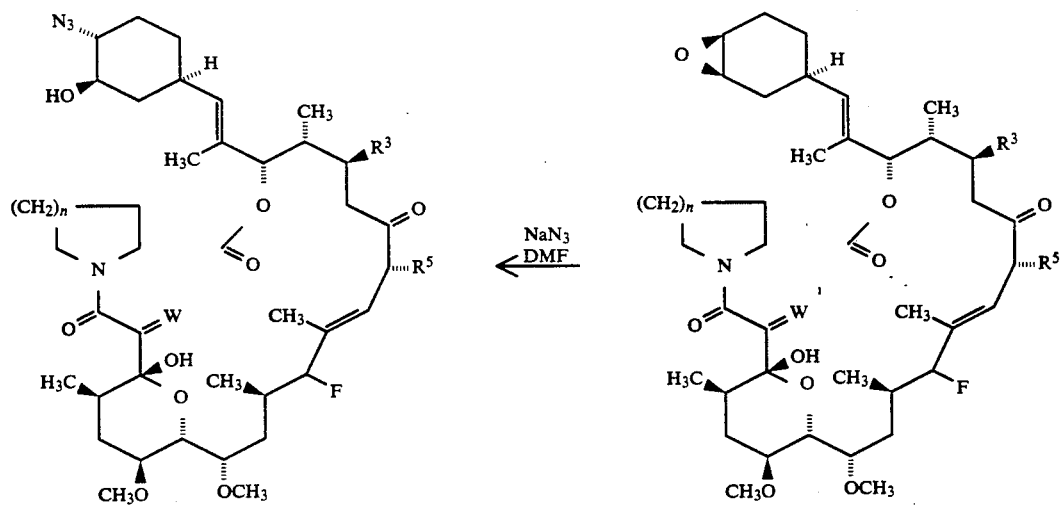

REACTION SCHEME S
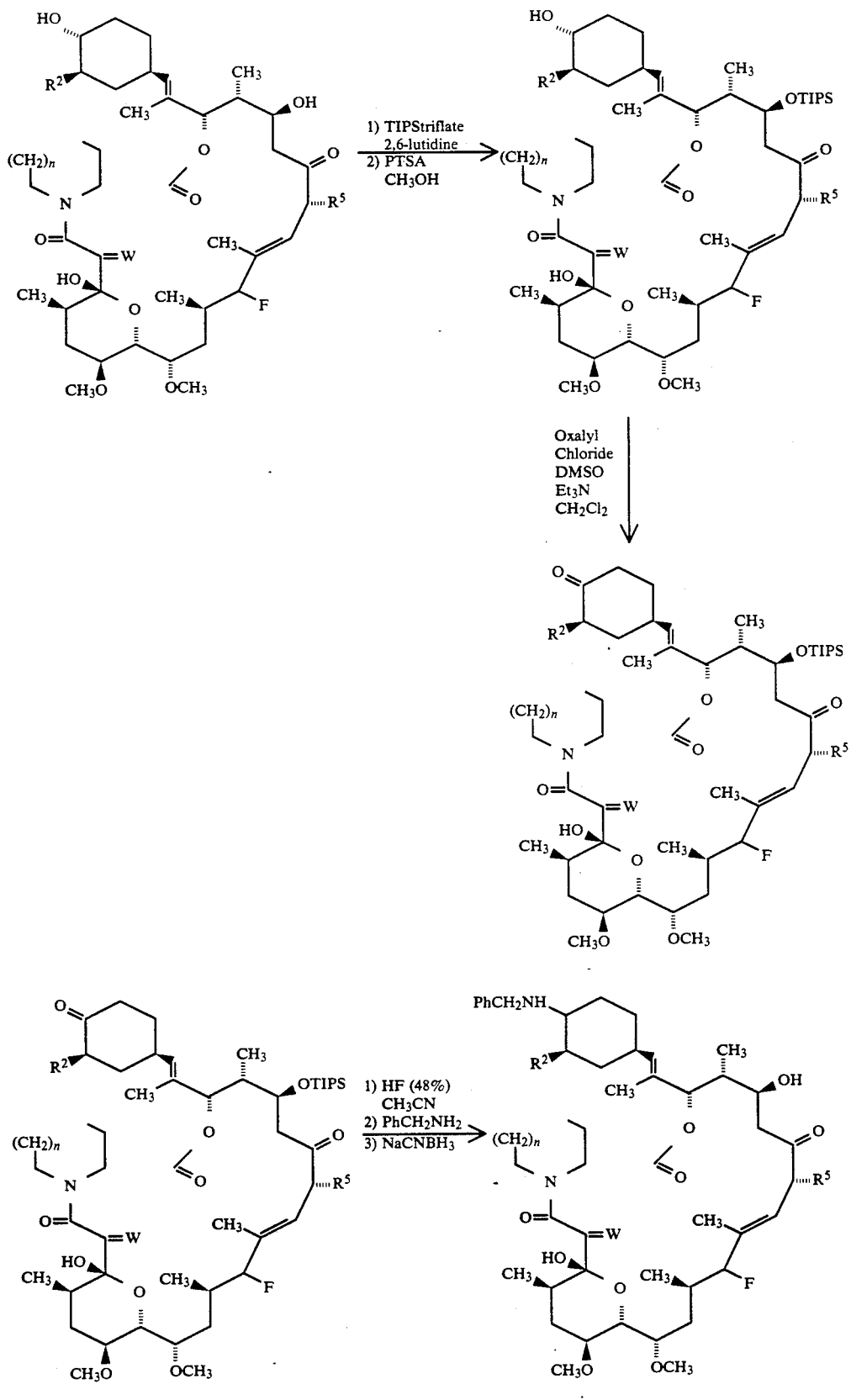

REACTION SCHEME T
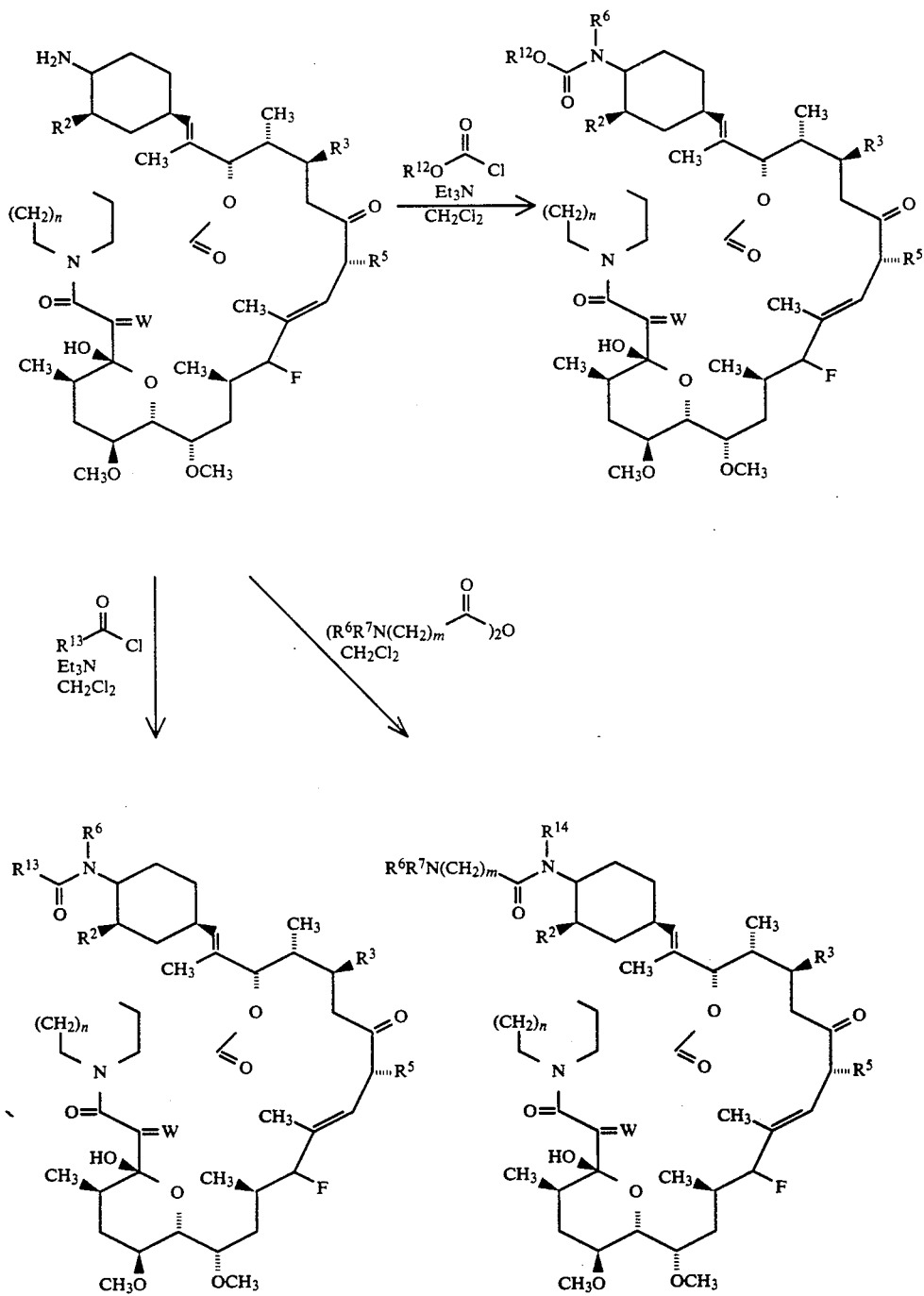

REACTION SCHEME U

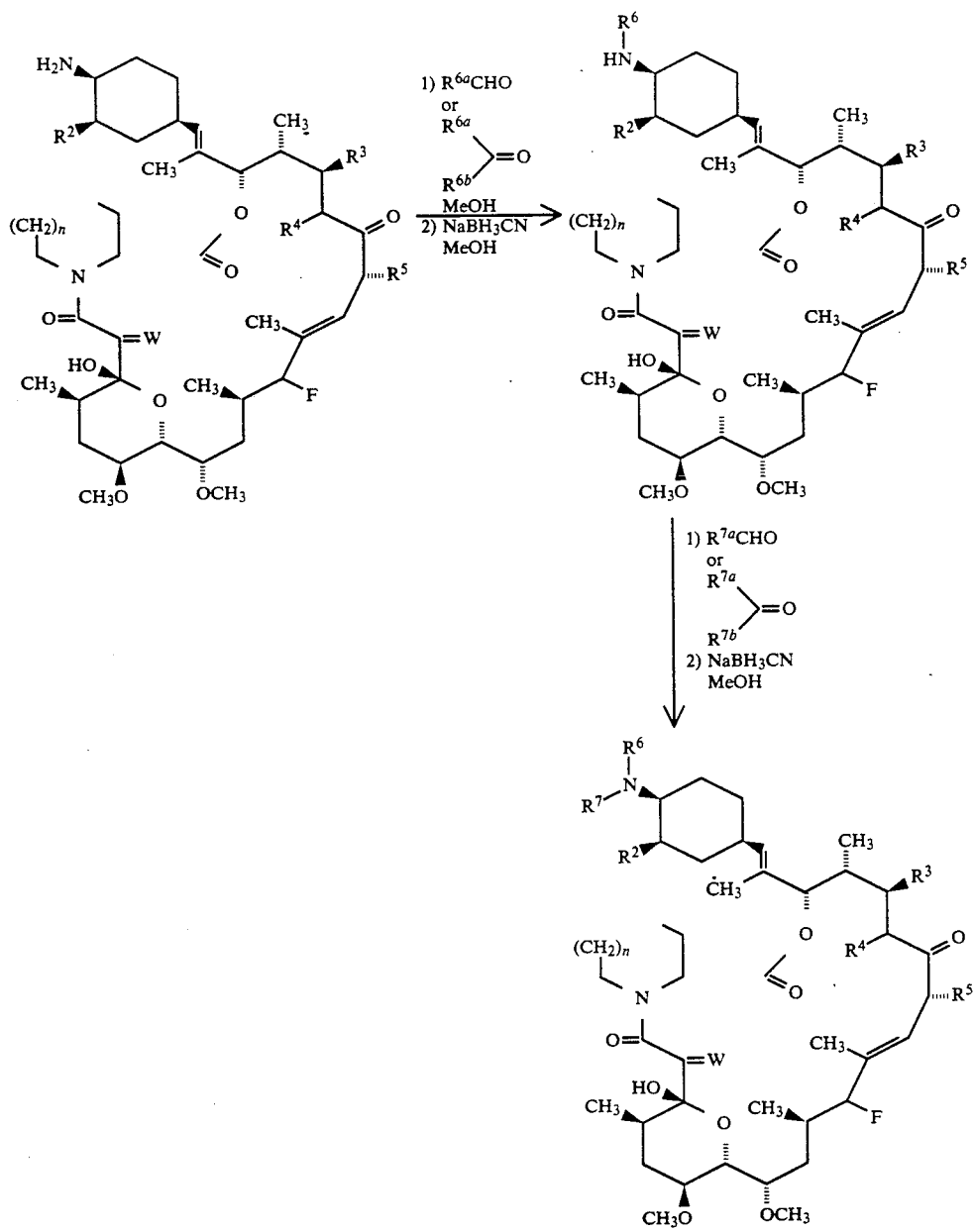

As shown in Reaction Scheme A the 4",14-dihydroxy macrolide is protected as the di(t-butyldimethylsilyl ether) by treatment with t-butyldimethylsilyl triflate in an inert organic solvent such as methylene chloride, chloroform or the like in the presence of a non-nucleophilic base such as 2,6-lutidine.

The diprotected macrolide is oxidized at C-20 as shown in Reaction Scheme B by treatment with selenium dioxide in an aqueous alcoholic solvent such as 95% ethanol in the presence of pyridine at solvent reflux temperature to give the 20-hydroxy macrolide.

As described in Reaction Scheme C treatment of the 20-hydroxy-4", 14-di-OTBS macrolide with diethylaminosulfur trifluoride in an inert organic solvent such as methylene chloride, chloride, chloroform or the like at a temperature of about 0° C. to −90° C., preferably about −78° C., gives the 20-fluoro-4", 14-di-OTBS macrolide. Removal of the silyl ether protecting groups (Reaction Scheme D) by treatment with hydrogen fluoride-pyridine complex in tetrahydrofuran gives the 20-fluoro-4", 14-dihydroxy macrolide. Reaction Schemes A-D may also be performed on the 3", 4", 14-trihydroxy macrolide to give the 20-fluoro-3", 4", 14-trihydroxy macrolide.

As shown in Reaction Scheme E the 14-hydroxy group of a macrolide (wherein $R^2$, $R^5$ and n are as defined above) may be eliminated by treatment with p-toluenesulfonic acid, benzenesulfonic acid, methanesulfonic acid, p-nitrobenzenesulfonic acid, p-bromobenzenesulfonic acid, p-chlorobenzenesulfonic acid, or p-methoxybenzenesulfonic acid, or mixtures thereof, in an inert organic solvent such as benzene, or toluene or the like at a temperature of 40° C. to solvent reflux temperature, preferably 60° C., for about 0.5 to 6 hours, or a sufficient period of time to eliminate the 14-hydroxy group. Neutralization with an aqueous solution of a weak base such as aqueous saturated sodium bicarbonate gives the aqueous saturated sodium bicarbonate gives the 14,15-dehydro macrolide. The 14-hydroxy group may also be eliminated by activation followed by basic elimination, as described in U.S. Pat. No. 4,894,366.

As shown in Reaction Scheme F the macrolide (wherein $R_a{}^3$ and $R_a{}^4$ taken together form a double bond) is reduced under an atmosphere of hydrogen in the presence of a noble metal catalyst, such as rhodium on carbon catalyst or rhodium on alumina catalyst, at a pressure of atmospheric pressure to a pressure of 40 psig, at or near room temperature in an organic solvent such as ethyl acetate or ethanol for about 1 to 24 hours, or until the requisite amount of hydrogen is absorbed to reduce the olefin(s) and give the reduced macrolide.

In Reaction Scheme G the macrolide (wherein $R_a{}^3$ and $R_a{}^4$ taken together form a double bond) is reduced with tri-n-butyltin hydride in the presence of tetrakis (triphenylphosphine)palladium(O) catalyst and acetic acid in an organic solvent such as toluene or tetrahydrofuran at or near room temperature for about 2 to 10 hours to give the reduced macrolide. By changing the sequence of synthesis steps, all possible variations in substitution may be obtained. For example, the C-14 hydroxyl can be eliminated and the resultant olefin reduced prior to the introduction of substituents at C-3" and/or C-4".

Protection of the C-3" and/or the C-4" hydroxyl group may be accomplished by methods known in prior art for compounds of Formula II such as by treatment with: 2,6-lutidine and triisopropylsilyl trifluoromethane sulfonate in a solution of methylene chloride; 2,6-lutidine and t-butyldimethylsilyl trifluoromethanesulfonate in a solution of methylene chloride; pyridine and acetic anhydride in a solution of methylene chloride; pyridine and benzoyl chloride in a solution of methylene chloride; pyridine and p-nitrobenzoyl chloride in a solution of methylene chloride; imidazole and t-butyldiphenylsilyl chloride in a solution of methylene chloride; and the like.

In a similar sequence of reactions the 14-deoxy 4"-hydroxy macrolide (or the 14-deoxy 3", 4", -dihydroxy macrolide) may be fluorinated at the 20-position. Protection of the 4"-hydroxy 14-deoxy macrolide as the t-butyldimethylsilyl ether is accomplished as shown in Reaction Scheme H by treatment with t-butyldimethylsilyl trifluoromethanesulfonate in an inert solvent such as methylene chloride, chloroform or the like in the presence of a non-nucleophilic base such as 2,6-lutidine.

The 14-deoxy 4"-OTBS macrolide is oxidized at the 20-position as shown in Reaction Scheme I by treatment with selenium dioxide in an aqueous alcoholic solvent such as 95% ethanol in the presence of pyridine at solvent reflux temperature to give the 20-hydroxy macrolide.

Incorporation of a fluoro substituent at C-20 is accomplished as shown in Reaction Scheme J by treatment of the 14-deoxy 20-hydroxy 4"-OTBS macrolide with diethylaminosulfur trifluoride in an inert organic solvent such as methylene chloride, chloroform or the like at a temperature of about 0° C. to −90° C., preferably about −78° C.

Removal of the t-butyldimethylsilyl protecting group as shown in Reaction Scheme K by treatment with hydrogen fluoride in acetonitrile gives the 14-deoxy 20-fluoro-4"-hydroxy macrolide.

As shown in Reaction Scheme L, (wherein $R^2$ is alkoxy, substituted alkoxy, alkenyloxy, substituted alkenyloxy, alkynyloxy or substituted alkynyloxy) a solution of the 3", 4"-dihydroxy macrolide in an inert organic solvent such as methylene chloride, chloroform, pentane, hexane, cyclohexane, heptane or the like or mixtures thereof is treated with a trichloroacetimidate (prepared by the reaction of an appropriate sodium alkoxide with trichloroacetonitrile, such as described by Wessel, H. P., Inversen, T., Bundle, D. R., *J. Chem. Soc., Perkins Trans, I,* 1985, 2247) in the presence of a mild acid catalyst such as trifluoromethanesulfonic acid, p-toluenesulfonic acid, methanesulfonic acid, benzenesulfonic acid, p-nitrobenzenesulfonic acid, p-bromobenzenesulfonic acid, p-chlorobenzenesulfonic acid, or p-methoxybenzenesulfonic acid, or mixtures thereof at a temperature of 20°-50° C., preferably 25° C., for a period of one hour to seven days, preferably 6 hours, to give a mixture of the 3"-O-alkyl, -alkenyl or -alkynyl 4"-hydroxy macrolide and the 3"-hydroxy 4"-O-alkyl, -alkenyl or -alkynyl macrolide.

As shown in Reaction Scheme M, the 3",4"-dihydroxy macrolide (wherein $R^3$ is protected hydroxy or hydrogen) may be reacted with an alkenyl trichloroacetimidate (wherein $R^2$ is $C_{3-8}$ alkenyl) under conditions described in Reaction Scheme E to give the C-3"-O-alkenyl macrolide. Treatment with a stochiometric amount of osmium tetraoxide in an inert organic solvent, such or tetrahydrofuran, in the presence of an amine base, such as pyridine at or near room temperature gives the corresponding glycol. Treatment with sodium metaperiodate in a solution of tetrahydrofuran/water gives the aldehyde. Alternatively, the C-3"-O-alkenyl macrolide may be treated with sodium metaperiodate in the presence of a catalytic amount of osmium tetraoxide in an organic solvent to give the aldehyde directly. In an analogous manner, the C-4"-derivatives may also be prepared.

A variety of compounds may be prepared from the corresponding aldehyde as illustrated in Reaction Scheme N. The aldehyde may be reacted with a primary or secondary amine (wherein $R^6$ and $R^7$ are as defined above) in an organic solvent such as tetrahydrofuran to give an imine which is reduced in situ with a hydride reducing agent, such as potassium triphenyl borohydride or sodium cyanoborohydride, to give the macrolide bearing an amino alkoxy functionality at C-3". The aldehyde may also be reduced to the corresponding alcohol by treatment with a hydride reducing agent, such as potassium triphenyl borohydride or sodium cyanoborohydride in an organic solvent such as tetrahydrofuran. The alcohol may be further modified by utilizing the methods of Reaction Scheme N (wherein $R_b{}^2$ is unsubstituted or substituted alkyl, alkenyl or alkynyl) or by treatment with a triarylbismuth diacetate reagent (wherein $R_a{}^2$ is aryl or substituted aryl) (prepared immediately prior to use by the addition of acetic acid to a suspension of a triarylbismuth carbonate in an inert organic solvent such as methylene chloride, chloroform or the like or mixtures thereof) in the presence of a catalytic amount of copper(II) acetate at a temperature of 20°-50° C., preferably room temperature, for a period of one hour to seven days, preferably one day, to give the desired macrolide. Alternatively, the triarylbismuth(V) reagent can be prepared by treatment of a triarylbismuthine with a suitable oxidant such as peracetic acid, iodobenzene diacetate, bis(trifluoroacetoxy)iodobenzene and the like in an inert solvent such as methylene chloride, chloroform, benzene, toluene and the like. The triarylbismuth(V) reagent can be used without purification or can be purified by silica gel chromatography. Triarylbismuthines may be prepared by the reaction of an appropriate aryl Grignard reagent with bismuth trichloride in an inert organic solvent such as tetrahydrofuran, diethyl ether, or 1,4-dioxane, or mixtures thereof, at or near room temperature for a period of 1 to 48 hours. General procedures for the preparation and use of triaryl bismuth reagents may be found in Barton, D. H. E., et al., *J. Chem. Soc. Chem. Commun.*, 1986, 65 and references cited therein. The procedures described in Reaction Scheme N are readily applicable to the preparation of compounds bearing an ether functionality at C-4".

As shown in Reaction Scheme O, a solution of the 3",4"-dihydroxy macrolide in an inert organic solvent such as methylene chloride, benzene, toluene, chloroform, or the like or mixtures thereof is treated with a triarylbismuth diacetate reagent (wherein $R^{2a}$ is $R^2O$—) in the presence of a catalytic amount of copper(II) acetate at a temperature of 20°–50° C., preferably room temperature, for a period of one hour to seven days, preferably one day, to give a mixture of the 4"-O-aryl 3"-hydroxy macrolide and the 3"-O-aryl-4"-hydroxy macrolide. Alternatively, the triarylbismuth(V) reagent can be prepared by treatment of a triarylbismuthine with a suitable oxidant such as peracetic acid, iodobenzene diacetate, bis(trifluoroacetoxy)iodobenzene and the like in an inert solvent such as methylene chloride, chloroform, benzene, toluene and the like. The 4"-O-aryl-3"-hydroxy macrolide and the 3"-O-aryl-4"-hydroxy macrolide may be separated and purified in a conventional manner, for example, fractional crystallization, recrystallization, chromatography, and the like.

As shown in Reaction Scheme P the C-14-OTIPS protected macrolide is prepared from the 4",14-dihydroxy macrolide and reacted with diphenyl phosphoryl azide in the presence of triphenyl phosphine and diethyl azodicarboxylate to introduce the azide substituent at the C-4" position. The protecting group at C-14 is removed and reduction of the azide with triphenylphosphine/water gives the C-4" amino compound.

An alternate route to C-3"/C-4" amino substituted compounds is shown in Reaction Scheme Q. The macrolide is protected if necessary and reacted with o-nitrobenzenesulfonyl chloride or trifluoromethanesulfonyl anhydride in the presence of an amine base to give the mono- C-3"/C-4" o-nitrobenzenesulfonyl or trifluoromethanesulfonyl derivative. The activated leaving group is displaced by treatment with sodium azide (or an alternative nucleophilic amine), the protecting group is removed, if necessary, by treatment with hydrogen fluoride and, if necessary, the azide is reduced with triphenyl phosphine/water to give the amino compound. Azides can be reduced with other reagents known in the art, such as with hydrogen sulfide, propane-1,3-dithol, or thioacetic acid or by catalytic hydrogenation over a suitable catalyst.

As shown in Reaction Scheme R, the opposite stereochemistry of the resultant amino compound can be obtained by proceeding through an epoxide as a synthetic intermediate. Reaction of the C-3"-beta, C-4"-alpha dihydroxy macrolide (wherein $R^3$ is hydrogen or protected hydroxy) with o-nitrobenzenesulfonyl chloride followed by separation of the isomers and treatment with a tertiary amine base, such as triethylamine, gives the two possible epoxides. The beta-epoxide may be opened by treatment with azide to give the C-3"-beta-hydroxy C-4"-alpha-azido macrolide. The C-3"-hydroxy group may be modified to form the aryl, alkyl, alkenyl or alkynyl ether, prior to reduction of the azide to the amine (by the methods of Reaction Scheme N), and the resultant amine may be further modified by methods described in Reaction Scheme T.

An amino substituent may also be introduced at C-4" by reductive amination of a keto-substituted macrolide as shown in Reaction Scheme S. The ketone at C-4" is prepared by Swern oxidation of a suitably protected hydroxy-macrolide. Reductive amination of the ketone with an appropriate amine gives the corresponding amino-macrolide as a mixture of epimers at C-4".

Compounds bearing a C-4" amino substituent may be further modified by methods which are known in the art as exemplified in Reaction Scheme T. These methods include, but are not limited to such methods as: acylation with an appropriate acid halide or acid anhydride in the presence of an amine base to give the corresponding amide, coupling with an appropriate carboxylic acid to give the corresponding amide, reaction with an isocyanate to give the urea derivative, treatment with an ethyl chloroformate equivalent to give the corresponding urethane or alkylation with an appropriate alkyl halide to give the corresponding secondary, tertiary or quarternary alkyl amine.

An amino substituent may also be modified at C-3" and/or C-4" by reductive amination of an amino-substituted macrolide as shown in Reaction Scheme U (wherein $R^{6a}$ or $R^{6b}$ and $R^{7a}$ or $R^{7b}$ are respectively equivalent to $R^6$ and $R^7$ absent one methylene group). The imine is prepared by reaction of the amine with an appropriate aldehyde or ketone. Reduction of the imine with sodium cyanoborohydride or similar reducing agent gives the corresponding aminomacrolide. The reductive amination may be repeated to give mixed-disubstituted amino macrolides.

The procedures described in Reaction Schemes L-U may optionally be conducted prior to the procedures of Reaction Schemes A-14 D and H-K. Additionally, the procedures described in Reaction Schemes E-G may be conducted subsequent to the procedures of Reaction Schemes L-U. In general, however, it is preferred that the fluoro group be introduced prior to the introduction of additional functionality.

The object compounds of Formula I obtained according to the reactions as explained above can be isolated and purified in a conventional manner, for example, extraction, precipitation, fractional crystallization, recrystallization, chromatography, and the like.

It is to be noted that in the aforementioned reactions and the post-treatment of the reaction mixture therein, the stereoisomer(s) of starting and object compounds due to asymmetric carbon atom(s) or double bond(s) of the object compounds of Formula I may occasionally be transformed into the other stereoisomer(s), and such cases are also included within the scope of the present invention.

In the present invention, compounds with asymmetric centers may occur as racemates, diastereomeric mixtures and as individual diastereomers, with all isomeric forms of the compounds being included in the present invention. These may be prepared by methods such as those disclosed in publications which describe synthetic routes to fragments of the macrolide FR- 900506 and the total synthesis of the macrolide FR-900506 itself (see for example, *J. Am. Chem. Soc.* 1989, 111, 1157; *J. Am. Chem. Soc.* 1990, 112, 2998; *J. Org. Chem.* 1990, 55, 2786; *J. Am. Chem. Soc.* 1990, 112, 5583. *Tetrahedron Lett.* 1988, 29, 277; *Tetrahedron Lett.* 1988, 29, 281; *Tetrahedron Lett.* 1988, 29, 3895; *J. Org. Chem.* 1988, 53, 4643; *Tetrahedron Lett.* 1988, 29, 4245; *Tetrahedron Lett.* 1988, 29, 4481; *J. Org. Chem.* 1989, 54, 9; *J. Org. Chem.* 1989, 54, 11; *J. Org. Chem.* 1989, 54, 12; *J. Org. Chem.* 1989, 54, 15; *J. Org. Chem.* 1989, 54, 17; *Tetrahedron Lett.* 1989, 30, 919; *Tetrahedron Lett.* 1989, 30, 1037; *J. Org. Chem.* 1939, 30, 5235; *Tetrahedron Lett.* 1989, 30, 6611; *Tetrahedron Lett.* 1989, 30, 6963; *Synlett* 1990, 38; *J. Org. Chem.* 1990, 55, 2284; *J. Org. Chem.* 1990, 55, 2771; *J. Org. Chem.* 1990, 55, 2776; *Tetrahedron Lett.* 1990, 31, 1439; *Tetrahedron Lett.* 1990, 31, 1443; *Tetrahedron Lett.* 1990, 31, 3007; *Tetrahedron Lett.* 1990, 31, 3283, 3287).

The compounds of the present invention are capable of forming salts with various inorganic and organic acids and bases and such salts are also within the scope of this invention. Examples of such acid addition salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, lactate, maleate, methanesulfonate, 2-naphthalenesulfonate, oxalate, pamoate, persulfate, picrate, pivalate, propioate, succinate, tartrate, toluenesulfonate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine and so forth. Also, the basic nitrogen-containing groups may be quaternized with such agents as: lower alkyl halides, such as methyl, ethyl, propyl, and butyl chloride, bromides and iodides; dialkyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

C. Utility of the compounds within the scope of the invention

The compounds of Formula I may be employed as immunosuppressants or antimicrobial compounds by methods and in dosages known in the prior art for compounds of Formula II. These compounds possess pharmacological activity such as immunosuppressive activity, antimicrobial activity, and the like, and therefor are useful for the treatment and prevention of the resistance to transplantation or transplantation rejection of organs or tissues such as heart, kidney, liver, duodenum, small-bowel, medulla ossium, skin, pancreatic islet-cell, etc., graft-versus-host diseases by medulla ossium transplantation, autoimmune diseases such as rheumatoid arthritis, systemic lupus erythematosis, Hashimoto's thyroiditis, multiple sclerosis, myasthenia gravis, type I diabetes, uveitis, allergic encephalomyelitis, glomerulonephritis, etc., and infectious diseases caused by pathogenic microorganisms.

The compounds of Formula I are also useful for treating inflammatory and hyperproliferative skin diseases and cutaneous manifestations of immunologically-mediated illnesses such as: psoriasis, atopical dermatitiis, contact dermatitis and further exzematous dermatitises, seborrhoeic dermatitis, *Lichen planus,* Pemphigus, bullous Pemphigoid, *Epidermolysis bullosa,* urticaria, angioedemas, vasculitides, erythemas, cutaneous eosinophilias or *Alopecia areata.* More particularly, the compounds of Formula I are useful in hair revitalizing, such as in the treatment of male pattern alopecia or alopecia senilis, by providing epilation prevention, hair germination, and/or a promotion of hair generation and hair growth.

The compounds of Formula I are further useful for treating reversible obstructive airways disease, including conditions such as asthma, including bronchial asthma, allergic asthma, intrinsic asthma, extrinsic asthma and dust asthma, particularly chronic or inveterate asthma (for example late asthma and airway hyperresponsiveness), bronchitis and the like. The compounds of Formula I may also be useful for treating hepatic injury associated with ischemia.

The compounds of Formula I may also act as antagonists of macrocyclic immunosuppressive compounds, including derivatives of 12-(2'-cyclohexyl-1'-methylvinyl)-13,19,21,27-tetramethyl-11,28-dioxa-4-azatricyclo[22.3.1.0$^{4,9}$]octacos-18-ene, and so be useful in the treatment of immunodepression (such as AIDS, cancer, senile dementia, trauma (including wound healing, surgery and shock), chronic bacterial infection and certain central nervous system disorders), overdosages or toxicity of such immunosuppressive compounds, and as an adjunct to the administration of an antigen in vaccination.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. For example, the compounds of Formula I may be utilized with hydroxypropyl methylcellulose essentially as described in U.S. Pat. No. 4,916,138, issued Apr. 10, 1900, or with a surfactant essentially as described in EPO Publication 0,428,169. Oral dosage forms may be prepared essentially as described by T. Hondo, et al., *Transplantation Proceedings,* 1987, XIX, Supp. 6, 17–22. Dosage forms for external application may be prepared essentially as described in EPO Publication 0,423,714. The active object compound is included in the pharmaceutical composition in an amount sufficient to produce the desired effect upon the process or condition of diseases.

For the treatment of these conditions and diseases caused by immunoirregularity a compound of Formula I may be administered orally, topically, parenterally, by inhalation spray or rectally in dosage unit formulations containing conventional non-toxic pharmaceutically acceptable carriers, adjuvant and vehicles. The term parenteral as used herein includes subcutaneous injections, intravenous, intramuscular, intrasternal injection or infusion techniques.

For modifying the activity and/or toxicity of FK-506-type immunosuppressants, a compound of Formula I may be administered prior to, in conjunction with or subsequent to the administration FK-506-type of a compound.

Dosage levels of the compounds of the present invention are of the order from about 0.01 mg to about 50 mg per kilogram of body weight per day, preferably from about 0.1 mg to about 10 mg per kilogram of body weight per day, are useful in the treatment of the above-indicated conditions (from about 0.7 mg to about 3.5 mg per patient per day, assuming a 70 kg patient). In addition, the compounds of the present invention may be administered on an intermittent basis; i.e. at semi-weekly, weekly, semi-monthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain from about 0.5 mg to about 500 mg of active ingredient. For external administration the compound of Formula I may be formulated within the range of, for example, 0.0001% to 60% by weight, preferably from 0.001 to 10% by weight, and most preferably from about 0.005 to 0.8% by weight.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitation on the scope or spirit of the instant invention.

EXAMPLE 1

17-Ethyl-1-hydroxy-12-[2'-(4"'-(tert-butyldimet hylsilyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4"'-hydroxy-3"-methoxycyclohexyl)-1'-methylvinyl]-23,25-dimethoxy-13,19,21,-27-tetramethyl-11,28-dioxa-4-aza-tricyclo[22.3.1.0$^{4,9}$]octacos-18-ene-2,3,10,16-tetraone (200 mg) in dry methylene chloride (3 ml) was added in excess of 2,6-lutidine (45 μl) and the mixture was stirred at room temperature. After 10 minutes, tert-butyldimethylsilyl trifluoromethanesulfonate (64 μl) was added by syringe. After 15 minutes the reaction mixture was diluted with ethyl acetate, extracted from saturated bicarbonate, washed with brine and the organic phase dried over magnesium sulfate. Removal of solvent in vacuo and flash chromatography on silica gel (ethyl acetate: hexane (1:2)+1% methanol) gave the title compound (235 mg).

($^1$H NMR consistent with the desired structure).

EXAMPLE 2A

17-Ethyl-1,20-dihydroxy-12-[2'-(4"'-tert-buty ldimethylsilyloxy)-3"-methoxycyclohexyl)-4"'1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of 17-ethyl-1-hydroxy-12-[2'-(4"'-(tert-butyldimethylisilyloxy)-3"-methoxycyclohexyl)-'-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (235 mg) in 95% ethanol (2.2 ml) was added 53 μl of pyridine followed by selenium dioxide (58 mg). The flask was fitted with a water condenser and heated to 70° C. on a mantle. After 20 hours the mixture was cooled to room temperature filtered through diatomaceous earth and the filtrate poured into a saturated sodium bicarbonate solution. This was extracted with ethyl acetate, washed with brine and dried over magnesium sulfate. The solution was concentrated and purified by flash chromatography on silica gel (ethyl acetate: hexane (1:2)+1% methanol) to give the title compound (89 mg).

($^1$H NMR consistent with the desired structure).

EXAMPLE 2B

17-Ethyl-1,14,20-trihydroxy-12-[2'-(4"'-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"'-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (5.15 gm, 0.065 mol) in glacial acetic acid (500 ml) at room temperature, was added a solution of selenium dioxide (9.27 gm, 0.083 mol) in H$_2$O (90 ml). The reaction mixture was stirred at room temperature for 41 hours whereupon, it was poured into a stirred mixture of H$_2$O (3 L) and celite. After stirring for 15 minutes, the mixture was filtered through a pad of celite and extracted with diethyl ether (1×2 L, 2×1 L). The organic fractions were washed with saturated sodium bicarbonate and brine, dried over magnesium sulfate, filtrated and evaporated in vacuo. The product was purified by chromatography (silica, acetone:hexanes 2:5) to give the title compound. MASS and $^1$H NMR were consistent with the structure.

EXAMPLE 3

17-Ethyl-20-fluoro-1-hydroxy-12-[2'-(4"'-(tert-b utyldimethylsiloxy)-3"-methoxycyclohexyl)-1'-methyl-vinyl]-23,25-dimethoxy-13,19,21,27-tetramethyl-11,28-dioxa-4-azatricyclo[22.3.1.0$^{4,9}$]octacos-18-ene-2,3,10.16-tetraone A solution of 17-ethyl-20-dihydroxy-12-[2'-(4"'-(tert-butyldimethylsiloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10.16-tetraone (30.5 mg) in methylene chloride (0.5 ml) was cooled to −78° C. in a dry ice/isopropanol bath. To this stirred solution, diethylaminosulfur trifluoride (4.5 µl) was added. After 3 minutes, saturated sodium bicarbonate (500 µl) was added followed by ethyl acetate (2 ml) and the mixture was warmed to room temperature. Extraction from ethyl acetate, drying over magnesium sulfate and purification by flash chromatography on silica gel (ethyl acetate: hexane (1:2)+1% MeOH) gave the title compound (22 mg).

($^1$H NMR consistent with the desired structure).

EXAMPLE 4

17-Ethyl-20-fluoro-1-hydroxy-12-[2'-(4''-(hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-20-fluoro-1-hydroxy-12-[2'-(4''-(tert-butyldimethylsiloxy)-3''-methoxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10.16-tetraone (7 mg) in acetonitrile (0.3 ml) was added a solution of 2% hydrogen fluoride in aqueous acetonitrile (100 µl), and the mixture stirred at room temperature. After 2 hours the solution was diluted with ethyl acetate, extracted with saturated sodium bicarbonate and the organic phase dried by passage through a magnesium sulfate column. Purification of the concentrate by flash chromatography on silica gel (ethyl acetate: hexane (1:1)+1% methanol) gave the title compound.

MASS: (FAB) 816 (M+Na).

partial $^{13}$C NMR δ: 211.5 (C-16); 196.1 (2) 169.3 (10); 165.0 (3); 138.1 (C-19); 135.8 (C-1'); 121.0 (C-18' major); 84.1 (C-3''); 43.1 (C-15); 26.0 (C-21).

EXAMPLE 5

17-Ethyl-1-hydroxy-14-(tert-butyldimethylsiloxy)-12-[2'-(4''-(tert-butyldimethylsilyloxy)-3''-methoxycyclohexyl)-1'-methylvinyl[-23,25-dimethoxy-13,19,21,27-tetramethyl-11,28-dioxa-4-azatricyclo[22.3.1.0$^{4,9}$]octacos-18-ene-2,3,10,16-tetraone The title compound is prepared by the reaction of 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone under conditions described in Example 1.

EXAMPLE 6

17-Ethyl-1,20-dihydroxy-14-(tert-butyldimethylsiloxy)-12-[2'-(4''-(tert-butyldimethylsiloxy)-3''-methoxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone The title compound is prepared by the reaction of 17-ethyl-1-hydroxy-14-(tert-butyldimethylsiloxy)-12-[2'-(4''-(tert-butyldimethylsiloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone under conditions described in Example 2.

EXAMPLE 7

17-Ethyl-20-fluoro-1-hydroxy-14-(tert-butyldimethylsiloxy)-12-[2'-(4''-(tert-butyldimethylsiloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound is prepared by the reaction of 17-ethyl-1,20-dihydroxy-14-(tert-butyldimethylsiloxy)-12-[2'-(4''-(tert-butyldimethylsiloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone under conditions described in Example 3.

MASS: (FAB) 1044 (M+Li).

EXAMPLE 8

17-Ethyl-20-fluoro-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-20-fluoro-1-hydroxy-14-(tert-butyldimethylsiloxy)-12-[2'-(4''-(tert-butyldimethylsiloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (10 mg) in tetrahydrofuran (0.6 ml) contained in a polypropylene vial was added 40 µl of an HF-pyridine solution in tetrahydrofuran, and the mixture was stirred at room temperature. After 28 hours, the mixture was added to a saturated sodium bicarbonate solution, extracted with ethyl acetate and dried by passage through a magnesium sulfate column. Purification of the concentrate by flash chromatography on silica gel (ethyl acetate: hexane (2:1)+1% methanol) gave the title compound (6 mg).

MASS: (FAB) 832 (M+Na).

Partial $^1$H NMR δ: 5.14m, 4.43M (s, 1H); 4.67(brd, J=4 Hz, 1H); 3.00 (M, 1H); 2.90(d, J=3 Hz, 1H); 2.61(brs. 1H).

EXAMPLE 9

17-Ethyl-20-fluoro-1-hydroxy-12-[2'-[4''-(o-nitrobenzenesulfonyloxy)-3''-methoxycyclohexyl[-1'-methylvinyl]-23,25-dimethoxy-13,19,21,27-tetramethyl-11,28-2,3,10,16-tetraone To a solution of 17-ethyl-20-fluoro-1-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (30 mg) in dry methylene chloride (0.5 ml) was added an excess of diisopropylethyl amine (15.7 µl) and o-nitrobenzenesulfonyl chloride (16.8 mg) followed by addition of 4-dimethylaminopyridine (11 mg). The mixture was stirred at room temperature for 5 hours at which time it was diluted with ethyl acetate, extracted from saturated sodium bicarbonate solution and washed with brine. The combined organics were dried over magnesium sulfate and the concentrate purified by flash chromatography on silica gel (ethyl acetate: hexane (1:2)+1% methanol to give the title compound (33 mg).

Partial $^1$H NMR δ: 8.15(m, 1H); 7.76(m, 3H); 4.69m, 4.39M(s, 1H); 3.21(m, 1H); 3.04M, 3.02m(s, 3H).

EXAMPLE 10

17-Ethyl-20-fluoro-1-hydroxy-12-[2'-(4''-azido-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-20-fluoro-1-hydroxy-12-[2'-[4''-(o-nitrobenzenesulfonyloxy)-3''-methoxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,20,16-tetraone (33 mg) in N,N-dimethyl formamide (0.5 ml) was added an excess of sodium azide (8.8 mg) and the mixture heated to 70° C. After 4 hours the reaction was cooled to room temperature, diluted with ethyl acetate, extracted from half-saturated ammonium chloride, and washed with brine. The combined organics were dried over magnesium sulfate and purified by flash chromatography on silica gel (ethyl acetate: hexane (1:2)+1% methanol) to give the title compound (12 mg).

MASS: (FAB) 841 (M+Na).

Partial $^1$H NMR δ: 4.72m, 4.39M(s, 1H); 4.68(brd J=4 Hz, 1H); 4.33(dd J=62, 8 Hz, 1H); 4.06(brm, 1H).

EXAMPLE 11

17-Ethyl-20-fluoro-1-hydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-20-fluoro-1-hydroxy-12-[2'-(4''-azido-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (12 mg) in 10% aqueous benzene (0.5 ml) was added triphenylphosphine (4.2 mg) and the mixture heated to 70° C. with stirring. After 25 hours, the stir bar was removed and the reaction cooled to room temperature. The mixture was concentrated to 10% volume in vacuo and applied directly to a column of silica gel for purification by flash chromatography (ethyl acetate: hexane (1:1)+1% methanol then 2% ammonium hydroxide, 5% methanol in methylene chloride) to give the title compound (9.4 mg).

MASS: (FAB) 793 (M+H).

Partial $^1$H NMR δ: 5.34(brd J=9 Hz, 1H); 5.15(brd J=10 Hz, 1H); 4.63(brd J=4 Hz, 1H); 4.33(dd J=62, 8 Hz, 1H).

EXAMPLE 12

17-Ethyl-20-fluoro-1-hydroxy-12-[2'-(3'',4''-(dihydroxycyclohexyl-)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone The title compound is prepared by the reaction of 17-ethyl-1-hydroxy-12-[2'-(3'',4''-dihydroxycyclohexy)-1''-methylvinyl]-23,25-dimethoxy-13,19,21,27-tetramethyl-11,28-dioxa-4-aza-tricyclo[22.3.1.0$^{4,9}$]ocatacos-18-ene-2,3,10,16-tetraone under conditions described in Examples 1–4.

EXAMPLE 13

17-Ethyl-20-fluoro-1,14-dihydroxy-12-[2'-(3'',4''-hydroxy-cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound is prepared by the reaction of 17-ethyl-1,14-dihydroxy-12-[2'-(3'',4''-dihydroxycyclohexy)-1'-methylvinyl]-23,25-dimethoxy-13,19,21,27-tetramethyl-11,28-dioxa-4-aza-tricyclo[22.3.1.0$^{4,9}$]octacos-18-ene-2,3,10,16-tetraone under conditions described in Examples 1–3 and Example 8.

EXAMPLE 14

17-Ethyl-20-fluoro-1,14-dihydroxy-12-[2'-(4'''-azido-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone Step A: Preparation of 17-Ethyl-20-fluoro-1-hydroxy-12-[2'-(4'''-t-butyldimethylsilyloxy-3''-methoxycyclohexyl)-1'-methylvinyl]-14-t-butyldimethylsilyloxy-23,25-dimethoxy-13,19,21,27-tetramethyl-11,28-dioxa-4-azatri-cyclo[22.3.1.0$^{4,9}$]octacos-18-ene-2,3,10,16-tetraone To a cooled solution (0° C.) of 17-ethyl-20-fluoro-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]-octacos-18-ene-2,3,10,16-tetraone (395 mg) in dry methylene chloride (15 ml) was added 2,6-lutidine (160 mg) followed by t-butyldimethylsilyl triflouro-methanesulfonate (250 mg).

Reaction temperature is raised to r.t. and stirred under nitrogen atmosphere. After 6 hr, the reaction is quenched with 10 ml of water and extracted with ethyl acetate. Organic layer is washed (water, sat'd NaHCO$_3$, sat'd NaCl) and dried (anhydrous MgSO$_4$). Removal of solvent under reduced pressure gives the crude product.

Step B: Preparation of 17-Ethyl-20-fluoro-1-hydroxy-12-[2'-(4''-hydroxy-3''-methoxycyclohexyl)-1'-methylvinyl]-14-t-butyldimethylsilyloxy-23,25-dimethoxy-13,19,21,27-tetramethyl-11,28-dioxa-4-azatricyclo-[22.3.1.0$^{4,9}$]octacos-18-ene-2,3,10,16-tetraone The crude product from Example 14A (500 mg) is dissolved in acetonitrile (20 ml) and 100 μl of hydrogen fluoride (48%) was added. Reaction is stirred for 20 minutes at room temperature, quenched with sat'd sodium bicarbonate, then extracted with ethyl acetate. Removal of solvent in vacuo followed by chromatography on silica gel gives the desired product.

Step C: Preparation of 17-Ethyl-20-fluoro-1-hydroxy-12-[2'-{4''-(2'''-nitrobenzenesulfonyloxy)-3''-methoxycyclohexyl}-1'-methylvinyl]-14-t-butyldimethylsilyloxy-23,25-di-methoxy-13,19,21,27-tetramethyl-11,28-dioxa-4-azatricyclo[22.3.1.0$^{4,9}$]octacos-18-ene-2,3,10,16-tetraone To a solution of the title compound of Example 14B (721.8 mg) in dry methylene chloride (20 mL) is added diisopropylethylamine (247.4 mg) followed by 2-nitrobenzenesulfonyl chloride (258.8 mg) and then N,N-dimethylaminopyridine (122.2 mg). The yellow solution is stirred at room temperature under a nitrogen atmosphere for 4 hr, and quenched with sat'd aqueous sodium bicarbonate. Organic layer is washed (water, sat'd NaHCO$_3$, sat'd NaCl), dried (anhydrous Na$_2$SO$_4$) and the solvent is removed in vacuo. Chromatography on silica gel gives the title compound Step D: Preparation of 17-Ethyl-20-fluoro-1-hydroxy-12-[2'-(4''-azido-3''-methoxycyclohexyl)-1'-methylvinyl-14-t-butyldimethylsilyloxy-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of the title compound of Example 14C (390 mg) in dry dimethylformamide (5 ml) was added sodium azide (115.7 mg) in one portion. The reaction is heated at 80° C. under nitrogen atmosphere for 4.5 hr. Reaction mixture is cooled to r.t., poured into water (50 ml), and extracted with ethyl acetate. Normal work-up followed by purification via preparative tlc on silica gel gives the product.

Step E: Preparation of 17-Ethyl-20-fluoro-1,14-dihydroxy-12-[2'-(4''-azido-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-9,3,10,16-tetraone To a stirred solution of the title compound of Example 14D (150 mg) in acetonitrile at room temperature is added a solution of 2% hydrogen fluoride in aqueous acetonitrile (1.5 ml). The reaction is stirred for 1.5 hr., quenched with sat'd aqueous sodium bicarbonate and extracted with ethyl acetate. The solvent is removed and the residue is purified by preparative tlc on silica gel to give the title compound.

EXAMPLE 15

17-Ethyl-20-fluoro-1,14-dihydroxy-12-[2'-(4''-amino-3''-methoxycyclohexyl)-1'-methylvinyl]-23,25-dimethoxy-13,19,21,27-tetramethyl-11,28-dioxa-4-azatricyclo [22.3.1.0$^{4,9}$]-octacos-18-ene-2,3,10,16-tetraone A solution of 17-ethyl-20-fluoro-1, 14-dihydroxy-12-[2'-(4''-azido-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (28 1 mg) and triphenylphosphine (9 mg) in 1 ml of wet toluene is stirred at 70° C. overnight. The solvent is removed under reduced pressure, and the residue was purified by preparative tlc on silica gel to give the title compound.

EXAMPLE 16

17-Ethyl-20-fluoro-1,14-dihydroxy-12-[2'-(4''-acetyl amino-3''-methoxycyclohexyl)-1'-methylvinyl]-23,25-dimethoxy-13,19,21,27-tetramethyl-11,28-dioxa-4-azatricyclo-[22.31.0$^{4,9}$]-octacos-18-ene-2,3,10,16-tetraone A solution of 17-ethyl-20-fluoro-1,14-dihydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$] octacos-18-ene-2,3,10,16-tetraone (30 mg) in dry methylene chloride (0.2 ml) was added triethylamine (10 μl) followed by a solution of acetic anhydride in methylene chloride (10 mg in 1 ml) at r.t. Reaction is stirred for 30 minutes and the solvent was removed under nitrogen flow. The crude produce is purified by preparative tlc on silica gel to give the title compound.

EXAMPLE 17

17-Ethyl-20-fluoro-1,14-dihydroxy-12-[2'-(4''-N-(2-pro penyl)-amino-3''-methoxycyclohexyl)-1'-methylvinyl]-23,25-di-methoxy-13,19,21,27-tetramethyl-11,28-dioxa-4-azatricyclo]22.3.1.0$^{4,9}$]octacos-18-ene-2,3,10,16-tetraone The compound 17-ethyl-20-fluoro-1,14-dihydroxy-12-[2 '-(4''-amino-3''-methoxycyclohexyl)-1'-methylvinyl]-23,25-dimethoxy-13,19,21,27-tetramethyl-11,28-dioxa-4aza-tricyclo[22.3.1.0$^{4,9}$]octacos-18-ene-2,3,10,16-tetraone (30 mg) is placed in a dryflask equipped with stir bar and condenser. Dry toluene (1 ml) is added followed by diisopropylethylamine (13 mg) and freshly distilled allyl bromide (40.5 mg) at 0° C. with stirring. The reaction temperature is raised to 70° C. gradually and stirred for 2 hr. The reaction mixture is cooled, and the solvent is removed under nitrogen flow. The residue is purified by preparative tlc on silica gel to give the title compound.

EXAMPLE 18

17-Ethyl-20-fluoro-1,14-dihydroxy-12-[2'-[4''-(N'-t-butoxycarbonyl-D-phenylalanine)amido-3''-methoxycyclohexyl)-1'-methylvinyl]-23,25-dimethoxy-13,19,-21,27-tetra-methyl-11,28-dioxa-4-azatricyclo-[22.3.1.0$^{4,9}$]octacos-18-ene-2,3,10,16-tetraone To a solution of 17-ethyl-20fluoro-1,14-dihydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (44.7 mg) in dry methylene chloride (2 ml) is added 102 mg of freshly prepared BOC-D-phenylalanine anhydride (prepared as described in *Solid Peptide Sythesis*, p. 32, J. M. Steward and J. D. Young, Pierce Chemical Company) under nitrogen. Reaction is stirred at room temperature. After 2.5 hr, the reaction mixture is subjected to work-up and preparative tlc on silica gel to give the title compound.

EXAMPLE 19

17-Ethyl-20fluoro-1,14-dihydroxy-12-[2'-[4'-'-(N'-t-butoxy-carbonyl-L-phenylalanine)amido-3''-methoxycyclohexyl]-1'-methylvinyl]-23,25-dimethoxy-13,19,21,-27-tetra-methyl-11,28-dioxa-4-azatricyclo[22.3.1.0$^{4,9}$]octacos-18-ene-2,3,10,16-tetraone The title compound is prepared by the method of Example 18 utilizing BOC-L-phenylalanine anhydride.

EXAMPLE 20

17-Ethyl-20-fluoro-1,14-dihydroxy-12-(4''-acetoxyacetylamino-3''-methoxycyclohexyl)-1'-methylvinyl]-23,25-dimethoxy-13,19,21,27-tetramethyl-11,28-dioxa-4-azatricyclo]22.3.1.0$^{4,9}$]octacos-18-ene-2,3,10,16-tetraone A solution of 17-ethyl-20-fluoro-1,14-dihydroxy-12-[2'-(4''-amino-3''-methoxycyclohexyl)-1'-methylvinyl]-23,25-dimethoxy-13,19,21,27-tetramethyl-11,28-dioxa-4-azatricyclo]22.3.1.0$^{4,9}$]octacos-18-ene-2,3,10,16- tetraone (40 mg) in dry methylene chloride (0.4 ml) is cooled to 0° C. To this solution is added a solution of acetoxyacetyl chloride (9 mg) in methylene chloride (0.5 ml). The reaction mixture is stirred at 0° C. for 30 minutes, and quenched with a drop of methanol. Purification by preparative tlc on silica gel gives the title compound.

EXAMPLE 21

17-Ethyl-20-fluoro-1,14-dihydroxy-12-{2'-[4'''‚5'''-dicarboethoxy-1''',2''',3'''-triazole)-3''-methoxycyclohexyl]-1'-methyl-vinyl}-23,23-dimethoxy-13,19,21,27-tetramethyl-11,28-dioxa-4-azatricyclo [22.3.1.0$^{4,9}$]-octacos-18- ene-2,3,10,16-tetraone A mixture of 17-ethyl-20-fluoro-1,14-dihydroxy-12-[2'-(4''-azido-3''-methoxycyclohexyl)-1'-methylvinyl]-23,25-dimethoxy-13,19,21,27-tetramethyl- 11,28-dioxa-4-aza-tricyclo[22.3.1.0$^{4,9}$]octacos-18-ene-2,3,10,16-tetraone (20 mg) in neat diethylacetylene dicarboxylate (0.1 ml) is stirred at room temperature overnight. The cycloaddition product is isolated by preparative tlc on silica gel to give the title compound.

EXAMPLE 22

17-Ethyl-20-fluoro-1-hydroxy-12-[2'-(4''-amino-3''-methoxycyclo-hexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone A solution of 500 mg of 17-ethyl-20-fluoro-1,14-dihydroxy-12-[2'-(4''-hydroxy-3-methoxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone in 7 ml of benzene is treated with 10 mg of p-toluenesulfonic acid and the solution is heated at 60° C. for two hours. The reaction mixture is quenched into saturated sodium bicarbonate solution and extracted with ethyl acetate. Combined organic layers are washed with water and saturated sodium chloride solution. The organic solution is dried with anhydrous magnesium sulfate and concentrated. The residue is flash chromatographed on silica gel to give product. This material is dissolved in 10 ml of ethyl acetate and treated with 15 mg of 5% Rh/C. A balloon with hydrogen is placed over the reaction mixture and the mixture stirred until the reaction is complete. The mixture is filtered through diatomaceous earth, concentrated and the residue is subjected to flash chromatography to give product. A solution of 61 mg of this material, diisopropylethyl amine (33 μl) and N,N-dimethylaminopyridine (23.2 mg) in 2 ml of methylene chloride is treated with 35.4 mg of o-nitrobenzenesulfonyl chloride under nitrogen. The reaction mixture is stirred for 4.5 hours and then diluted with aqueous sodium bicarbonate solution. The mixture is repeatedly extracted with ethyl acetate. The combined organic layers are then dried with anhydrous magnesium sulfate, concentrated and are flash chromatographed on silica gel to afford product. This material is dissolved in DMF and then treated with sodium azide (24.4 mg). The reaction mixture is stirred at 80° C. under nitrogen for 4 hours and then diluted with water. The mixture is extracted with ethyl acetate and the combined fractions are washed with water, brine, dried with anhydrous magnesium sulfate and concentrated. The residue is purified by preparation TLC to give the azide. A solution of this azide (23 mg) in 0.5 ml of wet toluene containing 7.8 mg of triphenylphosphine is heated at 70° C. for 17 hours. The reaction mixture is subjected to preparative TLC to give the title compound.

EXAMPLE 23

17-Ethyl-20-fluoro-1-hydroxy-12-[2'-(3''-methoxy-4''-oxo cyclohexyl)-1'-methylvinyl]-14-triisopropylsilyloxy-23,25-dimethoxy-13,19,21,27-tetramethyl-11,28-dioxa-4-aza-tricyclo[22.3.1.0$^{4,9}$]octacos-18-ene-2,3,10,16-tetraone To a cooled solution (−78° C.) of oxalyl chloride (1.5 ml of 2M solution in CH$_2$Cl$_2$) is added dimethyl sulfoxide (361 mg) dropwise, followed by a solution of 17-ethyl-20-fluoro-1-hydroxy-12-[2'-(4''-hydroxy-3''-methoxycyclohexyl)-1'-methylvinyl]-14-triisopropylsilyloxy-23,25-dimethoxy-13,19,21, 27-tetramethyl-11,28-dioxa-4-azatricyclo[22.3.1.0$^{4,9}$] octacos-18-ene-2,3,10,16-tetraone (947 mg) in dry methylene chloride (3 ml). The reaction mixture is stirred for 30 min. at −78° C. and then triethylamine (1 ml) is added. The reaction temperature is raised to room temperature, reaction is poured into water (20 ml), and extracted with ethyl acetate (three times). Combined organic layers are washed (water, sat'd NaHCO$_3$), dried (anhydrous Na$_2$SO$_4$), and filtered. Removal of solvent followed by purification (silica gel column chromatography), gives the title compound.

EXAMPLE 24

17-Ethyl-20-fluoro-1,14-dihydroxy-12-[2'-(3''-methoxy-4''-oxo-cyclohexyl)-1'-methylvinyl]-23,25-dimethoxy-13,19,21,27-tetramethyl-11,28-dioxa-4-azatricyclo [22.3.1.0$^{4,9}$]-octacos-18-ene-2,3,10,16-tetraone To a stirred solution of 17-ethyl-20-fluoro-1-hydroxy-12-[2'-(3''-methoxy-4''-oxo cyclohexyl)-1'-methylvinyl]-14-triisopropylsilyloxy-23,25-dimethoxy-13,19,21,27-tetramethyl-11,18-dioxa-4-azatricyclo[22.3.1.0$^{4,9}$]-octacos-18-ene-2,3,10, 16-tetraone from Example 23 (870 mg) in tetrahydrofuran (20 ml) contained in a polypropylene vial is added 4 ml of an HF-pyridine solution in tetrahydrofuran and the mixture was stirred at room temperature. The reaction mixture is quenched with sat'd aqueous sodium bicarbonate. The organic layer is separated and the aqueous layer is extracted with ethyl acetate three times. Combined organic layers are washed (sat'd NaHCO$_3$, sat'd NaCl), dried (anhydrous Na$_2$SO$_4$), and filtered. Removal of solvent followed by purification (silica gel column chromatography, gives the title compound.

EXAMPLE 25

17-Ethyl-20-fluoro-1,14-dihydroxy-12-[2'-(4''-benzylamino-3''-methoxycyclohexyl)-1'-methylvinyl]-23,25-dimethoxy-13,19,21,27-tetramethyl-11, 28-dioxa-4-azatricyclo-[22.3.1.0$^{4,9}$]octacos-18-ene-2,3,10,16-tetraone To a solution of 17-ethyl-20-fluoro-1, 14-dihydroxy-12-[2'-(3''-methoxy-4''-oxocyclohexyl)-1'-methylvinyl]-23,25-dimethoxy-13,19,21,27-tetramethyl-11,28-dioxa-4-azatricyclo[22.3.1.0$^{4,9}$] octacos-18-ene-2,3,10,16-tetraone from Example 24 (79.7 mg) in dry isopropyl alcohol (3 ml) is added benzylamine (86.5 mg). The mixture is stirred at r.t. for 30 min., and cooled to −78° C. To this solution is added a solution of sodium cyanoborohydride (6.7 mg) in isopropyl alcohol (0.5 ml). The reaction is stirred at −78° C. and poured into ice water. Extraction with ethyl acetate, followed by purification gives the title compound as a mixture of epimers at C-4''.

EXAMPLE 26

17-Ethyl-20-fluoro-1-hydroxy-12-[2'-(4'''-trimethyl amino-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone Iodide 17-Ethyl-20-fluoro-1-hydroxy-12-[2'-(4''-amino-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone is dissolved in absolute ethanol in a heavy walled glass tube. Methyl iodide (large excess) and NaHCO$_3$ is added, the tube is sealed, and heated. Process of the reaction is followed by watching disappearance of the starting amine on thin layer chromatography and the appearance of a more polar new spot. Upon completion of reaction, the quarternary iodide is obtained by evaporation of excess methyl iodide and solvent.

EXAMPLE 27

17-Ethyl-20-fluoro-1,2,14-trihydroxy-12-[2'-(4''-acetyl amino-3''-methoxycyclohexyl)-1'-methylvinyl]-23, 25-dimethoxy-13,1927-tetramethyl-11,28-dioxa-4-azatricyclo-]22.3.1.0$^{4,9}$]octacos-18-ene-3,10,16-trione To a suspension of samarium (63 mg) in dry THF (1 ml) is added a solution of diiodoethane (56 mg in 1 ml THF) at r.t., and stirred for 1 hr. The dark blue solution is cooled to −78° 1 C., and to this mixture is added a solution of 17-ethyl-20-fluoro-1, 14-dihydroxy-12-[2'-(4''-acetylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (166 mg) in 50% THF/MeOH (3 ml). The reaction is stirred at −78° C. for 10 minutes, allowed to warm to room temperature over a period of 10 min., and then quenched with saturated potassium carbonate solution. The organic layer is extracted with ether/ethyl acetate, washed (sat'd NaCl), and dried (anhydrous Na$_2$SO$_4$). Removal of solvent followed by chromatography on silica gel gives the title compound.

EXAMPLE 28

17-Ethyl-20-fluoro-1,14-dihydroxy-12-[2'-(4''-oxadecah ydroquinol-2-on-6''-yl)-1'-methylvinyl]-23,25-dimethoxy-13,19,21,27-tetramethyl-11,28-dioxa-4-azatricyclo]22.3.1.0$^{4,9}$]octacos-18-ene-2,3,10, 16tetraone To a cooled (0° C.) solution of 17-ethyl-20-fluoro-1,14-dihydroxy-12-[2'-(4'-amino-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (77 mg) in methylene chloride (5 ml) is added triethylamine (20 μl) followed by a solution of chloroacetyl chloride (12mg) in methylene chloride (1 ml). The reaction temperature is raised to room temperature and the reaction is stirred until all the starting material is consumed. The reaction is quenched with water, extracted with ethyl acetate, and the combined organic layers are dried (anhydrous sodium sulfate). Removal of solvent gives the crude chloroacetylamide. To a solution of this crude compound in dry ethanol (2 ml) is added a solution of sodium ethoxide in ethanol (5 ml, 0.1 mmole) and the solution is stirred at room temperature. The reaction is quenched with seat's ammonium chloride solution and concentrated under reduced pressure. Purification of the residue via preparative tlc on silica gel gives the title compound.

EXAMPLE 29

17-Ethyl-20-fluoro-1,14-dihydroxy-12-[2'-(4''-oxadecah ydroquinol-2-on-7''-yl)-1'-methylvinyl]-23,25-dimethoxy-13,19,21,27-tetramethyl-11,28-dioxa-4-azatricyclo]22.3.1.0$^{4,9}$]octacos-18-ene-2,3,10,16-tetraone The title compound is prepared by the method of Example 28 utilizing 17-ethyl-20-fluoro-1, 14-dihydr oxy-12-[2'-(3''-amino-4''-hydroxycyclohexyl)-1'-methylvinyl]-23,25-dimethoxy-13,19,21,27-tetramethyl-11,28-dioxa-4-azatricyclo]22.3.1.0$^{4,9}$]octacos-18-ene-2,3,10,16-tetraone as a starting material.

EXAMPLE 30

17-Ethyl-20-fluoro-1,14-dihydroxy-12-{2'-[4''-(N'-phenylamino-carbonyl)amino-3''-methoxycyclohexy]-1'-methylvinyl}-23,25-dimethoxy-13,19,21,27-tetramethyl-11,28-dioxa-4-azatricyclo]22.3.1.0$^{4,9}$]octacos-18-ene-2,3,10,16-tetraone To a solution of 17-ethyl-20-fluoro-1, 14-dihydr oxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (40 mg) in methylene chloride (2 ml) is added phenyl isocyanate (12 mg) at 0° C. with stirring. The reaction mixture is warmed to room temperature and the reaction progress is followed by tlc analysis. The reaction mixture is concentrated under a stream of nitrogen and purified by preparative tlc on silica to give the title compound.

EXAMPLE 31

17-Ethyl-20-fluoro-1,14-dihydroxy-12-{2'-[4''-(ethoxycarbonyl)-amino-3''-methoxycyclohexyl]-1'-methylvinyl}-23,25-dimethoxy-13,19,21,27-tetramethyl-11,28-dioxa-4-azatri-cyclo[22.3.1.0$^{4,9}$]octacos-18-ene-2,3,10,16-tetraone To a solution of 17-ethyl-20-fluoro-1,14-dihydrox y-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (40 mg) in methyl chloride (2 ml) is added triethylamine (10 μl), followed by ethyl chloroformate (15 μl) at 0° C. with stirring. The reaction mixture is warmed to room temperature and the reaction progress is followed by tlc analysis. The solution is quenched with a drop of methanol and is purified by preparative tlc on silica to give the title compound.

EXAMPLE 32

17-Ethyl-20-fluoro-1-hydroxy-12-[2'-(4''-azido-3''-methoxycyclohexyl)-1'-methylvinyl]-23,25-dimethoxy-13,19,21,27-tetramethyl-11,28-dioxa-4-azatricyclo [22.3.1.0$^{4,9}$]-octacos-18-ene-2,3,10,16-tetraone A solution of 17-ethyl-20-fluoro-1-hydroxy-12-[2'-(4'-azido-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-14,18-diene-2, 3,10,16-tetraone (55 mg), tetrakistriphenylphosphine palladium (10 mg), and acetic acid (10 μl) in 3 ml of dry toluene is stirred for 5 min at room temperature under nitrogen atmosphere. To this yellow solution is added tributyltin hydride (30 μl) and stirred an additional 45 min at room temperature. The reaction mixture is subjected to column chromatography on silica gel (elute first with hexane and then with 50% ethyl acetate/hexane) to give the title compound.

EXAMPLE 33

17-Ethyl-20-fluoro-1,14-dihydroxy-12-[2'-(4''-acetam idine-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of ethyl acetamidate hydrochloride (6.3 mg) in 500 μl of dimethylacetamide (DMAC) is added 9 μl of diisopropylethylamine and stirred at 0° C. until the solution becomes clear. This solution is added to a solution of 17-ethyl-20-fluoro-1,14-dihydroxy-12-[2'-

(4″-amino-3″-methoxycyclohexyl)-1′-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone (40 mg) in 500 μl of DMAC at −10° C. The reaction temperature is gradually raised to room temperature and the reaction progress is monitored by tlc analysis. After stirring 2 h at room temperature, 100 μl of trifluoroacetic acid (TFA) is added and the product is isolated by trituration with water as a TFA salt.

EXAMPLE 34

17-Ethyl-20-fluoro-1-hydroxy-12-[2′-(4‴-benzamidine-3″-methoxycyclohexyl)-1′-methylvinyl]-23,25-dimethoxy-13,19,21,27-tetramethyl-11,28-dioxa-4-azatricyclo-[22.3.1.0$^{4,9}$)octacos-18-ene-2,3,10,16-tetraone A solution of 17-ethyl-20-fluoro-1-hydroxy-12-[2′-(4″-amino-3″-methoxycyclohexyl)-1′-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (40 mg) and methyl benzimidate hydrochloride (11 mg) in 500 μl of DMAC is cooled to 0° C. To this solution is added 30 μl of diisopropylethylamine under nitrogen atmosphere. The reaction temperature is raised to room temperature and stirring is continued for additional 2 h at this temperature. TFA (100 μl) is added and the product is isolated by trituration with water as a TFA salt. MASS: (FAB) 864 (M+H-TFA).

EXAMPLE 35

17-Ethyl-20-fluoro-1-hydroxy-12-[2′-[4‴-formamidine-3″-methoxycyclohexyl]-1′-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-20-fluoro-1-hydroxy-12-[2′-(4″-amino-3″-methoxycyclohexyl)-1′-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (35 mg) in 500 μl of dry DMAC is cooled to −10° C. To this solution is added a freshly prepared benzyl formimidate hydrochloride (10 mg) followed by diisopropylethylethylamine (27 ||l) and the mixture is stirred under nitrogen atmosphere. The reaction temperature is raised to room temperature and stirred at this temperature for 2 h. TFA is added (200 μl) and the product is isolated by trituration with water as a TFA salt.

EXAMPLE 36

17-Ethyl-20-fluoro-1-hydroxy-12-[2′-(4″-methylcarbamate-3″-methoxycyclohexyl)-1′-methylvinyl]-23,25-dimethoxy-13,19,21,27tetramethyl-11,28-dioxa-4-azatricyclo[22.3.1.0$^{4,9}$]octacos-18-ene-2,3,10,16-tetraone To a solution of 17-ethyl-20-fluoro-1-hydroxy-12-[2′-(4″-amino-3″-amino-3″-methoxycyclohexyl)-1′-methylvinyl]-23,25-dimethoxy-13,19,21, 27-tetramethyl-11,28-dioxa-4-azatricyclo[22.3.1.0$^{4,9}$]octacos-18-ene-2,3,10,16-tetraone (37 mg) in dry methylene chloride (500 μl) is added diisopropylethylamine (15 μl) followed by methyl chloroformate (5 μl) under nitrogen atmosphere. The reaction mixture is stirred at room temperature for 15 min, then quenched with methanol. The crude material is purified by preparative tlc on silica gel to give the title compound.

EXAMPLE 37

17-Ethyl-20-fluoro-1-hydroxy--12-[2′-[4‴-(2‴″-nitrobenzenesulfonyloxy)-3″-hydroxycyclohexyl]-1′-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (A)
and
17-Ethyl-20-fluoro-1-hydroxy--12-[2′-[3‴-(2‴″-nitrobenzenesulfonyloxy)-4″-hydroxycyclohexyl]-1′-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (B)

To a solution of 17-ethyl-20-fluoro-1-hydroxy-12-[2′-(3″,4″-dihydroxycyclohexyl)-1′-methylvinyl]-23,25-dimethoxy-13,19,21,27-tetramethyl-11,28-dioxa-4-aza-tricyclo[22.3.1.0$^{4,9}$]octacos-18-ene-2,3,10,16-tetraone (200 mg) in dry methylene chloride (20 ml) is added diisopropylethylamine (150 μl) followed by 2-nitrobenzenesulonyl chloride (60 mg), then 4-dimethylaminopyridine (27 mg). The solution is stirred at room temperature under nitrogen atmosphere for 4 h, then quenched with sat'd aqueous sodium bicarbonate solution. The organic layer is washed (water, sat'd NaHCO$_3$, sat'd NaCl), dried (anhydrous Na$_2$SO$_4$) and the solvent is removed in vacuo. Chromatography on silica gel gives the title compounds.

EXAMPLE 38

17-Ethyl-20-fluoro-1-hydroxy-12-[2′-(3″(R),4″(S)-epoxycyclohexyl)-1′-methylvinyl]-23,25-dimethoxy-13,19,21,27-tetramethyl-11,28-dioxa-4-azatricyclo [22.3.1.0$^{4,9}$]-octacos-18-ene-2,3,10,16-tetraone To a solution of 17-ethyl-20-fluoro-1-hydroxy-12-[2′-[4″-(2‴-nitrobenzenesulfonyloxy)-30″-hydroxycyclohexyl]-1′-methylvinyl]-23,25-dimethoxy-13,19,21,27-tetramethyl-11,28-dioxa-4-azatricyclo [22.3.1.0$^{4,9}$]-octacos-18-ene-2,3,10,16-tetraone (60 mg) in 3 ml of dry methylene chloride is added triethylamine (1 ml) and stirred at room temperature for 3 days. The solvent is removed under reduced pressure and the residue is purified by column chromatography on silica gel to give the title compound.

EXAMPLE 39

17-Ethyl-20-fluoro-1-hydroxy-12-[2′-(3″(S),4″(R)-epoxycyclohexyl)-1′-methylvinyl]-23,25-dimethoxy-13,19,21,27-tetramethyl-11,28-dioxa-4-azatricyclo [22.3.1.0$^{4,9}$]-octacos-18-ene-2,3,10,16-tetraone The title compound is prepared by the method of Example 38 utilizing 17-ethyl-20-fluoro-1-hydroxy-12-[2′-[3″-(2‴-nitrobenzenesulfonyloxy)-4″-hydroxycyclohexyl]-1-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone as starting material.

EXAMPLE 40

17-Ethyl-20-fluoro-1-hydroxy-12-[2′-(4‴-azido-3″-hydroxycyclohexyl)-1′-methylvinyl]-23,25-dimethoxy-13,19,21,27-tetramethyl-11,28-dioxa-4-azatricyclo [22.3.1.0$^{4,9}$]-octacos-18-ene-2,3,10,16-tetraone To a solution of 17-ethyl-20-fluoro-1-hydroxy-12-[2′-(3″(R),4″(S)-epoxycyclohexyl)-1′-methylvinyl]-23,25-dimethoxy-13,19,21,27-tetramethyl-11,28-dioxa-4-azatricyclo[22.3.1.0$^{4,9}$]octacos-18-ene- 2,3,10,16-tetraone (200 mg) in ethanol (5 ml) is added a mixture of sodium azide (100 mg) and ammonium chloride (14 mg) in warm water (250 μl). The reaction mixture is heated at 60° C. for 4 h in an oil bath and cooled to room temperature. Removal of solvent in vacuo followed by chromatography on silica gel gives of the title compound.

EXAMPLE 41

17-Ethyl-20-fluoro-1-hydroxy-12-[2'-(3''-azido-4''-hydroxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone The title compound is prepared by the method of Example 40 utilizing 17-ethyl-20-fluoro-1-hydroxy-12-[2'-(3''(S),4''(R)-epoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone as starting material.

EXAMPLE 42

17-Ethyl-20-fluoro-1-hydroxy-12-[2'-(4''-azido-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone A suspension of 17-ethyl-20-fluoro-1-hydroxy-12-[2'-(4''-azido-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (20 mg) and silver oxide (20 mg) in 1.5 ml of methyl iodide is refluxed in a gas-tight bottle for 4 days. The yellow solid is filtered off and the excess methyl iodide is removed. Purification of crude material by preparative tlc on silica gel gives the title compound.

EXAMPLE 43

17-Ethyl-20-fluoro-1-hydroxy-12-[2'-(4''-alpha-amino-3''-methoxycyclohexyl)-1'-methylvinyl]-23,25-dimethoxy-13,19,21,27-tetramethyl-11,28-dioxa-4-azatricyclo [22.3.1.0$^{4,9}$]-octacos-18-ene-2,3,10,16-tetraone A solution of 17-ethyl-20-fluoro-1-1'-methylvinyl]-23,25-di-methoxy-13,19,21,27-tetramethyl-11,28-dioxa-4-azatricyclo[22.3.1.0$^{4,9}$]octacos-18-ene-2,3,10,16-tetraone (20 mg) and triphenylphosphine (7 mg) in 3 ml of 10% water/benzene is refluxed for 16 h in an oil bath. The solvent is removed in vacuo and the crude material is purified by column chromatography on silica gel to give the title compound.

EXAMPLE 44

17-Ethyl-20-fluoro-1-hydroxy-12-[2'-[4''-(2'''-hydroxypropyl)-amino-3''-hydroxycyclohexyl]-1'-methylvinyl]-23,25-dimethoxy-13,19,21,27-tetramethyl-11,28-dioxa-4-azatricyclo[22.3.1.0$^{4,9}$]-octacos-18-ene-2.3.10.16-tetraone To a solution of 17-ethyl-20-fluoro-1-hydroxy-12-[2'-(4''-amino-3''-amino-3''-methoxycyclohexyl)-1'-methylvinyl]-23,25-dimethoxy-13,19,21,27-tetramethyl-11,28-dioxa-4-aza-tricyclo[22.3.1.0$^{4,9}$]octacos-18-ene-2,3,10,16-tetraone (25 mg) in dry methanol (1 ml) is added a large excess of propylene oxide (200 μl) followed by a catalytic amount of p-toluenesulfonic acid at room temperature. After stirring at this temperature for 20 h, the solution is concentrated and purified by preparative tlc on silica gel to give the title compound.

EXAMPLE 45

17-Ethyl-20-fluoro-1-hydroxy-12-[2'-(4''-azido-3''-(2,2-dimethoxy-ethoxy)-cyclohexyl)-1'-methylvinyl]-23,25-dimethoxy-13,19,21,27-tetramethyl-11,28-dioxa-4-azatricyclo[22.3.1.0$^{4,9}$-octacos-18-ene-2.3.10.16-tetraone A suspension of 17-ethyl-20-fluoro-1-hydroxy-12-[2'-(4''-azido-3''-azido-3''-hydroxycyclohexyl-1'-methylvinyl]-23,25-dimethoxy-13,19,21,27-tetramethyl-11,28-dioxa-4-azatricyclo[22.3.1.0$^{4,9}$]octacos-18-ene-2,3,10,16tetraone (25 mg) and silver oxide (25 mg) in 2 ml of bromoacetaldehyde dimethyl acetal is heated at 70° C. for 4 days. The solids are removed by filtration, washed with ethyl acetate, and concentrated in vacuo. The resulting oil is purified by preparative tlc on silica gel to give the title compound.

Alternatively, a solution of 17-ethyl-20-fluoro-1-hydroxy-12-[2'-(4''-azido-3''hydroxycyclohexyl)-1'-methylvinyl]-23,25-dimethoxy-13,19,21,27-tetramethyl-11,28-dioxa-4-azatricyclo [22.3.1.0.$^{4,9}$]octacos-18-ene-2,3,10,16-tetraone (25 mg, in 0.2 ml dry DME) is added to a stirring suspension of potassium hydride (1 equivalent in 0.5 ml DME) followed immediately by addition of a large excess of bromoacetaldehyde dimethyl acetal (0.2 ml). After 2 hours the mixture is quenched with saturated ammonium chloride and extracted with ethyl acetate. The combined organics are dried over magnesium sulfate and concentrated in vacuo. The product is purified by preparative tlc on silica gel to give the title compound.

EXAMPLE 46

17-Ethyl-20-fluoro-1-hydroxy-12-[2'-(4''-azido-3''-ethanaloxy-cyclohexyl)-1'-methylvinyl]-23,25-dimethoxy-13,19,21,27-tetramethyl-11,28-dioxa-4-azatricyclo[22.3.1.0$^{4,9}$-octacos-18-ene-2.3.10.16-tetraone To a solution of 17-ethyl-20-fluoro-1-hydroxy-12-[2'-(4''-azido-3''-azido-3''-(2,2-dimethoxyethoxy)-cyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone (10 mg in 1 ml acetone) is added 15 mg of an acidic ion exchange resin (e.g. Amberlyst-15) and the mixture stirred at room temperature. After 4 hours, the suspension is filtered over diatomaceous earth and concentrated in vacuo. The product is purified by preparative TLC on silica gel to give the title compound.

EXAMPLE 47

17-Ethyl-20-fluoro-1-hydroxy-12-[2'-(1-aza-4-oxabicyclo-[4.4.0]dec-1-ene-6-yl)-1'-methylvinyl]-23,25-dimethoxy-13,19,21,27-tetramethyl-11,28-dioxa-4-aza-tricyclo[22.3.1.0$^{4,9}$-octacos-18-ene-2.3.10.16-tetraone To a solution of 17-ethyl-20-fluoro-1-hydroxy-12-[2'-(4''-azido-3''-azido-3''-ethanaloxycyclohexyl)-1'-methylvinyl]-23,25-dimethoxy-13,19,21,27-tetramethyl-11,28dioxa-4-azatricyclo[22.3.1.0$^{4,9}$]octacos-18-ene-2,3,10,16-tetraone (5.0 mg in 1 ml benzene), is added distilled water (200 μl) followed by triphenylphosphine (3.0 mg) and the mixture heated to 70° C. on a mantle. After 6 hours, the mixture is diluted with ethyl acetate and the layers separated. The organic portion is concentrated in vacuo and purified by preparative TLC on silica gel to give the title compound.

EXAMPLE 48

17-Ethyl-20-fluoro-1-hydroxy-12-[2'-(1-aza-4-oxabicyclo[4.4.0]-dec-6-yl)-1'-methylvinyl]-23,25-dimethoxy-13,19,21,27-tetramethyl-11,28-dioxa-4-aza-tricyclo[22.3.1.0$^{4,9}$]-octacos-18-ene-2,3,10,16-tetraone To a solution of 17-ethyl-20-fluoro-1-hydroxy-12-[2'-(1-aza-4-aza-4-oxa-bicyclo[4.4.0]dec-1-ene-6--yl)-1'-methyl-vinyl]-23,25-dimethoxy-13,19,21,27-tetramethyl-11,28-dioxa-4-azatricyclo[22.3.1.0$^{4,9}$]octacos-18-ene-2,3,10,16-tetraone (5 mg in 400 μl tetrahydrofuran) is added acetic acid (10 μl) and the mixture is cooled to −78° C. Potassium triphenylborohydride (26 μl of a 0.5M THF solution) is added and the mixture stirred at −78° C. After 1.5 hours the reaction is quenched by the addition of half-saturated ammonium chloride solution then diluted with ethyl acetate and the layers separated. The organic portion is dried over sodium sulfate and concentrated in vacuo. Purification by preparative TLC on silica gel gives the title compound.

EXAMPLE 49

17-Ethyl-20-fluoro-1-hydroxy-12-[2'-(4'-β-benzylamino-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone A solution of 17-ethyl-20-fluoro-1-hydroxy-12-[2'-(4'-β-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (77 mg), benzaldehyde (25 mg) and activated molecular sieves in dry methanol (2 ml) is stirred at room temperature for 3 hr. and to this solution is added acetic acid (10 μl) followed by a solution of sodium cyanoborohydride (350 μl, 0.1 molar solution) in methanol. After stirring at room temperature for 15 min., the solid is filtered off and the solvent is removed in vacuo. The residue is purified by prep tlc on silica gel to give the title compound.

EXAMPLE 51

17-Ethyl-20-fluoro-1-hydroxy-12-[2'-(4''-N-(3-(4-hydroxyphenyl)-propenyl)amino-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a solution of 100 mg of 17-ethyl-20-fluoro-1-hydroxy-12-[2'-[4''-amino-3''-methoxycyclohexyl]-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone in dry toluene/DMF (9:1, 2 ml) is added freshly prepared 3-(4-(tert-butyl dimethylsiloxy)-phenyl)propenyl chloride (3 fold excess) followed by diisopropylethylamine (30 μl). After 16 hours of stirring at 80° C., the solvent is removed in vacuo and the residue is purified by preparative tlc on silica gel (50% ethyl acetate/hexane) to give the hydroxy protected compound. The material is dissolved in 2% aqueous HF solution in acetonitrile (1 ml) and stirred at room temperature for 1 hour. The reaction is quenched with aqueous saturated sodium bicarbonate solution and extracted with ethyl acetate. The combined organic layers are washed with brine, dried over anhydrous magnesium sulfate and purified by preparative tlc on silica gel to give the title compound.

EXAMPLE 52

17-Ethyl-20-fluoro-1-hydroxy-12-{2'-[4''-(2'''-methyl-3'''-(4-hydroxyphenyl)propenylamino-3''-methoxycyclohexyl]-1'-methylvinyl}-23,25-dimethoxy-13,19,21,27-tetramethyl-11,28-dioxa-4-azatricyclo[22.3.1.0$^{4,9}$]octacos-18-ene-3,3,10,16-tetraone.

To a solution of 17-ethyl-20-fluoro-1-hydroxy-12-[2'-[amino-3''-methoxycyclohexyl)-1'-methylvinyl]-23,25-dimethoxy-13,19,21,27-tetramethyl-11,28-dioxa-4-aza-tricyclo[22.3.1.0$^{4,9}$]octacos-18-ene-2,3,10,16-tetraone (77 mg) in dry toluene/DMF (9:1, 2 ml) is added a freshly prepared 3-(4-OTBDMS-phenyl)-2-methyl-propenyl chloride (3 fold excess) followed by diisopropylethylamine (150 μl). After 16 hours of stirring at 80° C., the solvent is removed in vacuo and the residue is purified by preparative tlc on silica gel to give the hydroxy protected compound. This material is solvated in 2% aqueous HF solution in acetonitrile (1 ml) and stirred at room temperature for 1 hour. The reaction is quenched with aqueous saturated sodium bicarbonate solution and extracted with ethyl acetate. The combined organic layers are washed with brine, dried over anhydrous magnesium sulfate and purified by preparative tlc on silica gel to give the title compound.

EXAMPLE 53

17-Ethyl-20-fluoro-1,14-dihydroxy-12-[2'-[4''-(aminoacetyl)amino-3''-methoxycyclohexyl)-1'-methylvinyl}-23,25-dimethoxy-13,19,21,27-tetramethyl-11,28-dioxa-4-azatricyclo-[22.3.1.0$^{4,9}$]octacos-18-ene-2,3,10,16-tetraone To a solution of 17-ethyl-20-fluoro-1,14-dihydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg) in dry methylene chloride (4 ml) is added 100 mg of freshly prepared BOC-L-glycine anhydride under nitrogen. After stirring at room temperature for 1.5 hours, the reaction mixture is subjected to work-up and the residue is purified on silica gel to give the BOC protected compound. This material is dissolved in 1 ml of trifluoroacetic acid at −10° C. and stirred at this temperature. After 30 minutes, the reaction mixture is cooled to −78° and freeze-dried to give the solid. Purification of the crude material by preparative tlc on silica gel gives the title compound.

EXAMPLE 54

17-Ethyl-20-fluoro-1-hydroxy-12-[2'-(4''-(L-Trp)amido-3''-methoxycyclohexyl)-1'-methylvinyl]-23,25-dimethoxy-13,19,21,27-tetramethyl-11,28-dioxa-4-azatricyclo-[22.3.1.0$^{4.}$]octacos-18-ene-2,3,10,16-tetraone To a solution of 17-ethyl-20fluoro-20-fluoro-1-hydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone freshly prepared BOC-L-tryptophan anhydride under nitrogen. After stirring at room temperature for 30 minutes, the reaction mixture is subjected to work-up and the residue is purified on silica gel to give BOC protected compound. This material (50 mg) is dissolved in 1 ml of trifluoroacetic acid at −10° C. and stirred at this temperature. After 30 minutes, the reaction mixture is cooled to −78° and freeze-dried to give the solid. Purification of the crude material by preparative tlc on silica gel gives the title compound.

EXAMPLE 55

17Ethyl-20-fluoro-1,14-dihydroxy-12-[2'-(4"-phenyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of 17-ethyl-20-fluoro-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (100 mg, 0.126 mmol, 1 eq) and Cu(OAc)$_2$ (2.8 mg, 0.014 mmol, 0.11 eq) in CH$_2$Cl$_2$ (1 ml) in a 16 mL screw-cap vial equipped with a magnetic stir-bar is added triphenyl bismuth diacetate [prepared immediately prior to use by addition of acetic acid (0.030 mL, 0.504 mmol, 4 eq) to a suspension of triphenyl bismuth carbonate (127 mg, 0.253 mmol, 2 eq) in CH$_2$Cl$_2$ (1 ml)]. The reaction vessel is capped and the mixture stirred for five days. The reaction mixture is diluted with several milliliters of saturated aqueous NaHCO$_3$ and extracted 4 times with CH$_2$Cl$_2$. The organic extracts are combined, dried over anhydrous Na$_2$SO$_4$, filtered and concentrated in vacuo. The product is isolated by preparative TLC on silica gel to give the title compound.

EXAMPLE 56

A. 17-Ethyl-20-fluoro-1,14-dihydroxy-12-[2'-(3"-phenyloxy-4"-hydroxycyclohexyl)-1'-methylvinyl]-23,25-dimethoxy-13,19,21,-27-tetramethyl-11,28-dioxa-4-azatricyclo[22.3.1.0$^{4,9}$]octacos-18-ene-2,3,10,16-tetraone and B. 17-Ethyl-20-fluoro-1,14-dihydroxy-12-[2'-(4"-phenyloxy-3"-hydroxycyclohexyl)-140 -methylvinyl]-23,25-dimethoxy-13,19,21,-27-tetramethyl-11,28-dioxa-4-azatricyclo [22.3.1.0$^{4,9}$]octacos-18-ene-2.3.10.16-tetraone To a stirred solution of 17-ethyl-20-fluoro-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (500 mg, 0.644 mmol, 1 eq) and Cu(OAc)$_2$ (12 mg, 0.064 mmol, 0.1 eq) in CH$_2$Cl$_2$ (10 ml) in a 25 ml recovery flask equipped with a magnetic stir-bar is added triphenyl bismuth diacetate [prepared immediately prior to use by addition of acetic acid (0.220 ml, 3.860 mmol, 6 eq) to a suspension of triphenyl bismuth carbonate (483 mg, 0.965 mmol, 1.5 eq) in CH$_2$Cl$_2$ (10 ml)]. The reaction flask is capped and the mixture stirred at room temperature for 6 hours. The flask is then fitted with a condenser and the mixture is warmed to 40° C. After 40 hours the reaction mixture is cooled, diluted with saturated aqueous NaHCO$_3$ and extracted 4 times with CH$_2$Cl$_2$. The organic extracts are combined, dried over anhydrous Na$_2$SO$_4$, filtered and concentrated in vacuo. The products are separated and purified by flash column chromatography on silica gel followed by preparative TLC on silica gel to yield the title compounds.

EXAMPLE 57

General procedure for the preparation of triarylbismuthines

To a stirred suspension of magnesium (486 mg, 20 mmol) in dry tetrahydrofuran (10 mL) is added slowly a solution of aryl halide (20 mmol) in dry tetrahydrofuran (10 mL). If necessary the mixture is warmed gently to effect Grignard formation. To the stirred solution of the Grignard reagent is added a solution of bismuth trichloride (1.9 g, 6 mmol) dissolved in dry tetrahydrofuran (20 mL). The resulting mixture is stirred for 24 hours. The reaction mixture is poured into a separatory funnel containing brine and extracted 4× with CH$_2$Cl$_2$. The organic extracts were combined and dried over anhydrous Na$_2$SO$_4$. The mixture was filtered and concentrated in vacuo. The triarylbismuthine is isolated and purified by flash column chromatography on silica gel.

EXAMPLE 58

Tri(6-Methoxy-2-naphthyl)bismuth diacetate

To a stirred solution of tris(6-methoxynaphth-2-yl)bismuthine (100 mg, 0.158 mmol) in CH$_2$Cl$_2$ (8 mL) was added iodobenzene diacetate (200 1 mg, 0.621 mmol). The CH$_2$Cl$_2$ was removed in vacuo and the residue was dissolved in several milliliters of 4:1 hexanes/acetone plus small amount of CH$_2$Cl$_2$. The solution was passed through a silica gel plug and eluted with 4:1 hexanes/acetone. The filtrate was concentrated in vacuo. The residue was dissolved in 4:1 hexanes/acetone plus small amount of CH$_2$Cl$_2$ and passed through a second silica gel plug and eluted with 4:1 hexanes/acetone. The filtrate was concentrated in vacuo leaving 52 mg yellow residue that was used without further purification.

EXAMPLE 59

17-Ethyl-20-fluoro-1,14-dihydroxy-12-[2'-(4"-(6"'-tert-butyldimethylsilyloxynaphth-2-yloxy)-3"'-methoxycyclohexyl)-1'-methylvinyl]-23,25-dimethoxy-13,19,21,27-tetra-methyl-11,28-dioxa-4-azatricyclo[22.3.1.0$^{4,9}$]-octacos-18-ene-2,3,10,16-tetraone To a stirred solution of tris(6-tert-butyldimethylsilyloxynaphth-2-yl)bismuthine (100 mg, 0.215 mmol) in CH$_2$Cl$_2$ (4 mL) is added peracetic acid (0.05 mL, 0.238 mmol, 32 wt % in dilute acetic acid). To this stirred solution is added THF (1 mL), 17-ethyl-20-fluoro-1,14-dihydroxy-12-[2'-(4"-hydroxy-3"-methoxycyclohexyl)-1'-methylvinyl]-23,25-dimethoxy-13, 19,21,27-tetramethyl-11,28-dioxa-4-azatricyclo-[22.3.1.0$^{4,9}$]octacos-18-ene2,3,10,16-tetraone (100 mg, 0.126 mmol) and Cu(OAc)$_2$ (catalytic amount). The flask is fitted with a reflux condenser and the mixture is heated to 40° C. for 2 hours. The mixture is allowed to cool and was stirred 72 hours. The reaction is quenched with saturated aqueous NaHCO$_3$ and extracted 4× with CH$_2$Cl$_2$. The organic extracts are combined and dried over anhydrous Na$_2$SO$_4$. The mixture is filtered and concentrated in vacuo. The products are isolated by preparative TLC on silica gel to afford the title compound.

EXAMPLE 60

17-Ethyl-20-fluoro-1,14-dihydroxy-12-[2'-(4"-(6"'-hydroxynaphth-2-yloxy)-3-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of 17-ethyl-20-fluoro-1,14-dihydroxy-12-[2'-(4"-(6"'-tert-butyldimethylsilyloxynaphth-2-yloxy)-3"-methoxycyclohexyl)-1'-methylvinyl]-23,25-dimethoxy-13,19,21,27-tetramethyl- 11,28-dioxa-4-azatricyclo[22.3.1.0⁴,⁹]octacos-18-ene-2,3,10,16-tetraone (73 mg, 0.07 mmol) in CH$_2$Cl$_2$ (2 mL) was added a solution of p-toluenesulfonic acid in methanol (2 mL, 10% solution). The flask is capped and the mixture stirred 4 hours. The reaction is quenched with saturated aqueous NaHCO$_3$ and extracted 4× with CH$_2$Cl$_2$. The organic extracts are combined and dried over anhydrous Na$_2$SO$_4$. The mixture is filtered and concentrated in vacuo. The product is isolated by preparative TLC on silica gel to afford the title compound.

EXAMPLES 61–98

Utilizing the general procedures described in Examples 55 to 60, the following compounds of Formula I (wherein $R^4$ is hydrogen, $R^5$ is methyl, ethyl, propyl or allyl, Q is fluoro and n is 2) are prepared from the appropriate substituted starting materials and reagents.

| EXAMPLE NO. | $R^1$ | $R^2$ | $R^3$ | $R^5$ |
|---|---|---|---|---|
| 61 | 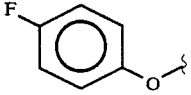 | CH$_3$O | OH | CH$_3$CH$_2$ |
| 62 | 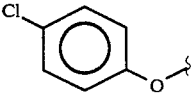 | CH$_3$O | OH | CH$_3$CH$_2$ |
| 63 | 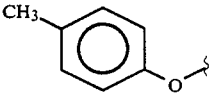 | CH$_3$O | OH | CH$_3$CH$_2$ |
| 64 | 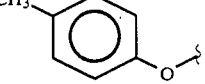 | OH | OH | CH$_3$CH$_2$ |
| 65 | OH | 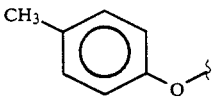 | OH | CH$_3$CH$_2$ |
| 66 | 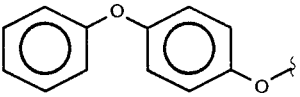 | CH$_3$O | OH | CH$_3$CH$_2$ |
| 67 | 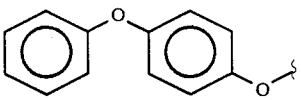 | OH | OH | CH$_3$CH$_2$ |
| 68 | OH | 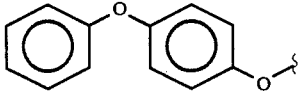 | OH | CH$_3$CH$_2$ |
| 69 | 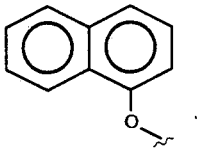 | CH$_3$O | OH | CH$_3$CH$_2$ |
| 70 | 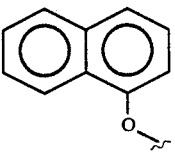 | OH | OH | CH$_3$CH$_2$ |

-continued

| EXAMPLE NO. | R¹ | R² | R³ | R⁵ |
|---|---|---|---|---|
| 71 | OH | 1-naphthyloxy- | OH | CH₃CH₂ |
| 72 | 2-naphthyloxy- | CH₃O | OH | CH₃CH₂ |
| 73 | 2-naphthyloxy- | OH | OH | CH₃CH₂ |
| 74 | OH | 2-naphthyloxy- | OH | CH₃CH₂ |
| 75 | 2-naphthyloxy- | CH₃O | OH | CH₂=CHCH₂ |
| 76 | 6-methoxy-2-naphthyloxy- | CH₃O | OH | CH₃CH₂ |
| 77 | 6-methoxy-2-naphthyloxy- | OH | OH | CH₃CH₂ |
| 78 | CH₃O | 6-methoxy-2-naphthyloxy- | OH | CH₃CH₂ |
| 79 | 2-naphthyloxy- | CH₃O | OH | CH₂=CH—CH₂— |
| 80 | 4-methoxyphenoxy- | CH₃O | OH | CH₃CH₂ |
| 81 | 3-methoxyphenoxy- | CH₃O | OH | CH₃CH₂ |
| 82 | 4-hydroxyphenoxy- | CH₃O | OH | CH₃CH₂ |
| 83 | 4-(methylthio)phenoxy- | CH₃O | OH | CH₃CH₂ |

-continued

| EXAMPLE NO. | R¹ | R² | R³ | R⁵ |
|---|---|---|---|---|
| 84 | 2-methylphenoxy | CH₃O | OH | CH₃CH₂ |
| 85 | 3-methoxyphenoxy | CH₃O | OH | CH₃CH₂ |
| 86 | 3,4-dimethylphenoxy | CH₃O | OH | CH₃CH₂ |
| 87 | 4-methoxyphenoxy | OH | OH | CH₃CH₂ |
| 88 | OH | 4-methoxyphenoxy | OH | CH₃CH₂ |
| 89 | 3-methoxyphenoxy | OH | OH | CH₃CH₂ |
| 90 | OH | 3-methoxyphenoxy | OH | CH₃CH₂ |
| 91 | 4-hydroxyphenoxy | OH | OH | CH₃CH₂ |
| 92 | OH | 4-hydroxyphenoxy | OH | CH₃CH₂ |
| 93 | 6-hydroxy-2-naphthyloxy | OH | OH | CH₃CH₂ |
| 94 | OH | 6-hydroxy-2-naphthyloxy | OH | CH₃CH₂ |
| 95 | 3,4-dichlorophenoxy | CH₃O | OH | CH₃CH₂ |
| 96 | 3,4-methylenedioxyphenoxy | CH₃O | OH | CH₃CH₂ |

-continued

| EXAMPLE NO. | R¹ | R² | R³ | R⁵ |
|---|---|---|---|---|
| 97 | (dihydrobenzofuran-methoxy group) | CH₃O | OH | CH₃CH₂ |
| 98 | (benzodioxole-methoxy group) | CH₃O | OH | CH₃CH₂ |

EXAMPLE 100

17-Ethyl-20-fluoro-1,14-dihydroxy-12-[2'-(4'''-(2-butynyloxy)-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a solution of 17-ethyl-20-fluoro-1,14-dihydroxy-12-[2'-(4'''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (50 mg in 1.5 ml 33% methylene chloride in cyclohexane), 2-butynyl trichloroacetimidate (20 μl neat) is added and the reagents are allowed to mix for 5 minutes. Trifluoromethanesulfonic acid (2 μl neat) is added slowly via syringe acid (2 μl neat) is added and the mixture is stirred at room temperature. After 16 hours the reaction is quenched by the addition of saturated sodium bicarbonate and extracted with ethyl acetate (3×5 ml). The combined organic are washed with brine and dried over magnesium sulfate. Purification of the concentrate by preparative TLC on silica gel gives the title compound.

EXAMPLE 101

17-Ethyl-20-fluoro-1,14-dihydroxy-12-[2'-(4'''-cinnamyloxy-3''-methoxycyclohexyl)-1'-methylvinyl]-23,25-dimethoxy-13,19,21,27-tetramethyl-11,28-dioxa-4-azatricyclo]22.3.1.0$^{4,9}$]octacos-18-ene-2,3,10,16-tetraone To a solution of 17-ethyl-20-fluoro-1,14-dihydroxy-12-[2'-(4'''-hydroxy-3''-methoxycyclohexyl)-1'-methylvinyl]-23,25-dimethoxy-13,19,21,27-tetramethyl-11,28-dioxa-4-azatricyclo]22.3.1.0$^{4,9}$]octacos-18-ene-2,3,10,16-tetraone (50 mg in 1.5 ml 33% methylene chloride in cyclohexane), cinnamyl trichloroacetimidate (26 μl neat) is added and the reagents are allowed to mix for 5 minutes. Trifluoromethanesulfonic acid (2 μl neat) is added slowly via syringe and the mixture is stirred at room temperature. After 15 minutes the reaction is quenched by the addition of saturated sodium bicarbonate and extracted with ethyl acetate (3×5 ml). The combined organics are washed with brine and dried over magnesium sulfate. Purification of the concentrate by preparative TLC on silica gel gives the title compound.

EXAMPLE 102

17-Ethyl-20-fluoro-1,14-dihydroxy-12-[2'-(3'-methoxy-4''-phenyl-propyloxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a solution of 17-ethyl-20-fluoro-1,14-dihydroxy-12[2'-(4'''-cinnamyloxy-3''-methoxycyclohexyl)-1'-methyl-vinyl]-23,25-dimethoxy-13,19,21,27-tetramethyl-11,28-dioxa-4-azatricyclo[22.3.1.0$^{4,9}$]-octacos-18-ene-2,3,10,16-tetraone (37 mg in 2 ml ethanol) is added 4 mg of 5% rhodium on carbon catalyst. The reaction flask is fitted with a hydrogen balloon, evacuated and recharged with hydrogen (3 times) and stirred at room temperature. After 1.5 hours, the mixture is filtered over Celite, concentrated and purified by preparative TLC on silica gel to give the title compound.

EXAMPLE 103

A. 17-Ethyl-20-fluoro-1,14-dihydroxy-12-[2'-(4'''-allyloxy-3''-hydroxycyclohexyl)-1'-methylvinyl]-23,25-dimethoxy-13,19,21,27-tetramethyl-11,28-dioxa-4-azatricyclo-]22.3.1.0$^{4,9}$]octacos-18-ene-2,3,10,16-tetraone and B. 17-Ethyl-20-fluoro-1,14-dihydroxy-12-[2'-(3''-allyloxy-4'''-hydroxycyclohexyl)-1'-methylvinyl]-23,25-dimethoxy-13,19,21,27-tetramethyl-11,28-dioxa-4-azatricyclo-]22.3.1.0$^{4,9}$]octacos-18ene-2,3,10,16-tetraone To a solution of 17-ethyl-20-fluoro-1,14-dihydroxy-1 2-[2'-(3'',4'''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg in 1.5 ml 33% methylene chloride in cyclohexane), allyl trichloroacetimidate (53 μl neat) is added and the reagents are allowed to mix for 5 minutes. Trifluoromethanesulfonic acid (2 μl neat) is added slowly via syringe and the mixture are stirred at room temperature. After 3 hours the reaction is quenched by the addition of saturated sodium bicarbonate and extracted with ethyl acetate (3×5 ml). The combined organics are washed with brine and dried over magnesium sulfate. Purification of the concentrate by flash chromatography on silica gel gives the title compounds.

EXAMPLE 104

A. 17-Ethyl-20-fluoro-1,14-dihydroxy-12-[2'-(3''-hydroxy-4'''-iso-propoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone and B. 17-Ethyl-20-fluoro-1,14-dihydroxy-12-[2'-(4'''-hydroxy-3''-iso-propoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-20-fluoro-1,14-dihydroxy-12-[[2'-(3''4'''-dihydroxycyclohexyl)-1'-methylvinyl]-23,25-dimethoxy-13,19,21,27-tetramethyl-11,28-dioxa-4-azatricyclo]22.3.1.0$^{4,9}$]octacos-18-ene-2,3,10,16-tetraone (110 mg in 1.5 ml 33% methylene chloride in cyclohexane), isopropyl trichloroacetimidate (52 μl neat)

is added and the reagents are allowed to mix for 5 minutes. Trifluoromethanesulfonic acid (2 μl neat) is added slowly via syringe and the mixture stirred at room temperature. After 3 hours the reaction is quenched by the addition of saturated sodium bicarbonate and extracted with ethyl acetate (3×5 ml). The combined organics are washed with brine and dried over magnesium sulfate. Purification of the concentrate by preparative TLC on silica gel gives the title compounds.

EXAMPLE 105

17-Ethyl-20-fluoro-1,14-dihydroxy-2-[2'-(4''-(2-benzyl amino)-ethoxy-3''-methoxycyclohexyl)-1'-methylvinyl]-23,25-dimethoxy-13,19,21,27-tetramethyl-11,28-dioxa-4-azatricyclo]22.3.1.0$^{4,9}$]octacos-18-ene-2,3,10,16-tetraone Step A: 17-Ethyl-20-fluoro-1-hydroxy-14-(tert-butyldimethylsiloxy)-12-[2'-(4''-(tert-butyldimethylsiloxy)-3''-methoxycyclohexyl)-1'-methylvinyl]-23,25-dimethoxy-13,19,21,27-tetramethyl-11,28-dioxa-4-azatricyclo-]22.3.1.0$^{4,9}$]octacos-18ene-2,3,10,16-tetraone To a solution of 17-ethyl-20-fluoro-1,14-dihydroxy-1 2-[2'-(4''-hydroxy-3''-methoxycyclohexyl)-1'-methylvinyl]-23,25-dimethoxy-13,19,21,27-tetramethyl-11,28-dioxa-4-azatricyclo]22.3.1.0$^{4,9}$]octacos-18-ene-2,3,10,16-tetraone (2.35 g) in dry methylene chloride (20 ml) is added an excess of 2,6-lutidine (1.04 ml) and the mixture is stirred at room temperature. After 10 minutes, tert-butyldimethylsilyl trifluoromethanesulfonate (1.50 ml) is added via syringe. After 1 hour the reaction mixture is diluted with ethyl acetate, extracted from saturated sodium bicarbonate, washed with brine and the organic phase dried over magnesium sulfate. Removal of the solvent in vacuo and flash chromatography on silica gel gives the title compound.

Step B: 17-Ethyl-20-fluoro-1-hydroxy-14-(tert-butyldimethylsiloxy)-12-[2'-(4''-hydroxy-3''-methoxycyclohexyl)-1'-methylvinyl]-23,25-dimethoxy-13,19,21,27-tetramethyl-11,28-dioxa-4-azatri- cyclo]22.3.1.0$^{4,9}$]octacos-18-ene-2,3,10,16-tetraone To a solution of 17-ethyl-20-fluoro-1-hydroxy-14-(tert-butyldimethylsiloxy)-12-[2'-(4''-(tert-butyldimethylsiloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (2.91 g) in acetonitrile (15 ml) is added a solution of 2% hydrogen fluoride in aqueous acetonitrile (2 ml), and the mixture is stirred at room temperature. After 4 hours, the solution is diluted with ethyl acetate, extracted with saturated sodium bicarbonate solution and the organic phase dried over magnesium sulfate. Purification of the concentrate by flash chromatography on silica gel gives the title compound.

Step C: 17-Ethyl-20-fluoro-1-hydroxy-14-(tert-butyldimethylsiloxy)-12-[2'-(4''-allyloxy-3''-methoxycyclohexyl)-1'-methylvinyl]-23,25-dimethoxy-13,19,21,27-tetramethyl-11,28-dioxa-4-azatri- cyclo[22.3.1.0$^{4,9}$]octacos-18-ene-2,3,10,16-tetraone To a solution of 17-ethyl-20-fluoro-1-hydroxy-14-(tert-butyldimethylsiloxy)-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (820 mg in 9 ml 33% methylene chloride in cyclohexane) allyl trichloroacetimidate (366 μl neat) is added and the reagents are allowed to mix for 5 minutes. Trifluoromethanesulfonic acid (16 μl neat) is added slowly via syringe and the mixture stirred at room temperature. After 17 hours the reaction is quenched by the addition of saturated sodium bicarbonate and extracted with ethyl acetate (3×15 ml). The combined organics are washed with brine and dried over magnesium sulfate. Purification of the concentrate by flash chromatography on silica gel give the title compound.

Step D: 17-Ethyl-20-fluoro-1-hydroxy-14-(tert-butyldimethylsiloxy)-12-[2'-(4''-(2''',3'''-dihydroxypropyloxy)-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a solution of 17-ethyl-20-fluoro-1-hydroxy-14-(tert-butyldimethylsiloxy)-12-(2'-(4''-allyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (344 mg in 3 ml dry diethyl ether) is added 150 μl pyridine followed by 1.6 ml of a 0.25M osmium tetraoxide solution in THF and the mixture is stirred at room temperature. After 15 minutes, 10 ml of a 20% sodium bisulfite solution are added and the mixture diluted with 20 ml ethyl acetate. The layers are separated and the organic portion re-extracted with 20% sodium bisulfite (3×20 ml) then washed with a saturated brine solution and dried over sodium sulfate. The concentrate is purified by flash chromatography on silica gel to give the title compound.

Step E: 17-Ethyl-20-fluoro-1-hydroxy-14-(tert-butyldimethylsiloxy)-12-[2'-(4''-ethanaloxy-3''-methoxycyclohexyl)-1'-methylvinyl]-23, 25-dimethoxy-13,19,21,27-tetramethyl-11,28-dioxa-4-azatricyclo[22.3.1.0$^{4,9}$]octacos-18-ene-2,3,10,16tetraone To a solution of 17-ethyl-20-fluoro-1-hydroxy-14-(tert-butyldimethylsiloxy)-12-[2'-(4''-(2''',3'''-dihydroxypropyloxy)-3''-methoxycyclohexyl)-1'-methylvinyl]-23,25-dimethoxy-13,19,21,27-tetramethyl-11,28-dioxa-4-aza-tricyclo[22.3.1.0$^{4,9}$]octacos-18-ene-2,3,10,16-tetraone (284 mg in 6 ml of in 20% aqueous tetrahydrofuran) is added sodium metaperiodate (72.3 mg) and the mixture stirred vigorously for 2 hours. At this time an additional 50 mg of sodium metaperiodate are added. After 1.5 hours the mixture is diluted with ethyl acetate and extracted from half-saturated sodium bicarbonate. The organic portion is dried over magnesium sulfate and purified by flash chromatography on silica gel to give the title compound.

Step F: 17-Ethyl-20-fluoro-1-hydroxy-14-(tert-butyldimethylsiloxy)-12-[2'-(4''-(2-benzylamino)ethoxy-3''-methoxycyclohexyl)-1'-methylvinyl]-23,25-dimethoxy-13,19,21,27-tetramethyl-11,28- dioxa-4-azatricyclo[22.3.1.0$^{4,9}$]octacos-18-ene-2,3,10,16-tetraone To a solution of 17-Ethyl-20-fluoro-1-hydroxy-14-(tert-butyldimethylsiloxy)-12-[2'-(4''-ethanaloxy-3''-methoxycyclohexyl)-1'-methylvinyl]-23, 25-dimethoxy-13,19,21,27-tetramethyl-11,28-dioxa-4-azatricyclo[22.3.1.0$^{4,9}$]octacos-18-ene-2,3,10,16-tetraone (9.5 mg in 0.25 ml dry tetrahydrofuran) is added benzylamine (2.5 μl) and the mixture stirred for 10 minutes at room temperature. This is cooled to −78° C. and acetic acid (10 μl) is added followed by potassium triphenylborohydride (25 μl of a 0.5M solution in THF). After 45 minutes, the reaction is quenched by the addition of saturated ammonium chloride and warmed to room temperature. The mixture is extracted with ethyl acetate (3×5 ml) and dried over magnesium sulfate. The concentrate is purified by flash chromatography on silica gel to give the title compound.

Step G: 17-Ethyl-20-fluoro-1,14-dihydroxy-12-[2'-(4''-(2-benzyl-amino)-ethoxy-3''-methoxycyclohexyl)-1'-methylvinyl]-23, 25-dimethoxy-13,19,21,27-tetramethyl-11,28-dioxa-4-azatricyclo[22.3.1.0$^{4,9}$]octacos-18-ene-2,3,10,16-tetraone To a solution of 17-Ethyl-20-fluoro-1-hydroxy-14-(tert-butyldimethylsiloxy)-12-[2'-(4''-(2-benzylamino)-ethoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (3.5 mg) in acetonitrile (100 μl) is added a solution of 2% HF in aqueous acetonitrile (100 μl), and the mixture stirred at room temperature. After 2 hours, the solution is diluted with ethyl acetate, extracted with saturated sodium bicarbonate solution and the organic phase dried over magnesium sulfate. Purification of the concentrate by flash chromatography on silica gel gives the title compound.

EXAMPLE 106

17-Ethyl-20-fluoro-1,14-dihydroxy-12-[2'-(4''-(2-benzyloxyethoxy)-3''-methoxycyclohexyl)-1'-methylvinyl]-23, 25-dimethoxy-13,19,21,27-tetramethyl-11,28-dioxa-4-azatricyclo[22.3.1.0$^{4,9}$]octacos-18-ene-2,3,10,16tetraone Step A: 17-Ethyl-20-fluoro-1-hydroxy-14-(tert-butyldimethylsiloxy)-12-[2'-(4''-(2-hydroxyethoxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16tetraone To a solution of 17-ethyl-20-fluoro-1-hydroxy-14-(tert-butyldimethylsiloxy)-12-[2'-(4''-ethanaloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (126 mg in 1.3 ml dry tetrahydrofuran) at −78° C. is added potassium triphenylborohydride (320 μl of a 0.5M solution in THF). After 45 minutes, the reaction is quenched by the addition of saturated ammonium chloride and warmed to room temperature. The mixture is extracted with ethyl acetate (3×15 ml) and dried over magnesium sulfate. The concentrate is purified by flash chromatography on silica gel to give the title compound.

Step B: 17-Ethyl-20-fluoro-1-hydroxy-14-(tert-butyldimethylsiloxy)12-[2'-(4''-(2-benzyloxyethoxy)-3''-methoxycyclohexyl)-1'-methylvinyl]-23, 25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-20-fluoro-1-hydroxy-14-(tert-butyldimethylsiloxy)-12-[2'-(4''-(2-benzyloxyethoxy)-3''-methoxycyclohexyl)-1'-methylvinyl]-23,25-dimethoxy-13,19,21,27-tetramethyl-11,28-dioxa-4-aza-tricyclo[ 22.3.1.0$^{4,9}$]octacos-18-ene-2,3,10,16tetraone (41.7 mg in 0.6 ml 33% methylene chloride in cyclohexane), benzyl trichloroacetimidate (15.8 μl neat) is added and the reagents are allowed to mix for 5 minutes. Trifluoromethanesulfonic acid (2 μl neat) is added slowly via syringe and the mixture is stirred at room temperature. After 7 hours the reaction is quenched by the addition of saturated sodium bicarbonate and extracted with ethyl acetate (3×5 ml). The combined organics are washed with brine and dried over magnesium sulfate. Purification of the concentrate by flash chromatography on silica gel given the title compound.

Step C: 17-Ethyl-20-fluoro-1,14-dihydroxy-12-[2'-(4''-(2-benzyloxyethoxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16tetraone To a solution of 17-ethyl-20-fluoro-1-hydroxy-14-(tert-butyldimethylsiloxy)-12-[2'-(4''-(2-benzyloxyethoxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16tetraone (10 mg) in acetonitrile (500 μl) is added a solution of 2% HF in aqueous acetonitrile (200 μl), and the mixture is stirred at room temperature. After 2.5 hours, the solution is diluted with ethyl acetate, extracted with saturated sodium bicarbonate solution and the organic phase dried over magnesium sulfate. Purification of the concentrate by flash chromatography on silica gel gives the title compound.

EXAMPLE 107

17-Ethyl-20-fluoro-1,14-dihydroxy-12-[2'-(4''-(napth-2-yloxy)-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-20-fluoro-1,14-dihydroxy-12-[2'-(4''-(napth-2-yloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone in 33% methylene chloride/cyclohexane is added 1.5 equivalents of allyl trichloroacetimidate, and the reagents are allowed to mix for 5 minutes. A catalytic amount of trifluoromethanesulfonic acid is then added slowly via syringe and the mixture is stirred at room temperature. After 3 hours the reaction is quenched by the addition of saturated sodium bicarbonate and extracted with ethyl acetate. The combined organics are washed with brine and dried over magnesium sulfate. Purification of the concentrate by flash chromatography on silica gel gives the title compound.

EXAMPLES 108–134

Utilizing the general procedures described in Examples 100 to 107, the following compounds of Formula I (wherein $R^4$ is hydrogen, $R^5$ is methyl, ethyl, propyl or allyl, Q is fluoro, and n is 2) are prepared from the appropriately substituted starting materials and reagents.

| EXAMPLE NO. | R$^1$ | R$^2$ | R$^3$ | R$^5$ |
|---|---|---|---|---|
| 108 | ⎯⎯⎯⎯⎯⎯O⎯ |  | OH | OH | CH$_3$CH$_2$ |
| 109 | OH | ⎯⎯⎯⎯⎯⎯O⎯ | OH | CH$_3$CH$_2$ |

-continued

| EXAMPLE NO. | R¹ | R² | R³ | R⁵ |
|---|---|---|---|---|
| 110 | CH₂=CH-CH₂-O- (allyloxy, trans) | OH | OH | CH₃CH₂ |
| 111 | OH | CH₂=CH-CH₂-O- (allyloxy, trans) | OH | CH₃CH₂ |
| 112 | (CH₃)₂C=CH-CH₂-O- | OH | OH | CH₃CH₂ |
| 113 | OH | (CH₃)₂C=CH-CH₂-O- | OH | CH₃CH₂ |
| 114 | CH₃CH=C(CH₃)-CH₂-O- | OH | OH | CH₃CH₂ |
| 115 | OH | CH₃CH=C(CH₃)-CH₂-O- | OH | CH₃CH₂ |
| 116 | Ph-CH=CH-CH₂-O- | OH | OH | CH₃CH₂ |
| 117 | OH | CH₃CH₂-CH(CH₃)-O- | H | CH₃CH₂ |
| 118 | CH₂=C(CH₃)-CH(CH₃)-O- | OH | H | CH₃CH₂ |
| 119 | OH | CH₂=C(CH₃)-CH(CH₃)-O- | H | CH₃CH₂ |
| 120 | Ph-CH=CH-CH₂-O- | OH | H | CH₃CH₂ |
| 121 | Ph-CH(CH₃)-O- | CH₃O | OH | CH₃CH₂ |
| 122 | Ph-CH=C(CH₃)-CH₂-O- | CH₃O | OH | CH₃CH₂ |
| 123 | CH₃CH=C(CH₃)-CH=CH-CH₂-O- | CH₃O | OH | CH₃CH₂ |
| 124 | (CH₃)₃C-CH=CH-CH₂-O- | CH₃O | OH | CH₃CH₂ |
| 125 | cyclohexyl-CH=CH-CH₂-O- | CH₃O | OH | CH₃CH₂ |

-continued

| EXAMPLE NO. | R¹ | R² | R³ | R⁵ |
|---|---|---|---|---|
| 126 | 4-F-C₆H₄-CH=CH-CH₂-O- | $CH_3O$ | OH | $CH_3CH_2$ |
| 127 | 4-Cl-C₆H₄-CH=CH-CH₂-O- | $CH_3O$ | OH | $CH_3CH_2$ |
| 128 | 4-Br-C₆H₄-CH=CH-CH₂-O- | $CH_3O$ | OH | $CH_3CH_2$ |
| 129 | 4-CH₃O-C₆H₄-CH=CH-CH₂-O- | $CH_3O$ | OH | $CH_3CH_2$ |
| 130 | 4-HO-C₆H₄-CH=CH-CH₂-O- | $CH_3O$ | OH | $CH_3CH_2$ |
| 131 | 3,4-methylenedioxy-C₆H₃-CH=CH-CH₂-O- | $CH_3O$ | OH | $CH_3CH_2$ |
| 132 | 4-F-C₆H₄-CH₂CH₂CH₂-O- | $CH_3O$ | OH | $CH_3CH_2$ |
| 133 | CH₂=CH-CH₂-O- | CH₂=CH-CH₂-O- | OH | $CH_3CH_2$ |
| 134 | CH₃CH₂CH₂-O- | CH₃CH₂CH₂-O- | OH | $CH_3CH_2$ |

EXAMPLES 135–173

Utilizing the general procedures described in Examples 55 to 60 and 99 to 107, the following compounds of Formula I (wherein R⁴ is hydrogen, R⁵ is methyl, ethyl, propyl or allyl, Q is fluoro, and n is 2) are prepared from the appropriately substituted starting materials and reagents.

| EXAMPLE NO. | R¹ | R² | R³ | R⁵ |
|---|---|---|---|---|
| 135 | 4-HO-C₆H₄-O- | $CH_3O$ | H | $CH_3CH_2$ |
| 136 | 4-HO-C₆H₄-O- | $CH_2=CHCH_2O$ | OH | $CH_3CH_2$ |
| 137 | 4-HO-C₆H₄-O- | $CH_3O$ | OH | $CH_2=CHCH_2-$ |

-continued

| EXAMPLE NO. | R¹ | R² | R³ | R⁵ |
|---|---|---|---|---|
| 138 | 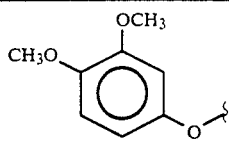 2,4-dimethoxyphenoxy | CH₃O | OH | CH₃CH₂CH₂ |
| 139 | 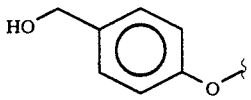 4-(hydroxymethyl)phenoxy | CH₃O | OH | CH₃CH₂ |
| 140 | 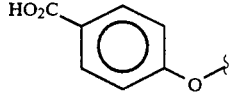 4-carboxyphenoxy | CH₃O | OH | CH₃CH₂ |
| 141 | 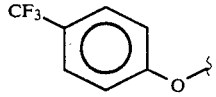 4-(trifluoromethyl)phenoxy | CH₃O | OH | CH₃CH₂CH₂ |
| 142 | 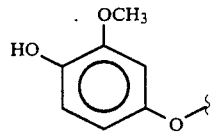 4-hydroxy-3-methoxyphenoxy | CH₃O | H | CH₂=CHCH₂— |
| 143 | 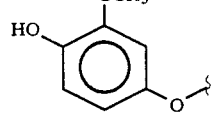 4-hydroxy-3-methoxyphenoxy | CH₂=CHCH₂O | OH | CH₃CH₂ |
| 144 | 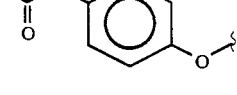 4-acetoxyphenoxy | CH₃O | OH | CH₃CH₂ |
| 145 |  4-(methylsulfinyl)phenoxy | CH₃O | OH | CH₃CH₂ |
| 146 | 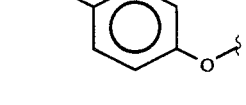 4-(methylsulfonyl)phenoxy | CH₃O | OH | CH₃CH₂ |
| 147 |  6-hydroxy-2-naphthyloxy | CH₃O | OH | CH₃CH₂ |
| 148 | 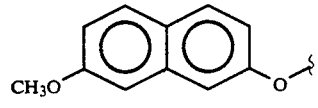 6-methoxy-2-naphthyloxy | CH₃O | OH | CH₃CH₂ |
| 149 | 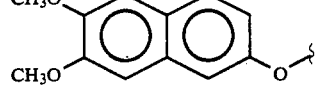 6,7-dimethoxy-2-naphthyloxy | CH₃O | H | CH₂=CHCH₂— |

-continued
| EXAMPLE NO. | R¹ | R² | R³ | R⁵ |
|---|---|---|---|---|
| 150 | 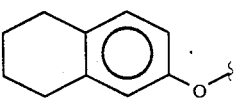 | CH₃O | OH | CH₃CH₂ |
| 151 | 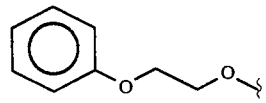 | CH₃O | OH | CH₃CH₂ |
| 152 | 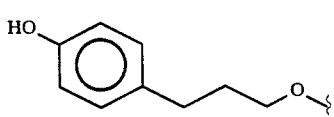 | CH₃O | OH | CH₃CH₂ |
| 153 | 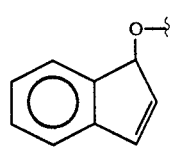 | CH₃O | OH | CH₃ |
| 154 | 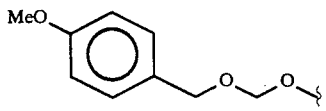 | CH₃O | OH | CH₃CH₂ |
| 155 | 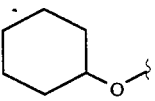 | CH₃O | OH | CH₃CH₂ |
| 156 | 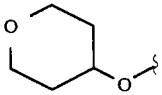 | CH₃O | OH | CH₃CH₂ |
| 157 | 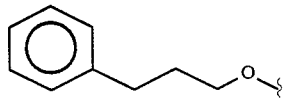 | CH₃O | H | CH₃CH₂ |
| 158 | 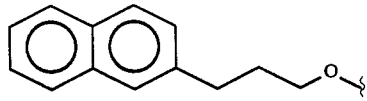 | CH₃O | H | CH₃CH₂ |
| 159 | 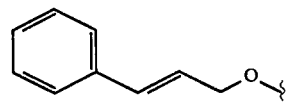 | CH₃CH₂O | OH | CH₃CH₂ |
| 160 | 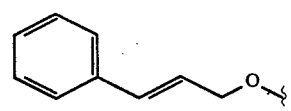 | (CH₃)₂CHO | OH | CH₃CH₂ |
| 161 | 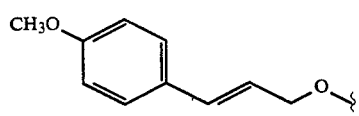 | CH₃CH₂O | OH | CH₃CH₂ |

-continued

| EXAMPLE NO. | $R^1$ | $R^2$ | $R^3$ | $R^5$ |
|---|---|---|---|---|
| 162 | HO-C6H4-CH=CH-CH2-O- | $CH_3CH_2O$ | OH | $CH_3CH_2$ |
| 163 | $CH_3O$-C6H4-CH=CH-CH2-O- | $CH_3CH_2CH_2O$ | OH | $CH_3CH_2$ |
| 164 | HO-C6H4-CH=CH-CH2-CH2- | $CH_3CH_2CH_2O$ | OH | $CH_3CH_2$ |
| 165 | HO-C6H4-CH=CH-CH2-O- | $CH_3CH_2CH_2O$ | OH | $CH_3CH_2$ |
| 166 | $CH_3O$-C6H4-CH=CH-CH2-O- | $(CH_3)_2CHO$ | OH | $CH_3CH_2$ |
| 167 | HO-C6H4-CH=CH-CH2-O- | $(CH_3)_2CHO$ | OH | $CH_3CH_2$ |
| 168 | $H_2NCH_2CH_2O-$ | $CH_3O$ | OH | $CH_3CH_2$ |
| 169 | $H_2NCH_2CH_2O-$ | $CH_3O$ | H | $CH_3CH_2$ |
| 170 | $(CH_3)_2NCH_2CH_2O-$ | $CH_3O$ | OH | $CH_3CH_2$ |
| 171 | $(CH_3)_2NCH_2CH_2O-$ | $CH_3O$ | H | $CH_3CH_2$ |
| 172 | $CH_3NHCH_2CH_2O-$ | $CH_3O$ | OH | $CH_3CH_2$ |
| 173 | $CH_3NHCH_2CH_2O-$ | $CH_3O$ | H | $CH_3CH_2$ |

EXAMPLES 174-211

Utilizing the general procedures described in Examples 1 to 60 and 99 to 107, the following compounds of Formula I (wherein $R^4$ is hydrogen, $R^5$ is methyl, ethyl, propyl or allyl, Q is fluoro, and n is 2) are prepared from the appropriately substituted starting materials and reagents.

| EXAMPLE NO. | $R^1$ | $R^2$ | $R^3$ | $R^5$ |
|---|---|---|---|---|
| 174 | C6H5-O- | $N_3-$ | H | $CH_3CH_2$ |
| 175 | $N_3-$ | C6H5-O- | H | $CH_3CH_2$ |
| 176 | C6H5-O- | $H_2N-$ | H | $CH_3CH_2$ |
| 177 | $H_2N-$ | C6H5-O- | H | $CH_3CH_2$ |

-continued

| EXAMPLE NO. | R¹ | R² | R³ | R⁵ |
|---|---|---|---|---|
| 178 | propionamide (CH₃CH₂C(O)NH–) | phenoxy (PhO–) | H | $CH_3CH_2$ |
| 179 | allylamino (CH₂=CHCH₂NH–) | phenoxy | H | $CH_3CH_2$ |
| 180 | acetoacetamide (CH₃C(O)CH₂C(O)NH–) | phenoxy | H | $CH_3CH_2$ |
| 181 | cyclopropanecarboxamide | phenoxy | H | $CH_3CH_2$ |
| 182 | formamide (HC(O)NH–) | phenoxy | H | $CH_3CH_2$ |
| 183 | benzylamino (PhCH₂NH–) | phenoxy | H | $CH_3CH_2$ |
| 184 | N-phenylureido (PhNHC(O)NH–) | phenoxy | H | $CH_3$ |
| 185 | $NH_2$ | 4-hydroxyphenoxy | H | $CH_3CH_2$ |
| 186 | $NH_2$ | 4-hydroxyphenoxy | OH | $CH_3CH_2$ |
| 187 | $NH_2$ | 4-hydroxyphenoxy | H | $CH_2=CHCH_2-$ |
| 188 | $NH_2$ | 2,4-dimethoxyphenoxy (with OCH₃, CH₃O) | OH | $CH_3CH_2CH_2$ |
| 189 | $NH_2$ | 4-(hydroxymethyl)phenoxy | OH | $CH_3CH_2$ |
| 190 | $NH_2$ | 4-carboxyphenoxy (HO₂C–C₆H₄–O–) | H | $CH_3CH_2$ |

-continued

| EXAMPLE NO. | R¹ | R² | R³ | R⁵ |
|---|---|---|---|---|
| 191 | NH₂ | 4-CF₃-C₆H₄-O- | OH | CH₃CH₂CH₂ |
| 192 | NH₂ | 2-OCH₃-4-(O-)-phenol (HO, OCH₃, O-) | H | CH₂=CHCH₂- |
| 193 | (CH₃)₂N | 2-OCH₃-4-(O-)-phenol (HO, OCH₃, O-) | OH | CH₃CH₂ |
| 194 | NH₂ | 4-(CH₃C(O)O)-C₆H₄-O- | H | CH₂CH₃ |
| 195 | NH₂ | 4-CH₃SO-C₆H₄-O- | OH | CH₃CH₂ |
| 196 | (CH₃)₂N | 4-CH₃SO₂-C₆H₄-O- | OH | CH₂CH₃ |
| 197 | NH₂ | 4-CH₃O-C₆H₄-O- | OH | CH₂CH₃ |
| 198 | NH₂ | 4-CH₃O-C₆H₄-O- | H | CH₃CH₂ |
| 199 | 4-HO-C₆H₄-O- | NH₂ | H | CH₃CH₂ |
| 200 | 4-CH₃O-C₆H₄-O- | NH₂ | H | CH₃CH₂ |
| 201 | NH₂ | 3,4-(CH₃O)₂-C₆H₃-O- (OCH₃, CH₃O, O-) | OH | CH₃CH₂ |
| 202 | 3,4-(CH₃O)₂-C₆H₃-O- (OCH₃, CH₃O, O-) | NH₂ | OH | CH₃CH₂ |

-continued

| EXAMPLE NO. | R¹ | R² | R³ | R⁵ |
|---|---|---|---|---|
| 203 | $(CH_3)_2N$ | 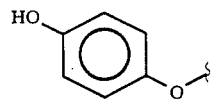 | OH | $CH_3CH_2$ |
| 204 | $(CH_3)_3N^+$ | 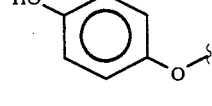 | OH | $CH_3CH_2$ |
| 205 | $NH_2$ | 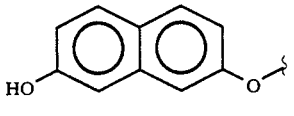 | OH | $CH_3CH_2CH_2$ |
| 206 | $NH_2$ |  | H | $CH_3CH_2$ |
| 207 | $NH_2$ | 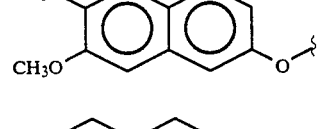 | H | $CH_2=CHCH_2-$ |
| 208 | $NH_2$ |  | OH | $CH_3CH_2$ |
| 209 | 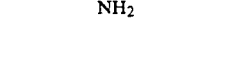 | $NH_2$ | H | $CH_3CH_2$ |
| 210 | 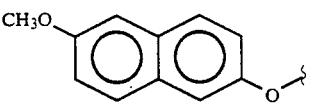 | $NH_2$ | H | $CH_3CH_2$ |
| 211 | 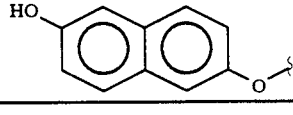 | $NH_2$ | H | $CH_3CH_2$ |

EXAMPLES 212–256

Utilizing the general procedures described in Examples 1-60 and 99-107, the following compounds of Formula I (wherein R⁴ is hydrogen, R⁵ is methyl, ethyl, propyl or allyl, Q is fluoro, and n is 2) are prepared from the appropriately substituted starting materials and reagents.

| EXAMPLE NO. | R¹ | R² | R³ | R⁵ |
|---|---|---|---|---|
| 212 | $N_3-$ | 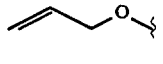 | OH | $CH_3CH_2$ |
| 213 | $NH_2$ | 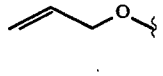 | OH | $CH_3CH_2$ |
| 214 | $NH_2$ | 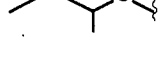 | OH | $CH_3CH_2$ |
| 215 | $NH_2$ | 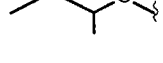 | H | $CH_3CH_2$ |

-continued
| EXAMPLE NO. | R¹ | R² | R³ | R⁵ |
|---|---|---|---|---|
| 216 | NH₂ | 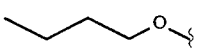 | OH | CH₃CH₂ |
| 217 | NH₂ | 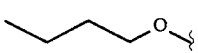 | H | CH₃CH₂ |
| 218 | NH₂ | 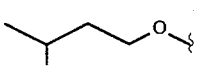 | OH | CH₃CH₂ |
| 219 | NH₂ | 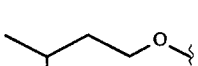 | H | CH₃CH₂ |
| 220 | NH₂ | 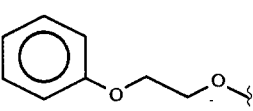 | OH | CH₃CH₂ |
| 221 | NH₂ | 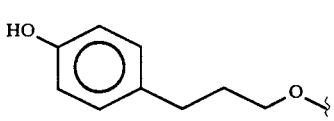 | OH | CH₃CH₂ |
|  | NH₂ | 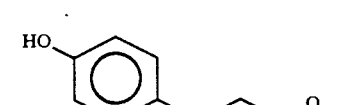 | H | CH₃CH₂ |
| 222 | NH₂ | 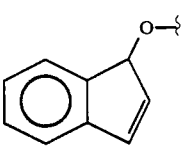 | H | CH₃CH₂ |
| 223 | NH₂ | 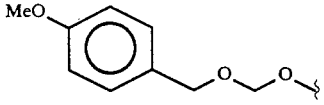 | OH | CH₃CH₂ |
| 224 | NH₂ | 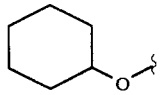 | OH | CH₃CH₂ |
| 225 | NH₂ | 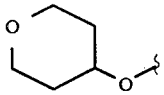 | OH | CH₃CH₂ |
| 226 | NH₂ | 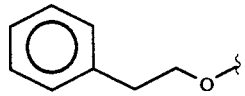 | H | CH₃CH₂ |
| 227 | NH₂ | 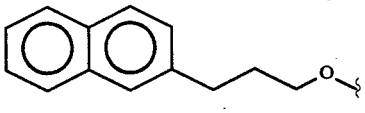 | H | CH₃CH₂ |
| 228 | NH₂ | 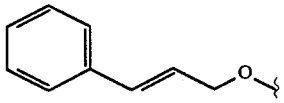 | OH | CH₃CH₂ |

-continued

| EXAMPLE NO. | R¹ | R² | R³ | R⁵ |
|---|---|---|---|---|
| 229 | NH₂ | (E)-PhCH=CHCH₂O- | H | CH₃CH₂ |
| 230 | NH₂ | (E)-PhCH=CHCH₂O- | OH | CH₂=CHCH₂ |
| 231 | NH₂ | PhCH₂CH₂CH₂O- | OH | CH₃CH₂ |
| 232 | NH₂ | PhCH₂CH₂CH₂O- | H | CH₃CH₂ |
| 233 | NH₂ | PhCH₂OCH₂CH₂O- | OH | CH₃CH₂ |
| 234 | NH₂ | PhCH₂OCH₂CH₂O- | H | CH₃CH₂ |
| 235 | NH₂ | (E)-4-HO-C₆H₄-CH=CHCH₂O- | OH | CH₃CH₂ |
| 236 | NH₂ | (E)-4-HO-C₆H₄-CH=CHCH₂O- | H | CH₃CH₂ |
| 237 | NH₂ | (E)-4-HO-C₆H₄-CH=CHCH₂O- | OH | CH₂=CHCH₂ |
| 238 | NH₂ | (E)-4-HO-C₆H₄-CH=CHCH₂O- | H | CH₂=CHCH₂ |
| 239 | NH₂ | CH₂=C(CH₃)CH₂O- | H | CH₃CH₂ |
| 240 | NH₂ | (E)-CH₃CH=CHCH₂O- | H | CH₃CH₂CH₂ |
| 241 | NH₂ | (CH₃)₂C=CHCH₂O- | H | CH₃CH₂ |
| 242 | NH₂ | (E)-CH₃CH=CHCH₂O- | H | CH₃CH₂ |

-continued

| EXAMPLE NO. | R¹ | R² | R³ | R⁵ |
|---|---|---|---|---|
| 243 | $NH_2$ | (1-methylallyl ether structure: $CH_2=CH-CH(CH_3)-O-$) | H | $CH_3CH_2$ |
| 244 | $NH_2$ | (1-methylallyl ether structure: $CH_2=CH-CH(CH_3)-O-$) | H | $CH_3$ |
| 245 | $NH_2$ | (4-methoxycinnamyl ether: $CH_3O-C_6H_4-CH=CH-CH_2-O-$) | H | $CH_2CH_3$ |
| 246 | $NH_2$ | (4-fluorocinnamyl ether: $F-C_6H_4-CH=CH-CH_2-O-$) | H | $CH_2CH_3$ |
| 247 | $NH_2$ | $CH_3C\equiv C-CH_2-O$ | H | $CH_3CH_2CH_2$ |
| 248 | $NH_2$ | $H_2NCH_2CH_2O$ | OH | $CH_3CH_2$ |
| 249 | $NH_2$ | $H_2NCH_2CH_2O$ | H | $CH_3CH_2$ |
| 250 | $NH_2$ | $(CH_3)_2NCH_2CH_2O$ | OH | $CH_3CH_2$ |
| 251 | $NH_2$ | $(CH_3)_2NCH_2CH_2O$ | H | $CH_3CH_2$ |
| 252 | $NH_2$ | $CH_3NHCH_2CH_2O$ | OH | $CH_3CH_2$ |
| 253 | $NH_2$ | $CH_3NHCH_2CH_2O$ | H | $CH_3CH_2$ |
| 254 | $(CH_3)_2N$ | $H_2NCH_2CH_2O$ | OH | $CH_3CH_2$ |
| 255 | $(CH_3)_2N$ | $(CH_3)_2NCH_2CH_2O$ | OH | $CH_3CH_2$ |
| 256 | $CH_3NH$ | $CH_3NHCH_2CH_2O$ | OH | $CH_3CH_2$ |

EXAMPLE 257

T-Cell Proliferation Assay

1. Sample Preparation

The compounds to be assayed were dissolved in absolute ethanol at 1 mg/ml.

2. Assay

Spleens from C57B1/6 mice were taken under sterile conditions and gently dissociated in ice-cold RPMI 1640 culture medium (GIBC) (Grand Island, N.Y.), supplemented with 10% heat-inactivated fetal calf serum (GiBO). Cells were pelleted by centrifugation at 1500 rpm for 8 minutes. Contaminating red cells were removed by treating the pellet with ammonium chloride lysing buffer (GIBO) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 25° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $2.5 \times 10^5$ cells/ml in complete medium composed of RPMI 1640 medium with 10% heat-inactivated fetal calf serum, 100 mM glutamine, 1 mM sodium pyruvate, $2 \times 10^{-5}M$ 2-mercaptoethanol and 50 µg/ml gentamycin. Ionomycin was added at 250 ng/ml and PMA at 10 ng/ml. The cell suspension was immediately disubstituted into 96 well flat-bottom microculture plates (Costar) at 200 µl/well. The various dilutions of the compound to be tested were then added in triplicate wells at 20 µl/well. The compound 17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone was used as a standard. The culture plates were then incubated at 37° C. in a humidified atmosphere 5% $CO_2$-95% air for 44 hours. The proliferation of T lymphocytes was assessed by measurement of tritiated thymidine incorporation. After 44 hours of culturing, the cells were pulse-labelled with 2 µCi/well of tritiated thymidine (NEN, Camgridge, Mass.). After another 4 hours of incubation, cultures were harvesting on glass fiber filters using a multiple sample harvester. Radio activity of filter discs corresponding to individual wells was measured by standard liquid scintillation counting methods (Betacounter). Mean counts per minute of replicate wells were calculated and the results expressed as concentration of compound required to inhibit tritiated thymidine uptake of T-cells by 50%.

A selection of compounds were tested according to the previous procedure. The title compounds of the following Examples had activity in inhibiting the proliferation of T-cells in the aforementioned assay:

4, 8, 11.

The results of this assay are representative of the intrinsic immunosuppressive activity of the compounds of the present invention.

For determining antagonist activity, the foregoing procedure is modified in that dilutions of compounds are cultured with 17-ally-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0⁴,⁹octacos-18-ene-2,3,10,16-tetraone (as a standard) at a concentration of 1.2 nM, a concentration which inhibits T cell proliferation by 100%, the concentration of compound required to reverse the inhibition obtained by the standard alone by 50% is measured, and the $ED_{50}$ value is determined.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of Formula I:

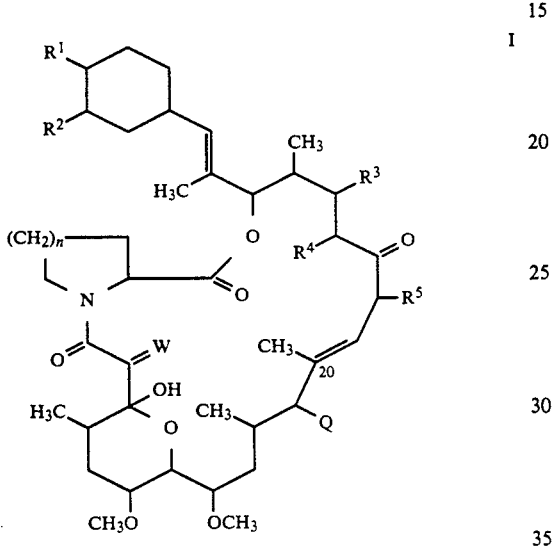

or a pharmaceutically acceptable salt thereof, wherein:
$R^1$ and $R^2$ are independently selected from:
1) —$N_3$;
2) —NHCN;
3) —$NR^6R^7$, wherein $R^6$ and $R^7$ independently, are
   a) hydrogen,
   b) $C_{1-12}$ alkyl, unsubstituted or substituted with $R^8$ and $R^9$, wherein $R^8$ and $R^9$ are independently selected from the group consisting of:
      i) hydrogen,
      ii) —OH,
      iii) $C_{1-6}$ alkoxy,
      iv) —O—CO—$C_{1-6}$alkyl,
      v) —$NR^{10}R^{11}$, wherein $R^{10}$ and $R^{11}$ are independently, hydrogen, or $C_{1-6}$alkyl, unsubstituted or substituted with phenyl
      vi) —$CONR^{10}R^{11}$,
      vii) —$CO_2H$,
      viii) —CO—O—$C_{1-6}$alkyl,
      ix) —S—$C_{1-6}$alkyl,
      x) —SO—$C_{1-6}$alkyl,
      xi) —$SO_2$—$C_{1-6}$alkyl,
      xii) halo,
      xiii) —$C_{3-7}$-cycloalkyl,
      xiv) phenyl, unsubstituted or substituted with X, Y and Z,
      xv) naphthyl, unsubstituted or substituted with X, Y and Z,
      xvi) —$CF_3$,
   c) $C_{3-12}$-alkenyl, unsubstituted or substituted with $R^8$ and $R^9$, wherein $R^8$ and $R^9$ are as defined above,
   d) $C_{3-7}$ cycloalkyl, unsubstituted or substituted with $R^8$ and $R^9$, wherein $R^8$ and $R^9$ are as defined above,
   e) phenyl, unsubstituted or substituted with X, Y and Z,
   f) naphthyl, unsubstituted or substituted with X, Y and Z,
   g) —$SO_2$-phenyl, wherein phenyl is unsubstituted or substituted with X, Y and Z,
   h) —$SO_2$—$C_{1-6}$alkyl,
   i) or where $R^6$ and $R^7$ and the N to which they are attached may form a heterocyclic ring selected from the group consisting of: morpholine, thiomorpholine, piperidine, and piperazine, and where the substituent(s), attached to the carbon atom(s) in the heterocyclic ring is/are independently selected from the group consisting of:
      i) hydrogen,
      ii) —OH,
      iii) $C_{1-6}$ alkoxy,
      iv) —O—CO—$C_{1-6}$ alkyl,
      v) —$NR^{10}R^{11}$, wherein $R^{10}$ and $R^{11}$ are as defined above,
      vi) —$CONR^{10}R^{11}$,
      vii) —$CO_2H$,
      viii) —CO—O—$C_{1-6}$ alkyl,
      ix) —SH,
      x) halo,
      xi) phenyl, unsubstituted or substituted with X, Y and Z,
      xii) naphthyl, unsubstituted or substituted with X, Y and Z,
      xiii) —$CF_3$;
4) —$N(R^6)CO$—O—$R^{12}$, wherein $R^6$ is as defined above and $R^{12}$ is $C_{1-12}$ alkyl, unsubstituted or substituted with $R^8$ and $R^9$, wherein $R^8$ and $R^9$ are as defined above;
5) —$N(R^6)CO$—$R^{13}$, wherein $R^6$ is as defined above and $R^{13}$ is
   a) hydrogen,
   b) $C_{1-12}$ alkyl, unsubstituted or substituted with $R^8$ and $R^9$, wherein $R^8$ and $R^9$ are as defined above,
   c) $C_{3-12}$ cycloalkyl, unsubstituted or substituted with $R^8$ and $R^9$, wherein $R^8$ and $R^9$ are as defined above,
   d) phenyl, unsubstituted or substituted with X, Y and Z,
   e) naphthyl, unsubstituted or substituted with X, Y and Z, or
   f) where $R^6$ and $R^{13}$ and the —NCO— to which they are attached may form an unsubstituted or substituted 5- to 7-membered heterocyclic ring which may include one or two additional heteroatoms independently selected from the group consisting of O, S, or $NR^{10}$, wherein $R^{10}$ is as defined above;
6) —$N(R^{14})COCH(R^{22})NR^6R^7$ wherein $R^6$ and $R^7$ are as defined above, $R^{14}$ is selected from the definitions of $R^6$, and $R^{22}$ is
   a) hydrogen,
   b) $C_{1-4}$ alkyl, unsubstituted or substituted with $R^{23}$, wherein $R^{23}$ is selected from the group consisting of:
      i) —OH,
      ii) $C_{1-6}$ alkoxy,
      iii) —O—CO—$C_{1-6}$ alkyl, iv) —SH,
v) —S—$C_{1-6}$ alkyl,
vi) —$NR^{10}R^{11}$, wherein $R^{10}$ and $R^{11}$ are as defined above,
vii) —$CO_2H$,
viii) —$CONH_2$,
ix) imidazolyl,
x) indolyl,
xi) phenyl, and
xii) p-hydroxyphenyl, or
c) phenyl;

7) —$N(R^{14})CO(CH_2)_mNR^6R^7$, wherein m is 0 or 2-6, $R^6$ and $R^7$ are as defined above, and $R^{14}$ is selected from the definitions of $R^6$, or where $R^{14}$ and $R^6$ and the —$NCO(CH_2)_mN$— to which they are attached may form an unsubstituted or substituted 5- to 7-membered heterocyclic ring;

8) —$N=C(R^{14})$—$NR^6R^7$, wherein $R^6$ and $R^7$ are as defined above, and $R^{14}$ is selected from the definitions of $R^6$, and wherein if either $R^6$ or $R^7$ are hydrogen, the tautomeric structure —$NHC(R^{14})=NR^{6 \text{ or } 7}$ is also possible;

9) —$N(R^{15})_3^+A^-$, wherein $R^{15}$ is $C_{1-6}$ alkyl, unsubstituted or substituted with phenyl or naphthyl, and wherein $A^-$ is a counterion selected from the group consisting of: acetate, adipate, benzoate, benzenesulfonate, bisulfate, butyrate, citrate, camphorate, camphorsulfonate, ethanesulfonate, fumarate, hemisulfate, hemitartrate, heptaonate, hexanoate, chloride, bromide, iodide, methanesulfonate, lactate, maleate, methanesulfonate 2-naphthalenesulfonate, nitrate, oxalate, pamoate, perchlorate, persulfate, picrate, pivalate, propionate, succinate, tartrate, tosylate, and undecanoate; and

10)

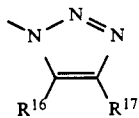

wherein $R^{16}$ and $R^{17}$ are independently,
a) hydrogen,
b) phenyl, unsubstituted or substituted with X, Y and Z,
c) naphthyl, unsubstituted or substituted with X, Y and Z,
d) —CN,
e) —$CF_3$,
f) —CO—$C_{1-6}$alkyl, or
g) —CO—O—$C_{1-6}$alkyl;

11) $C_{1-10}$ alkoxy;
12) substituted $C_{1-10}$ alkoxy in which one or more substituent(s) is(are) selected from:
a) hydroxy,
b) $C_{1-6}$ alkoxy,
c) phenyl $C_{1-3}$ alkoxy,
d) substituted phenyl $C_{1-3}$ alkoxy, in which the substituents on phenyl are X, Y and Z,
e) —$OCOC_{1-6}$ alkyl,
f) —$NR^{10}R^{11}$, wherein $R^{10}$ and $R^{11}$ are as defined above,
g) —$NR^6COC_{1-6}$ alkyl, wherein $R^6$ is as defined above,
h) —$COOR^6$, wherein $R^6$ is as defined above,
i) —CHO,
j) phenyl,
k) substituted phenyl in which the substituents are X, Y and Z,
l) phenyloxy,
m) substituted phenyloxy in which the substituents are X, Y and Z,
n) 1- or 2-naphthyl,
o) substituted 1- or 2-naphthyl in which the substituents are X, Y and Z,
p) biphenyl, and
q) substituted biphenyl in which the substituents are X, Y and Z;

13) $C_{3-10}$ alkenyloxy;
14) substituted $C_{3-10}$ alkenyloxy in which one or more substituent(s) is(are) selected from:
a) hydroxy,
b) $C_{1-6}$ alkoxy,
c) —OCO—$C_{1-6}$ alkyl,
d) $C_{2-8}$ alkenyl,
e) phenyl,
f) substituted phenyl in which the substituents are X, Y and Z,
g) 1- or 2-naphthyl,
h) substituted 1- or 2-naphthyl in which the substituents are X, Y and Z,
i) biphenyl, and
j) substituted biphenyl in which the substituents are X, Y and Z;

15) $C_{3-10}$ alkynyloxy; and
16) substituted $C_{3-10}$ alkynyloxy in which one or more substituent(s) is(are) selected from:
a) hydroxy,
b) $C_{1-6}$ alkoxy,
c) —OCO—$C_{1-6}$ alkyl,
d) phenyl,
e) substituted phenyl in which the substituents are X, Y and Z,
f) 1- or 2-naphthyl,
g) substituted 1- or 2-naphthyl in which the substituents are X, Y and Z,
h) biphenyl, and
i) substituted biphenyl in which the substituents are X, Y and Z;

17) phenyloxy;
18) substituted phenyloxy in which the substituents are X, Y and Z;
19) 1- or 2- naphthyloxy;
20) substituted 1- or 2-naphthyloxy in which the substituents are X, Y and Z;
21) biphenyloxy;
22) substituted biphenyloxy in which the substituents are X, Y and Z; and
23) hydroxy; or
24) where $R^1$ and $R^2$ may be both connected to form a 3- to 7-membered heterocyclic ring of the form;

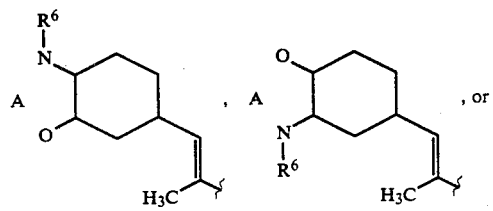

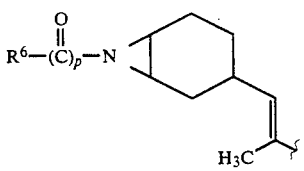

wherein p is zero or one, R⁶ is as defined above, and A is
a) —CO—,
b) —CS—,
c) —CO—$C_1$-alkyl,
d) —CS—$C_1$-alkyl, or
e) —$C_{1-2}$—alkyl, wherein the alkyl may be unsubstituted or substituted with one or more of the following:
 i) —OH,
 ii) $C_{1-6}$ alkyl,
 iii) $C_{1-6}$ alkoxy,
 iv) —O—CO—$C_{1-6}$ alkyl,
 v) —$NR^9R^{10}$, wherein $R^9$ and $R^{10}$ are as defined above,
 vi) —$CONR^9R^{10}$,
 vii) —$CO_2H$,
 viii) —CO—O—$C_{1-6}$ alkyl,
 ix) —S—$C_{1-6}$ alkyl,
 x) —SO—$C_{1-6}$ alkyl,
 xi) —$SO_2$—$C_{1-6}$ alkyl,
 xii) halo,
 xiii) phenyl, unsubstituted or substituted with X, Y or Z, or
 xiv) naphthyl unsubstituted or substituted with X, Y or Z;

$R^3$ is hydrogen, hydroxy, or $C_{1-6}$ alkoxy;
$R^4$ is hydrogen, or $R^3$ and $R^4$ taken together form a double bond;
$R^5$ is methyl, ethyl, propyl or allyl;
Q is F or OH, with the proviso that if Q is OH, $R^2$ is other than OH or $OCH_3$;
W is O or (H, OH);
X, Y and Z independently are selected from:
 a) hydrogen,
 b) $C_{1-7}$ alkyl,
 c) $C_{2-6}$ alkenyl,
 d) halo, such as Cl, Br, F or I,
 e) —$(CH_2)_t$—$NR^{10}R^{11}$, wherein $R^{10}$ and $R^{11}$ are as defined above, and t is 0 or 2,
 f) —CN,
 g) —CHO,
 h) —$CF_3$,
 i) —$SR^{18}$, wherein $R^{18}$ is hydrogen, $C_{1-6}$ alkyl, or phenyl,
 j) —$SOR^{18}$, wherein $R^{18}$ is as defined above,
 k) —$SO_2R^{18}$, wherein $R^{18}$ is as defined above,
 l) —$CONR^{10}R^{11}$, wherein $R^{10}$ and $R^{11}$ are as defined above,
 m) $R^{19}O(CH_2)t$—wherein $R^{19}$ is hydrogen, $C_{1-3}$ alkyl, hydroxy-$C_{2-3}$alkyl, phenyl or naphthyl and t is as defined above;
 n) —$CH(OR^{20})(OR^{21})$, wherein $R^{20}$ and $R^{21}$ are $C_{1-3}$ alkyl or taken together form an ethyl or propyl bridge,
 o)

wherein $R^{19}$ and t are as defined above; and
p)

wherein $R^{19}$ and t are as defined above;
or any two of X, Y and Z may be joined to form a saturated ring selected from dioxolanyl and dioxanyl; and
n is 1 or 2.

2. A compound according to claim 1 wherein the steric configuration of formula I is as defined in formula III:

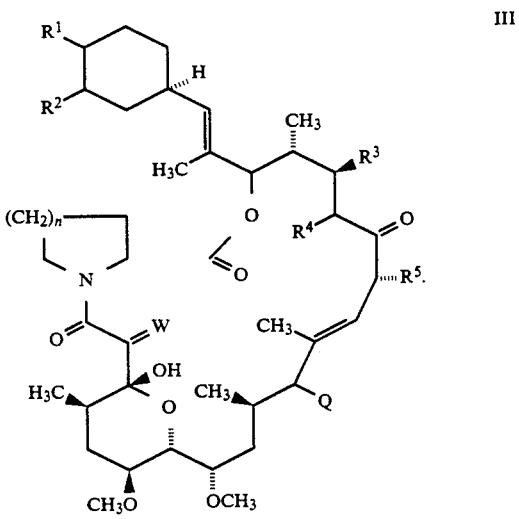

3. The compound according to claim 1 wherein:
$R^1$ and $R^2$ are independently selected from:
 1) —$N_3$;
 2) —$NR^6R^7$, wherein $R^6$ and $R^7$ independently, are,
  a) hydrogen,
  b) $C_{1-12}$alkyl, unsubstituted or substituted with $R^8$ and $R^9$, wherein $R^8$ and $R^9$ are independently selected from the group consisting of:
   i) hydrogen,
   ii) —OH,
   iii) —O—CO—$C_{1-6}$ alkyl,
   iv) —$NR^{10}R^{11}$, wherein $R^{10}$ and $R^{11}$ are independently, hydrogen, or $C_{1-6}$alkyl, unsubstituted or substituted with phenyl
   v) —$CONR^{10}R^{11}$,
   vi) —$CO_2H$,
   vii) —CO—O—$C_{1-6}$alkyl, and
   viii) phenyl, unsubstituted or substituted with X, Y and Z,
  c) $C_{3-12}$alkenyl, unsubstituted or substituted with $R^8$ and $R^9$, wherein $R^8$ and $R^9$ are as defined above,
  d) or where $R^6$ and $R^7$ and the N to which they are attached may form a heterocyclic ring selected from: morpholine, thiomorpholine, piperidine, and piperizine, and where the substituent(s), attached to the carbon atoms(s) in the heterocyclic ring is/are independently selected from the group consisting of:
  i) hydrogen,
  ii) —OH,
  iii) —O—CO—$C_{1-6}$alkyl,
  iv) —CONR$^{10}$R$^{11}$,
  v) —CO$_2$H,
  vi) —CO—O—$C_{1-6}$alkyl, and
  vii) phenyl, unsubstituted or substituted with X, Y and Z;
3) —N(R$^6$)CO—O—R$^{12}$, wherein R$^6$ is as defined above and R$^{12}$ is $C_{1-12}$alkyl, unsubstituted or substituted with R$^8$ and R$^9$, wherein R$^8$ and R$^9$ are as defined above;
4) —N(R$^6$)CO—R$^{13}$, wherein R$^6$ is as defined above and R$^{13}$ is
  a) hydrogen,
  b) $C_{1-12}$alkyl, unsubstituted or substituted with R$^8$ and R$^9$, wherein R$^8$ and R$^9$ are as defined above,
  c) $C_{3-12}$cycloalkyl, unsubstituted or substituted with R$^8$ and R$^9$, wherein R$^8$ and R$^9$ are as defined above, or
  d) phenyl, unsubstituted or substituted with X, Y and Z;
5) —N(R$^{14}$)COCH(R$^{22}$)NR$^6$R$^7$ wherein R$^6$ and R$^7$ are as defined above, R$^{14}$ is selected from the definitions of R$^6$, and R$^{22}$ is
  a) hydrogen,
  b) $C_{1-4}$ alkyl, unsubstituted or substituted with R$^{23}$, wherein R$^{23}$ is selected from the group consisting of
    i) —OH,
    ii) $C_{1-6}$alkoxy,
    iii) —O—CO—$C_{1-6}$alkyl,
    iv) —SH,
    v) —S—$C_{1-6}$alkyl,
    vi) —NR$^{10}$R$^{11}$, wherein R$^{10}$ and R$^{11}$ are as defined above,
    vii) —CO$_2$H,
    viii) —CONH$_2$,
    ix) imidazolyl,
    x) indolyl,
    xi) phenyl, and
    xii) p-hydroxyphenyl, or
  c) phenyl;
6) —N(R$^{14}$)CO(CH$_2$)$_m$NR$^6$R$^7$, wherein m is 0 or 2–6, R$^6$ and R$^7$ are as defined above, and R$^{14}$ is selected from the definitions of R$^6$, or wherein R$^{14}$ and R$^6$ and the —NCO(CH$_2$)$_m$N— to which they are attached may form an unsubstituted or substituted 5- to 7-membered heterocyclic ring, such as 2-imidazolidone;
7) —N=C(R$^{14}$)—NR$^6$R$^7$, wherein R$^6$ and R$^7$ are as defined above, and R$^{14}$ is selected from the definitions of R$^6$, and wherein if either R$^6$ or R$^7$ are hydrogen, the tautomeric structure —NHC(R$^{14}$)=NR$^{6or7}$ is also possible;
8) —N(R$^{15}$)$_3$$^+$ A$^-$, wherein R$^{15}$ is $C_{1-6}$ alkyl, unsubstituted or substituted with phenyl or naphthyl, and wherein A$^-$ is a counterion selected from the group consisting of: acetate, adipate, benzoate, benzenesulfonate, bisulfate, butyrate, citrate, camphorate, camphorsulfonate, ethanesulfonate, fumarate, hemisulfate, hemitartrate, heptanoate, hexanoate, chloride, bromide, iodide, methanesulfonate, lactate, maleate, methanesulfonate, 2-naphthalene-sulfonate, nitrate, oxalate, pamoate, perchlorate, persulfate, picrate, pivalate, propionate, succinate, tartrate, tosylate, and undecanoate; and

9)

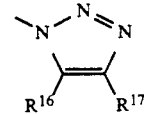

wherein R$^{16}$ and R$^{17}$ are independently,
  a) hydrogen,
  b) phenyl, unsubstituted or substituted with X, Y and Z,
  c) naphthyl, unsubstituted or substituted with X, Y and Z,
  d) —CN,
  e) —CF$_3$,
  f) —CO—$C_{1-6}$alkyl, or
  g) —CO—$C_{1-6}$alkyl;
10) $C_{1-10}$alkoxy;
11) substituted $C_{1-10}$alkoxy in which one or more substituent(s) is(are) selected from:
  a) hydroxy,
  b) $C_{1-6}$alkoxy,
  c) phenyl $C_{1-3}$alkoxy,
  d) substituted phenyl $C_{1-3}$alkoxy, in which the substituents on phenyl are X, Y and Z,
  e) —OCOC$_{1-6}$ alkyl,
  f) —NR$^{10}$R$^{11}$, wherein R$^{10}$ and R$^{11}$ are as defined above,
  g) —NR$^6$CO—C$_{1-6}$ alkyl, wherein R$^6$ is as defined above,
  h) —COOR$^6$, wherein R$^6$ is as defined above,
  i) —CHO,
  j) phenyl,
  k) substituted phenyl in which the substituents are X, Y and Z,
  l) phenyloxy, and
  m) substituted phenyloxy in which the substituents are X, Y and Z;
12) $C_{3-10}$ alkenyloxy;
13) substituted $C_{3-10}$ alkenyloxy in which one or more substituent(s) is(are) selected from:
  a) hydroxy,
  b) $C_{1-6}$ alkoxy,
  c) —OCO—$C_{1-6}$ alkyl,
  d) $C_{2-8}$ alkenyl,
  e) phenyl, and
  f) substituted phenyl in which the substituents are X, Y and Z;
14) $C_{3-10}$ alkynyloxy;
15) substituted $C_{3-10}$ alkynyloxy in which one or more substituent(s) is(are) selected from:
  a) hydroxy,
  b) $C_{1-6}$ alkoxy,
  c) —OCO—$C_{1-6}$ alkyl,
  d) phenyl, and
  e) substituted phenyl in which the substituents are X, Y and Z;
16) phenyloxy;
17) substituted phenyloxy in which the substituents are X, Y and Z;
18) 1- or 2-naphtyloxy;

19) substituted 1- or 2-naphthyloxy in which the substituents are X, Y and Z; and
20) hydroxy; or
21) wherein $R^1$ and $R^2$ may both connected to form a 3- to 7-membered heterocyclic ring of the form:

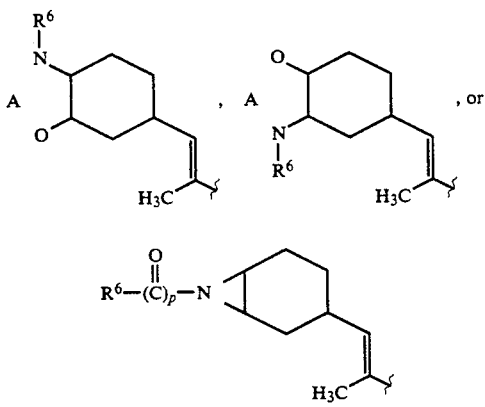

wherein p is one, $R^6$ is as defined above, and A is
a) —CO—,
b) —CO—$C_1$-alkyl, or
c) $C_{1-2}$-alkyl;

$R^3$ is hydrogen or hydroxy;
$R^4$ is hydrogen;
$R^5$ is ethyl, propyl or allyl;
Q is F or OH, with the proviso that if Q is OH, $R^2$ is other than OH or $OCH_3$;
W is O or (H, OH);
X, Y and Z independently are selected from:
a) hydrogen,
b) $C_{1-7}$ alkyl,
c) $C_{2-6}$ alkenyl,
d) halo, such as Cl, Br, F or I,
e) —CHO,
f) —$CONR^{10}R^{11}$, wherein $R^{10}$ and $R^{11}$ are as defined above,
g) $R^{19}O(CH_2)_t$— wherein $R^{19}$ is hydrogen, $C_{1-3}$ alkyl, hydroxy-$C_{2-3}$alkyl, phenyl or naphthyl and t is 0 to 2;
h) —$CH(OR^{20})(OR^{21})$, wherein $R^{20}$ and $R^{21}$ are $C_{1-3}$ alkyl or taken together form an ethyl or propyl bridge,
i)

wherein $R^{19}$ and t are as defined above; and
j)

wherein $R^{19}$ and t are as defined above;
or any two of X, Y and Z may be joined to form a saturated ring selected from dioxolanyl or dioxanyl; and
n is 1 or 2,
or a pharmaceutically acceptable salt thereof.

4. A compound which is selected from the group consisting of:
17-Ethyl-20-fluoro-1-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-teteeone;
17-Ethyl-20-fluoro-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;
17-Ethyl-20-fluoro-1-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;
17-Ethyl-20-fluoro-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;
17-Ethyl-20-fluoro-1-hydroxy-12-[2'-(3'',4''-dihydroxycyclohexyl)-23,25-dimethoxy-13,19,21,27-tetramethyl-11,28-dioxa-4-azatricyclo[22.3.1.0⁴,⁹]octacos-18-ene-2,3,10,16-tetraone;
17-Ethyl-20-fluoro-1,14-dihydroxy-12-[2'-(3'',4''-dihydroxy-cyclohexyl)-23,25-dimethoxy-13,19,21,27-tetramethyl-11,28-dioxa-4-azatricyclo[22.3.1.0⁴,⁹]octacos-18-ene-2,3,10,16-tetraone;
17-Ethyl-20-fluoro-1-hydroxy-12-[2'-(4''-azido-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;
17-Ethyl-20-fluoro-1-hydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;
17-Ethyl-20-fluoro-1,14-dihydroxy-12-[2'-(4''-azido-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;
17-Ethyl-20-fluoro-1,14-dihydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;
17-Ethyl-20-fluoro-1,14-dihydroxy-12-[2'-(4''-acetylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;
17-Ethyl-20-fluoro-1,14-dihydroxy-12-[2'-(4''-N-(2-propenyl)-amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;
17-Ethyl-20-fluoro-1,14-dihydroxy-12-[2'-(4''-N-methylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;
17-Ethyl-20-fluoro-1-hydroxy-12-[2'-(4''-methylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-1'''-adamantane-carboxamido-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-cyclopropanecarboxamid-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-formamido-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-{2'-(4''-(4''',5'''-dicarboethoxy-1''',2''',3'''-triazole)-3''-methoxycyclohexyl)-1'-methylvinyl}-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-acetyl amino-3''-methoxy-cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-amino-3''-hydroxy-cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(3''-amino-4''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-20-fluoro-1,14-dihydroxy-12-[2'-(4''-azido-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-20-fluoro-1,14-dihydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-20-fluoro-1,14-dihydroxy-12-[2'-(4''-acetylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-20-fluoro-1-hydroxy-12-[2'-(4''-amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-20-fluoro-1-hydroxy-12-[2'-(4''-acetylamino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-20-fluoro-1,14-dihydroxy-12-[2'-(4''-amino-3''-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-20-fluoro-1,14-dihydroxy-12-[2'-(4''-hydroxy-3''-aminocyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-beta-amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-alpha-amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-beta-amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-alpha-amino-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-amino-3''-isopropyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-amino-3''-isopropyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-amino-3''-n-propyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-amino-3''-n-propyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-amino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-amino-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-methylcarbamate-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-benzylcarbamate-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-acetamidine-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4"-benza midine-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4"-forma midine-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-(L-phenylalanyl)-amido-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4"-(L-phenylalanyl)amido-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2"-(4"-(D-phenylalanyl)-amido-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4"-(D-phenylalanyl)amido-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2"-(4"-(aminoacetyl-amino)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4"-(aminoacetyl amino)-3"-methoxycyclohexyl)-4'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-(2-hydroxypropyl-amino)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4"-(2-hydroxypropylamino)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(1-aza-4-oxabicyclo-[4.4.0]dec-6-yl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1-hydroxy-12-[2'-(1-aza-4-oxabicyclo[4.4.0]-dec-6-yl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-Ethyl-20-fluoro-1,14-dihydroxy-12-[2'-(4"-trimethy lamino-3"methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone Iodide;

17-Allyl-20-fluoro-1,14-dihydroxy-12-[2'-(4"-amino-3"-isopropoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-20-fluoro-1-hydroxy-12-[2'-(4"-amino-3"-isopropoxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-Propyl-20-fluoro-1-hydroxy-12-[2'-(4"-amino-3"-propyloxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-Ethyl-20-fluoro-1,14-dihydroxy-12-[2'-(4"-acetylamino-3"-isopropoxycyclohexyl)-1'-methylvinyl]-23,25-dimethoxy-13,19,21,27-tetramethyl-11,28-dioxa-4-azatricyclo-[22.31.0⁴,⁹]octacos-18-ene-2,3,20,26-tetraone;

17-Ethyl-20-fluoro-1,14-dihydroxy-12-[2'-[4"-(N'-t-butoxycarbonyl-D-phenylalanine)amido-3"-n-propyloxycyclohexyl]-1'-methylvinyl]-23,25-dimethoxy-13,19,21,27-tetra-methyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-[4"-(N'-t-butoxycarbonyl-L-phenylalanine)amido-3"-n-propyloxycyclohexyl]-1'-methylvinyl]-23,25-dimethoxy-13,19,21,27-tetra-methyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-acetoxyacetylamino-3"-ethoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1,14-dihydroxy-12-[2'-(4"-(1'"'-adamantanecarboxamido)-3"-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-cyclopropanecarbox-amido-3"-isopropyloxycyclohexyl)-1'-methylvinyl]-23,25-dimethoxy-13,19,21,27-tetramethyl-11,28-dioxa-4-aza-tricyclo[22.3.1.0⁴,⁹]octacos-18-ene-2,3,10,16-tetraone;

17-Ethyl-20-fluoro-1,14-dihydroxy-12-[2-(4"-form amido-3"-n-propyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1,14-dihydroxy-12-{2'-[4'",5'"-dicarboeth-oxy-1'",2'",3'"-triazole)-3"-n-propyloxycyclohexyl]-1'-methyl-vinyl}-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4"-amino-3"-ethoxycyclo-hexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-Ethyl-20-fluoro-1,14-dihydroxy-12-[2'-(4"-benzylamino-3"-isopropyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1,14-dihydroxy-12-[2'-(4"-trimethy lamino-3"-ethoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone-Iodide;

17-Ethyl-20-fluoro-1,2,14-trihydroxy-12-[2'-(4''-acetylamino-3''-n-propyloxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-3,10,16-trione;

17-Ethyl-20-fluoro-1,14-dihydroxy-12-{2'-[4''-(N'-phenylaminocarbonyl)amino-3''-isopropyloxycyclohexy]-1'-methylvinyl}-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-{2'-[4''-(ethoxycarbonyl)-amino-3''-n-propyloxycyclohexyl]-1'-methylvinyl}-23,25-dimethoxy-13,19,21,27-tetramethyl-11,28-dioxa-4-azatricyclo[22.3.1.0$^{4,9}$]octacos-18-ene-2,3, 10,16-tetraone;

17-Ethyl-20-fluoro-1-hydroxy-12-[2'-(4''-acetylamino-3''-n-propyl-oxycyclohexyl)-1'-methylvinyl]-23,25-dimethoxy-13,19,21,27-tetramethyl-11,28-dioxa-4-azatricyclo-[22.3.1.0$^{4,9}$]-octacos-18-ene-2,3,10,16-tetraone;

17-Ethyl-20-fluoro-1,14-dihydroxy-12-[2'-(4''-dimethylamino-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1-hydroxy-12-[2'-(4''-dimethylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-benzylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4''-benzylamino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4''-dimethylamino-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4''-dimethylamino-3''-n-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4''-benzylamino-3''-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4''-benzylamino-3''-n-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4''-(2-phenyl-2-hydroxyethyl)amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4''-morpholino-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone;

17-Ethyl-20-fluoro-1,14-dihydroxy-12-[2'-(4''-morpholino-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1-hydroxy-12-[2'-(4''-amino-3''-n-butyloxycyclo-hexyl)-1'-methylvinyl]-23,25-dimethoxy-1,3,19,21,27-tetramethyl-11,18-dioxa-4-azatricyclo[22.3.1.0$^{4,9}$]-octacos-18-ene-2,3,10,16-tetraone;

17-Ethyl-20-fluoro-1,14-dihydroxy-12-[2'-(4''-amino-3''-butyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4''-amino-3''-(3-methylbutyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-amino-3''-(3-methylbutyloxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1-hydroxy-12-[2'-(4''-amino-3''-(2-methylbutyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-amino-3''-(2-methylbutyloxy)cyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1-hydroxy-12-[2'-(4''-(N-(2-methyl-3-(4-hydroxy-phenyl)propenyl)amino-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone;

17-Ethyl-20-fluoro-1,14-dihydroxy-12-[2'-(4''-(N-(2-methyl-3-(4-hydroxyphenyl)propenyl)amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-1-2-[2'-(4''-(N-(3-(4-hydroxyphenyl)-propenyl)amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4''-(N-(3-(4-hydroxyphenyl)propenyl)amino-3''-methoxycyclohexyl)-1'-methylvinyl]-23,25-dimethoxy-13,19,21,27-tetramethyl-11,28-dioxa-4-azatricyclo[22.3.1.0$^{3,9}$]octacos-18-ene-2,3,10,16-tetraone;

17-Ethyl-20-fluoro-1,14-dihydroxy-12-[2'-(4''-(N-3-phenylpropenyl)amino-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1-hydroxy-12-[2'-(4''-(N-3-phenylpropenyl)-amino-3''-methoxycyclohexyl)-1'-methylvinyl]-23,25-dimethoxy-13,19,21,27-tetramethyl- 11,28-dioxa-4-azatricyclo[22.3.1.0$^{4,9}$]octacos-18-ene-2,3,10,16-tetraone;

17-Ethyl-20-fluoro-1-hydroxy-12-[2'-(4"-(L-Trp)amido-3"-methoxycyclohexyl)-1'-methoxyvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-phenyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(3"-phenyloxy-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-phenyloxy-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(4'''-fluorophenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(4'''-chlorophenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(4'''-methylphenyl-oxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(3"-(4'''-methylphenyloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(4'''-methylphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(4'''-phenoxyphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(4'''-phenoxyphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(3"-(4'''-phenoxyphenyloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(napth-1-yloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1,14-dihydroxy-12-[2'-(3"-(napth-1-yloxy)-4"-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1,14-dihydroxy-12-[2'-(4"-(napth-1-yloxy)-3"-hydroxycyclohexyl)-1'''-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(napth-2-yloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1,14-dihydroxy-12-[2'-(4"-(napth-2-yloxy)-3"-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1,14-dihydroxy-12-[2'-(3"-napth-2-yloxy)-4"-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1-hydroxy-12-[2'-(4"-(napth-2-yloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-20-fluoro-1,14-dihydroxy-12-[2'-(4"-(6'''-methoxynaphth-2-yloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(3"-(6'''-methoxynaphth-2-yloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(6'''-methoxynaphth-2-yloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(3"-(4'''-methoxyphenyloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(4'''-methoxyphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(3"-(3'''-methoxyphenyloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(4"-(3'''-methoxyphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-20-fluoro-1,14-dihydroxy-12-[2'-(3"-(4'''-hydroxyphenyloxy)-4"-hydroxycyclohexyl)-1'-methylvinyl]-23,25-dimethoxy-13,19,21,27-tetramethyl- 11,28-dioxa-4-azatricyclo[22.3.1.0^4,9]octacos-18-ene-2,3,10,16-tetraone;

17-Ethyl-20-fluoro-1,14-dihydroxy-12-[2'-(4'''-(4''''-hydroxyphenyloxy)-3''-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-20-fluoro-1,14-dihydroxy--12-[2'-(4''-(6'''-hydroxynaphth-2-yloxy)-3''-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-20-fluoro-1,14-dihydroxy--12-[2'-(3''-(6'''-hydroxynaphth-2-yloxy)-4''-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-20-fluoro-1,14-dihydroxy-12--[2'-(4''-(3''',4''''-dichlorophenyloxy)-3''-methoxycyclohexyl)-1'-methylvinyl]-23,25-dimethoxy-13,19,21,27-tetramethyl-11,28-dioxa-4-azatricyclo]22.3.1.0^4,9]octacos-18-ene-2,3,10,16-tetraone;

17-Ethyl-20-fluoro-1,14-dihydroxy-12-[2'-(4''-(phenanthr-9-yl)-3''-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-20-fluoro-1,14-dihydroxy-12-[2'-(-4''-(3''',4'''-methylenedioxyphenyloxy)-3''-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-20-fluoro-1,14-dihydroxy-12-[2'-(4''-(-2''',3'''-dihydrobenzofuran-5-yl)-3''-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Allyl-20-fluoro-1,14-dihydroxy-12-[2'-(4''-(naphth-2-yl)-3''-methoxycyclohexyl)-1'-methylvinyl]-23,25-dimethoxy-13,19,21,27-tetramethyl-11,28-dioxa-4-azatricyclo-[22.3.1.0^4,9]octacos-18-ene-2,3,10,16-tetraone;

17-Ethyl-20-fluoro-1,14-dihydroxy-12-[2'-(-4''-(1''',4'''-benzodioxane-6-yl)-3''-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-20-fluoro-1,2,14-trihydroxy-12-[2'-(4''-(naphth-2-yl)-3''-methoxycyclohexyl)-1'-methylvinyl]-23,25-dimethoxy-13,19,21,27-tetramethyl-11,28-dioxa-4-azatricyclo-[22.3.1.0^4,9]octacos-18-ene-3,10,16-trione;

17-Ethyl-20-fluoro-1,14-dihydroxy-12-[2'-(4''-allyloxy-3''-methoxycyclohexyl)-1'-methylvinyl]23,25-dimethoxy-13,19,21,27-tetramethyl-11,28-dioxa-4-azatricyclo-[22.3.1.0^4,9]octacos-18-ene-2,3,10,16-tetraone;

17-Ethyl-20-fluoro-1,14-dihydroxy-12-[2'-(4''-(2-butynyloxy)-3''-methoxycyclohexyl)-1'-methylvinyl]-23,25-dimethoxy-13,19,21,27-tetramethyl-11,28-dioxa-4-azatricyclo-[22.3.1.0^4,9]octacos-18-ene-2,3,10,16-tetraone;

17-Ethyl-20-fluoro-1,14-dihydroxy-12-[2'-(4''-cinnamyloxy-3''-methoxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-20-fluoro-1,14-dihydroxy-12-[2'-(3''-methoxy-4''-phenylpropyloxycyclohexyl)-1'-methylvinyl]-23,25-dimethoxy-13,19,21,27-tetramethyl-11,28-dioxa-4-azatricyclo-[22.3.1.0^4,9]octacos-18-ene-2,3,10,16-tetraone;

17-Ethyl-20-fluoro-1,14-dihydroxy-12-[2'-(4''-allyloxy-3''-hydroxycyclohexyl)-1'-methylvinyl]-23,25-dimethoxy-13,19,21,27-tetramethyl-11,28-dioxa-4-azatricyclo-[22.3.1.0^4,9]octacos-18-ene-2,3,10,16-tetraone;

17-Ethyl-20-fluoro-1,14-dihydroxy-12-[2'-(3''-allyloxy-4''-hydroxycyclohexyl)-1'-methylvinyl]-23,25-dimethoxy-13,19,21,27-tetramethyl-11,28-dioxa-4-azatricyclo-[22.3.1.0^4,9]octacos-18-ene-2,3,10,16-tetraone;

17-Ethyl-20-fluoro-1,14-dihydroxy-12-[2'-(3''-hydroxy-4''-isopropyloxycyclohexyl)-1'-methylvinyl]23,25-dimethoxy-13,19,21,27-tetramethyl-11,28-dioxa-4-azatricyclo-[22.3.1.0^4,9]octacos-18-ene-2,3,10,16-tetraone;

17-Ethyl-20-fluoro-1,14-dihydroxy-12-[2'-(4''-hydroxy-3''-isopropyloxycyclohexyl)-1'-methylvinyl]-23,25-dimethoxy-13,19,21,27-tetramethyl-11,28-dioxa-4-azatricyclo-[22.3.1.0^4,9]octacos-18-ene-2,3,10,16-tetraone;

17-Ethyl-20-fluoro-1,14-dihydroxy-12-[2'-(4''-sec-butenyloxy-3''-hydroxycyclohexyl)-1'-methylvinyl]-23,25-dimethoxy-13,19,21,27-tetramethyl-11,28-dioxa-4-azatricyclo-[22.3.1.0^4,9]octacos-18-ene-2,3,10,16-tetraone;

17-Ethyl-20-fluoro-1,14-dihydroxy-12-[2'-(3''-sec-butenyloxy-4''-hydroxycyclohexyl)-1'-methylvinyl]-23,25-dimethoxy-13,19,21,27-tetramethyl-11,28-dioxa-4-azatricyclo-[22.3.1.0^4,9]octacos-18-ene-2,3,10,16-tetraone;

17-Ethyl-20-fluoro-1,14-dihydroxy-12-[2'-(4''-trans-2-butenyloxy)-3''-hydroxycyclohexyl)-1'-methylvinyl]-23,25-dimethoxy-13,19,21,27-tetramethyl-11,28-dioxa-4-azatricyclo]22.3.1.0^4,9]octacos-18-ene-2,3,10,16-tetraone;

17-Ethyl-20-fluoro-1,14-dihydroxy-12-[2'-(3''-trans-2-butenyloxy)-4''-hydroxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetrane;

17-Ethyl-20-fluoro-1,14-dihydroxy-12-[2'-(3''-hydroxy-4''-(3-methyl-2-butenyloxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-20-fluoro-1,14-dihydroxy-12-[2'-(4''-hydroxy-3''-(3-methyl-2-butenyloxycyclohexyl)-1'-methylvinyl]-23,25-dimethoxy-13,29,21,27-tetramethyl-11,28-dioxa-4-azatricyclo[22.3.1.0^4,9]octacos-18-ene-2,3,10,16-tetraone;

17-Ethyl-20-fluoro-1,14-dihydroxy-12-[2'-(3''-hydroxy-4''-(2-methylpropyloxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-20-fluoro-1,14-dihydroxy-12-[2'-(4''-hydroxy-3''-(2-methylpropenyloxycyclohexyl)-1'-methylvinyl]-23,25-dimethoxy-13,19,21,27-tetramethyl-11,28-dioxa-4-azatricyclo[22.3.1.0^4,9]octacos-18-ene-2,3,10,16-tetraone;

17-Ethyl-20-fluoro-1,14-dihydroxy-12-[2'-(4''-cinnamyloxy-3''-hydroxycyclohexyl)-1'-methylvinyl]-23,25-dimethoxy-13,19,21,27-tetramethyl-11,28-dioxa-4- azatricyclo-[22.3.1.0^{4,9}]octacos-18-ene-2,3,10,16-tetraone;

17-Ethyl-20-fluoro-1,14-dihydroxy-12-[2'-(3''-cinnamyloxy-4''-hydroxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

17-Ethyl-20-fluoro-1-hydroxy-12-[2'-(4''-sec-butenyloxy-3''-hydroxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

17-Ethyl-20-fluoro-1-hydroxy-12-[2'-(3''-sec-butenyloxy-4''-hydroxycyclohexyl)-1'-methylvinyl]-23,25-dimethoxy-13,19,21,27-tetramethyl-11,28-dioxa-4-azatricyclo-[22.3.1.04,9]octacos-18-ene-2,3,10,16-tetraone;

17-Ethyl-20-fluoro-1-hydroxy-12-[2'-(4''-cinnamyloxy-3''-methoxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

17-Ethyl-20-fluoro-1-hydroxy-12-[2'-(3''-methoxy-4'-phenylpropyloxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

17-Ethyl-20-fluoro-1,14-dihydroxy-12-[2'-(4''-(4'''-methoxyphenyloxy)-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1,14-dihydroxy-12-[2'-(4''-(3'''-methoxyphenyloxy)-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1,14-dihydroxy--12-[2'-(4''-(6'''-hydroxynaphth-2-yloxy)-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1,14-dihydroxy-12-[2'-(4''-(4'''-hydroxyphenyloxy)-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1,14-dihydroxy-12-[2'-(4''-(4'''-methylthiophenyloxy)-3''-methoxycyclohexyl)-1'-methylvinyl]-23,25-dimethoxy-13,29,21,27-tetramethyl-11,28-dioxa-4-azatricyclo[22.3.1.0^{4,9}]octacos-18-ene-2,3,10,16-tetraone;

17-Ethyl-20-fluoro-1,14-dihydroxy-12-[2'-(4''-(2'''-methylphenyloxy)-3''-methoxycyclohexyl)-1'-methylvinyl]-23,25-dimethoxy-13,29,21,27-tetramethyl-11,28-dioxa-4-azatricyclo[22.3.1.0^{4,9}]octacos-18-ene-2,3,10,16-tetraone;

17-Ethyl-20-fluoro-1,14-dihydroxy-12-[2'-(4''-(3'''-methylphenyloxy)-3''-methoxycyclohexyl-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1,14-dihydroxy-12--[2'-(4''-(3''',4'''-dimethylphenyloxy)-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1-hydroxy-12-[2'-(4''-allyloxy-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1-hydroxy-12-[2'-(4''-(2-butynyloxy)-3''-methoxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

17-Ethyl-20fluoro-1-hydroxy-12-[2'-(4'''-cinnamyloxy-3''-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1-hydroxy-12-[2'-(3''-methoxy-4'-phenylpropyloxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

17-Ethyl-20-fluoro-1-hydroxy-12-[2'-(4''-allyloxy-3''-hydroxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

17-Ethyl-20-fluoro-1-hydroxy-12-[2'-(3''-allyloxy-4''-hydroxycyclohexyl)-1'-methylvinyl]-23,25-dimethoxy-13,19,21,27-tetramethyl-11,28-dioxa-4-azatricyclo[22.3.1.0^{4,9}]-octacos-18-ene-2,3,10,16-tetraone;

17-Ethyl-20-fluoro-1-hydroxy-12-[2'-(3''-hydroxy-4''-isopropyloxycyclohexyl)-1'-methylvinyl]-23,25-dimethoxy 13,19,21,27-tetramethyl-11,28-dioxa-4-azatricyclo[22.3.1.0^{4,9}]-octacos-18-ene-2,3,10,16-tetraone;

17-Ethyl-20-fluoro-1-hydroxy-12-[2'-(4''-hydroxy-3''-isopropyloxycyclohexyl)-1'-methylvinyl]-23,25-dimethoxy-13,19,21,27-tetramethyl-11,28-dioxa-4-azatricyclo[22.3.1.0^{4,9}]-octacos-18-ene-2,3,10,16-tetraone;

17-Ethyl-20-fluoro-1-hydroxy-12-[2'-(4''-(trans-2-butenyloxy)-3''-hydroxycyclohexyl)-1'-methylvinyl]23,25-dimethoxy-13,19,21,27-tetramethyl-11,28-dioxa-4-azatricyclo-[22.3.1.0^{4,9}]octacos-18-ene-2,3,10,16-tetraone;

17-Ethyl-20-fluoro-1-hydroxy-12-[2'-(3''-(trans-2-butenyloxy)-4''-hydroxycyclohexyl)-1'-methylvinyl]23,25-dimethoxy-13,19,21,27-tetramethyl-11,28-dioxa-4-azatricyclo-[22.3.1.0^{4,9}]octacos-18-ene-2,3,10,16-tetraone;

17-Ethyl-20-fluoro-1-hydroxy-12-[2'-(3''-hydroxy-4''-(3-methyl-2-butenyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1-hydroxy-12-[2'-(4''-hydroxy-3''-(3-methyl-2-butenyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1-hydroxy-12-[2'-(3''-hydroxy-4''-(2-methylpropenyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1-hydroxy-12-[2'-(4''-hydroxy-3''-(2-methylpropenyloxycyclohexyl)-1'-methylvinyl]-23,25-dimethoxy-13,19,21,27-tetramethyl- 11,28-dioxa-4-azatricyclo[22.3.1.0⁴,⁹]octacos-18-ene-2,3,10,16-tetraone;

17-Ethyl-20-fluoro-1-hydroxy-12-[2'-(3"-cinnamyloxy-4"-hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1,14-dihydroxy-12-[2'-(4"-sec-phenethyloxy-3"-methoxycyclohexyl)-1'-methylvinyl]-23,25-dimethoxy-13,19,21,27-tetramethyl-12,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-(2-methylcinnamyloxy)-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1,14-dihydroxy-12-[2'-(4"-(4-methyl-2,4-hexadienyloxy)-3'-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-(p-methoxycinnamyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-(3''',4'''-methylenedioxycinnamyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-(4,4-dimethyl-2-trans-pentenyloxy)-3'-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,4-dihydroxy-12-[2'-(4"-(3-cyclohexyl-2-trans-propenyloxy)-3'-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-p-fluorocinnamyloxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4'-chlorocinnamyloxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-p-bromocinnamyloxy-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1,14-dihydroxy-12-[2'-(3"-methoxy-4"-p-fluorophenylpropyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(3",4"-diallyloxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-Ethyl-20-fluoro-1-hydroxy-12-[2'-(3",4"-dipropyloxycyclohexyl)-1'-methylvinyl]-23,25-dimethoxy-13,19,21,27-tetramethyl-11,28-dioxa-4-azatricyclo[22.3.1.0⁴,⁹]-octacos-18-ene-2,3,10,16-tetraone;

17-Ethyl-20-fluoro-1,14-dihydroxy-12-[2'-(4"-(2-benzylamino)-ethoxy-3"-methoxycyclohexyl)-1'-methylvinyl]-23,25-dimethoxy-13,19,21,27-tetramethyl-11,28-dioxa-4-azatricyclo[22.3.1.04,9]octacos-18-ene-2,3,10,16-tetra-one;

17-Ethyl-20-fluoro-1-hydroxy-12-[2'-(4"-(2-benzylamino)-ethoxy-3"-methoxycyclohexyl)-1'-methylvinyl]-23,25-dimethoxy-13,19,21,27-tetramethyl-11,28-dioxa-4-azatricyclo-[22.3.1.04,9]octacos-18-2,3,10,16-tetraone;

17-Ethyl-20-fluoro-1,14-dihydroxy-12-[2'-(2-benzyloxyethoxy)-3"-methoxycyclohexyl)-1'-methylvinyl]-23,25-dimethoxy-13,19,21,27-tetramethyl-11,28-dioxa-4-azatricyclo[22.3.1.04,9]octacos-18-ene-2,3,10,16-tetraone;

17-Ethyl-20-fluoro-1,14-dihydroxy-12-[2'-(4'-benzyloxymethoxy-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1,14-dihydroxy-12-[2'-(4"-(naphth-2-yloxy)-3"-allyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-(ethoxycarbomethoxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-(p-hydroxycinnamyl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4"-(p-hydroxycinnamyl)oxy-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1,14-dihydroxy-12-[2'-(4"-(3''',5'''-difluorocinnamyl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4"-(3''',5'''-difluorocinnamyl)oxy-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Allyl-20-fluoro-1,14-dihydroxy-12-[2'-(4"-amino-3"-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-20-fluoro-1-hydroxy-12-[2'-(4"-amino-3"-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4"-amino-3"-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-amino-3''-phenoxycyclohexyl-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-phenoxy-3''-aminocyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-dimethylamino-3''-phenoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1-hydroxy-12-[2'-(4''-amino-3''-(4'''-methoxyphenoxy)cyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1-hydroxy-12-[2'-(4''-amino-3''-(4'''-hydroxyphenoxy)cyclohexyl)-1'-methylvinyl]23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1-hydroxy-12-[2'-(4''-acetylamino-3''-phenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-amino-3''-(4'''-fluorophenoxy)cyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1,14-dihydroxy-12-[2'-(4''-amino-3'-(4'''-carboxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-amino-3''-(4'''-trifluoromethylphenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-amino-3''-(3''',4'''-dimethoxyphenoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-20-fluoro-1,14-dihydroxy-12-[2'-(4''-amino-3'-(4'''-methoxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-amino-3''-(4'''-methylphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-amino-3''-(4'''-methylphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-amino-3''-(3'''-methoxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-amino-3''-(3'''-hydroxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-N-(2-propenyl)amino-3''-phenoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1-hydroxy-12-[2'-(4''-(acetylamino-3''-(4'''-methoxyphenoxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-amino-3''-allyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-amino-3''-allyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-allyloxy-3''-aminocyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-amino-3''-cinnamyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''amino-3''-cinnamyloxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Allyl-20-fluoro-1,14-dihydroxy-12-[2'-(4''-amino-3''-cinnamyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-amino-3''-(3'''-phenylpropyloxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-amino-3'''-phenylpropyloxy)cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1,14-dihydroxy-12-[2'-(4''-amino-3''-(2'''-benzyloxyethoxy)-cyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-20-fluoro-1-hydroxy-12-[2'-(4''-amino-3''-(2'''-benzyloxyethoxy)cyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-20-fluoro-1,14-dihydroxy-12-[2'-(4''-amino-3''-(4'''-hydroxycinnamyloxy)cyclohexyl)-1'-methylvinyl]23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1-hydroxy-12-[2'-(4''-amino-3''-(4'''-hydroxycinnamyloxy)cyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1,14-dihydroxy-12-[2'-(4''-amino-3''-(4'''-hydroxycinnamyloxy)cyclohexyl)-1'-methylvinyl]23,25-dimethoxy-13,19,21,27-tetramethyl-11,28-dioxa-4-azatricyclo[22.3.1.0^{4,9}]octacos-18-ene-2,3,10,16-tetraone;

17-Allyl-20-fluoro-1-hydroxy-12-[2'-(4''-amino-3''-(4'''-hydroxycinnamyloxy)cyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1,14-dihydroxy-12-[2'-(4''-acetylamino-3''-allyloxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

17-Ethyl-20-fluoro-1-hydroxy-12-[2'-(4''-acetylamino-3''-allyloxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

17-Ethyl-20-fluoro-1-hydroxy-12-[2'-(4''-N-(2-propenyl)amino-3''-allyloxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

17-Ethyl-20-fluoro-1,14-dihydroxy-12-[2'-(4''-(L-phenylalanine)-amido-3''-allyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1,14-dihydroxy-12-[2'-(4''-(D-phenylalanine)-amido-3''-allyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1-hydroxy-12-[2'-(4''-cyclopropanecarboxamido-3''-allyloxycyclohexyl)-1'-methylvinyl]23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1-hydroxy-12-[2'-(4''-formamido-3''-allyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1,14-dihydroxy-12-[2'-(4''(4''',5'''-dicarboethoxy-1''',2''',3'''-triazole)-3''-allyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1-hydroxy-12-[2'-(4''-benzylamino-3''-allyloxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

17-Ethyl-20-fluoro-1-hydroxy-12-[2'-(4''-dimethylamino-3''-allyl-oxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

17-Ethyl-20-fluoro-1,14-dihydroxy-12-[2'-(4''-trimethylamino-3''-allyloxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone iodide;

17-Ethyl-20-fluoro-1,2,14-trihydroxy-12-[2'-(4''-acetylamino-3''-allyloxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-trione;

17-Ethyl-20-fluoro-1,14-dihydroxy-12-[2'-(4''-(N-phenyl aminocarbonyl)amino-3''-allyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1,14-dihydroxy-12-[2'-(4''-(ethoxycarbonyl)-amino-3''-allyloxycyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1,14-dihydroxy-12-[2'-(4''-amino-3''-sec-butenyloxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

17-Ethyl-20-fluoro-1-hydroxy-12-[2'-(4''-amino-3''-sec-butenyloxycyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

17-Ethyl-20-fluoro-1,14-dihydroxy-12-[2'-(4''-amino-3'''-(3-methyl-2-butenyloxy)cyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

17-Ethyl-20-fluoro-1-hydroxy-12-[2'-(4''-amino-3''-(3-methyl-2-butenyloxy)cyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1,14-dihydroxy-12-[2'-(4''-amino-3''-(2-methyl-propenyloxy)cyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1-hydroxy-12-[2'-(4''-amino-3''-(2-methylpropenyloxy)cyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

17-Ethyl-20-fluoro-1-hydroxy-12-[2'-(4''-amino-3''-(4'''-methoxycinnamyloxy)cyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-20-fluoro-1-hydroxy-12-[2'-(4''-amino-3''-(4'''-fluorocinnamyloxy)cyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone; and 17-Ethyl-20-fluoro-1-hydroxy-12-[2'-(4''-amino-3''-(2-butynyloxy)-cyclohexyl)-1'-methylvinyl]-23,25-dimethoxy-13,19,21,27-tetramethyl-11,28-dioxa-4-azatricyclo-[22.3.1.0^{4,9}]octacos-18-ene-2,3,10,16-tetraone;

or a pharmaceutically acceptable salt thereof.

5. A compound of claim 4 which is:
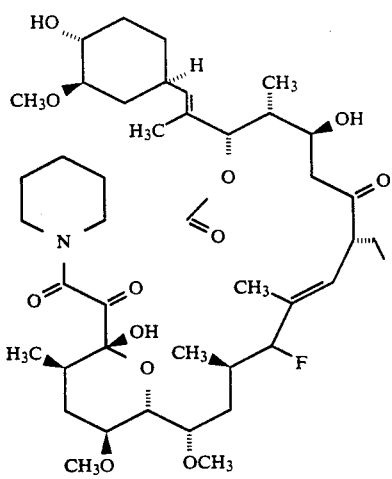
6. A compound of claim 4 which is:
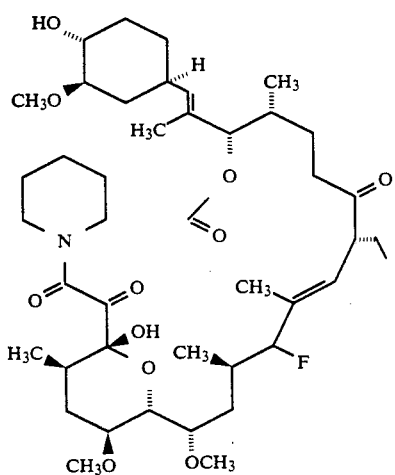
7. A compound of claim 4 which is:
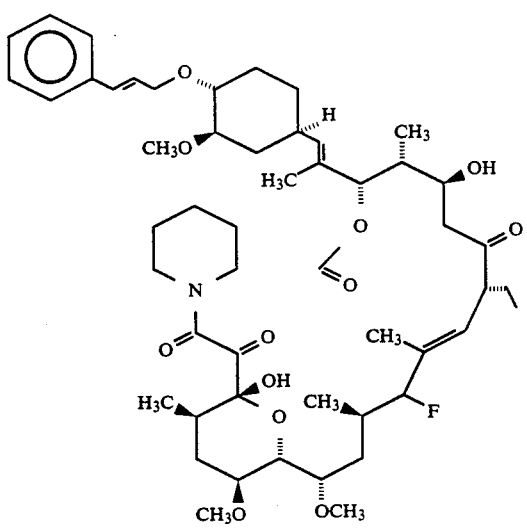
8. A compound of claim 4 which is:
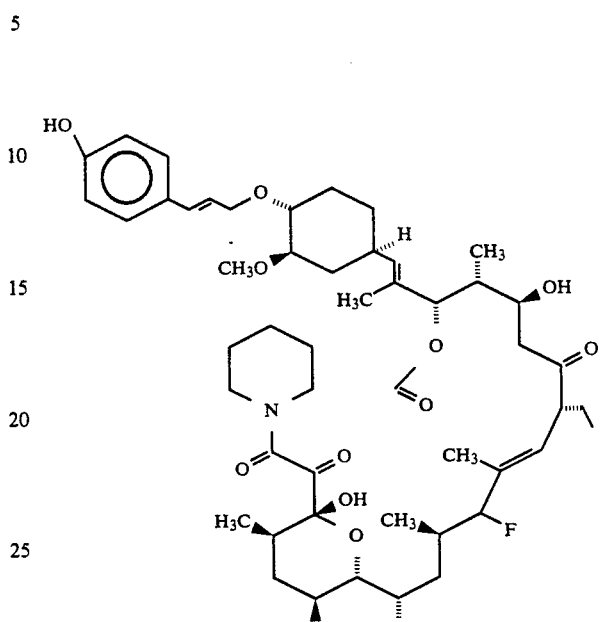
9. A compound of claim 4 which is:
10. A compound of claim 4 which is:

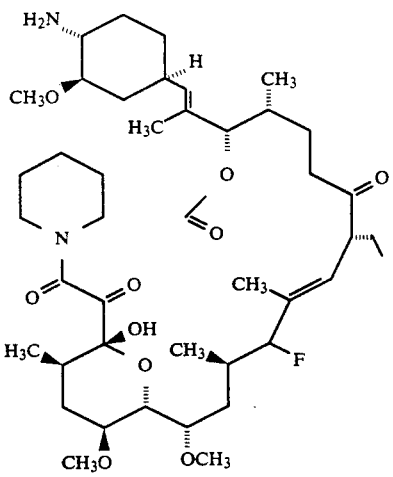

11. A pharmaceutical composition for the treatment of immunoregulatory disorders or diseases comprising a pharmaceutical carrier and a therapeutically effective amount of the compound of claim 1.

12. A pharmaceutical composition for the treatment of resistance to transplantation comprising a pharmaceutical carrier and a therapeutically effective amount of the compound of claim 1.

13. A pharmaceutical composition for the topical treatment of inflammatory and hyperproliferative skin diseases and or cutaneous manifestations of immunologically-mediated illnesses comprising a pharmaceutical carrier and a therapeutically effective amount of the compound of claim 1.

14. A pharmaceutical composition for the treatment of reversible obstructive airways disease comprising a pharmaceutical carrier and a therapeutically effective amount of the compound of claim 1.

15. A pharmaceutical composition for the treatment of male pattern alopecia or alopecia senilis a comprising a pharmaceutical carrier and a therapeutically effective amount of the compound of claim 1.

16. A method for the treatment of immunoregulatory disorders or diseases comprising the administration to a mammalian species in need of such treatment an effective amount of the compound of claim 1.

17. A method for the treatment of resistance to transplantation comprising the administration to a mammalian species in need of such treatment an effective amount of the compound of claim 1.

18. A method for the topical treatment of inflammatory and hyperproliferative skin diseases and or cutaneous manifestations of immunologically-mediated illnesses comprising the administration to a mammalian species in need of such treatment of an effective amount of the compound of claim 1.

19. A method for the treatment of reversible obstructive airways disease comprising the administration to a mammalian species in need of such treatment of an effective amount of the compound of claim 1.

20. A method for revitalizing hair comprising the administration to a mammalian species in need of such treatment of an effective amount of the compound of claim 1.

21. A method for the treatment of male pattern alopecia or alopecia senilis comprising the administration to a mammalian species in need of such treatment of an effective amount of the compound of claim 1.

* * * * *